United States Patent
Schmid et al.

(10) Patent No.: US 7,704,275 B2
(45) Date of Patent: Apr. 27, 2010

(54) CIRCUMFERENTIALLY NESTED EXPANDABLE DEVICE

(75) Inventors: Eric Schmid, San Diego, CA (US); Andrew Morris, San Diego, CA (US); Orlando Padilla, Laguna Niguel, CA (US)

(73) Assignee: REVA Medical, Inc., San Diego, CA (US)

( * ) Notice: Subject to any disclaimer, the term of this patent is extended or adjusted under 35 U.S.C. 154(b) by 576 days.

(21) Appl. No.: 11/627,898

(22) Filed: Jan. 26, 2007

(65) Prior Publication Data

US 2008/0183275 A1 Jul. 31, 2008

(51) Int. Cl.
*A61F 2/06* (2006.01)
(52) U.S. Cl. .................... 623/1.16; 623/1.15; 623/1.17; 623/1.3
(58) Field of Classification Search ......... 623/1.1–1.22; A61F 2/06
See application file for complete search history.

(56) References Cited

U.S. PATENT DOCUMENTS

| | | | |
|---|---|---|---|
| 3,620,218 A | 11/1971 | Schmitt |
| 4,261,390 A | 4/1981 | Belofsky |
| 4,383,555 A | 5/1983 | Finley |
| 4,553,545 A | 11/1985 | Maass et al. |
| 4,576,532 A | 3/1986 | Hanson et al. |
| 4,714,508 A | 12/1987 | Chivens et al. |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,762,129 A | 8/1988 | Bonzel |
| 4,776,337 A | 10/1988 | Palmaz |
| 4,817,600 A | 4/1989 | Herms et al. |
| 4,877,030 A | 10/1989 | Beck et al. |
| 4,922,905 A | 5/1990 | Strecker |
| 4,954,126 A | 9/1990 | Wallstén |
| 4,980,449 A | 12/1990 | Kohn et al. |
| 5,007,926 A | 4/1991 | Derbyshire |
| 5,040,548 A | 8/1991 | Yock |
| 5,059,211 A | 10/1991 | Stack et al. |

(Continued)

FOREIGN PATENT DOCUMENTS

EP 0756853 2/1997

(Continued)

OTHER PUBLICATIONS

Asahara, T. "Local delivery of vascular endothelial growth factor accelerates reendothelialization and attenuates intimal hyperplasia in balloon-insured rate carotid artery," Circulation 91: 2793-2801, 1995.

(Continued)

*Primary Examiner*—David Isabella
*Assistant Examiner*—Jason-Dennis Stewart
(74) *Attorney, Agent, or Firm*—Knobbe Martens Olson & Bear, LLP

(57) ABSTRACT

Expandable medical implants for maintaining support of a body lumen are disclosed. These implants comprise a circumferentially nested, diametrically expandable, moveable vascular device for enlarging an occluded portion of a vessel. The device can be configured to allow for motion such as rotating, translating, and/or slide and lock. One advantage of the circumferentially nested stent is that it maintains the expanded size, without significant recoil.

2 Claims, 21 Drawing Sheets

U.S. PATENT DOCUMENTS

| | | |
|---|---|---|
| 5,061,273 A | 10/1991 | Yock |
| 5,092,877 A | 3/1992 | Pinchuk |
| 5,099,060 A | 3/1992 | Kohn et al. |
| 5,108,416 A | 4/1992 | Ryan et al. |
| 5,140,094 A | 8/1992 | Kohn et al. |
| 5,151,100 A | 9/1992 | Abele et al. |
| 5,158,548 A | 10/1992 | Lau et al. |
| 5,192,307 A | 3/1993 | Wall |
| 5,194,570 A | 3/1993 | Kohn et al. |
| 5,195,984 A | 3/1993 | Schatz |
| 5,197,978 A | 3/1993 | Hess |
| 5,198,507 A | 3/1993 | Kohn et al. |
| 5,216,115 A | 6/1993 | Kohn et al. |
| 5,230,349 A | 7/1993 | Langberg |
| 5,232,445 A | 8/1993 | Bonzel |
| 5,242,399 A | 9/1993 | Lau et al. |
| 5,242,997 A | 9/1993 | Kohn et al. |
| 5,264,537 A | 11/1993 | Kohn et al. |
| 5,266,073 A | 11/1993 | Wall |
| 5,282,823 A | 2/1994 | Schwartz et al. |
| 5,300,085 A | 4/1994 | Yock |
| 5,306,286 A | 4/1994 | Stack et al. |
| 5,306,294 A | 4/1994 | Winston et al. |
| 5,317,077 A | 5/1994 | Kohn et al. |
| 5,344,426 A | 9/1994 | Lau et al. |
| 5,350,395 A | 9/1994 | Yock |
| 5,397,355 A | 3/1995 | Marin et al. |
| 5,402,554 A | 4/1995 | Oetiker |
| 5,421,955 A | 6/1995 | Lau et al. |
| 5,423,321 A | 6/1995 | Fontenot |
| 5,423,885 A | 6/1995 | Williams |
| 5,441,515 A | 8/1995 | Khosravi et al. |
| 5,443,496 A | 8/1995 | Schwartz et al. |
| 5,443,500 A | 8/1995 | Sigwart |
| 5,445,646 A | 8/1995 | Euteneur et al. |
| 5,449,382 A | 9/1995 | Dayton |
| 5,451,233 A | 9/1995 | Yock |
| 5,464,450 A | 11/1995 | Buscemi et al. |
| 5,476,508 A | 12/1995 | Amstrup |
| 5,484,449 A | 1/1996 | Amundson et al. |
| 5,490,962 A | 2/1996 | Cima et al. |
| 5,496,275 A | 3/1996 | Sirhan et al. |
| 5,496,346 A | 3/1996 | Horzewski et al. |
| 5,514,154 A | 5/1996 | Lau et al. |
| 5,527,337 A | 6/1996 | Stack et al. |
| 5,545,135 A | 8/1996 | Iacob et al. |
| 5,545,138 A | 8/1996 | Fugoso et al. |
| 5,549,556 A | 8/1996 | Ndondo-Lay et al. |
| 5,549,662 A | 8/1996 | Fordenbacher |
| 5,551,954 A | 9/1996 | Buscemi et al. |
| 5,554,182 A | 9/1996 | Dinh et al. |
| 5,556,413 A | 9/1996 | Lam |
| 5,571,166 A | 11/1996 | Dinh et al. |
| 5,575,816 A | 11/1996 | Rudnick et al. |
| 5,578,075 A | 11/1996 | Dayton |
| 5,587,507 A | 12/1996 | Kohn et al. |
| 5,591,172 A | 1/1997 | Bachmann et al. |
| 5,591,223 A | 1/1997 | Lock et al. |
| 5,591,224 A | 1/1997 | Schwartz et al. |
| 5,591,227 A | 1/1997 | Dinh et al. |
| 5,599,352 A | 2/1997 | Dinh et al. |
| 5,603,722 A | 2/1997 | Phan et al. |
| 5,607,463 A | 3/1997 | Schwartz et al. |
| 5,618,299 A | 4/1997 | Khosravi et al. |
| 5,626,600 A | 5/1997 | Horzewski et al. |
| 5,628,785 A | 5/1997 | Schwartz et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,651,174 A | 7/1997 | Schwartz et al. |
| 5,658,995 A | 8/1997 | Kohn et al. |
| 5,670,602 A | 9/1997 | Kohn et al. |
| 5,681,345 A | 10/1997 | Euteneuer |
| 5,697,967 A | 12/1997 | Dinh et al. |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,749,888 A | 5/1998 | Yock |
| 5,755,708 A | 5/1998 | Segal |
| 5,759,186 A | 6/1998 | Bachmann et al. |
| 5,766,710 A | 6/1998 | Turnlund et al. |
| 5,769,868 A | 6/1998 | Yock |
| 5,797,951 A | 8/1998 | Mueller |
| 5,799,384 A | 9/1998 | Schwartz et al. |
| 5,800,393 A | 9/1998 | Sahota |
| 5,800,507 A | 9/1998 | Schwartz |
| 5,836,965 A | 11/1998 | Jendersee et al. |
| 5,849,034 A | 12/1998 | Schwartz |
| 5,851,217 A | 12/1998 | Wolff et al. |
| 5,851,231 A | 12/1998 | Wolff et al. |
| 5,855,600 A | 1/1999 | Alt |
| 5,855,802 A | 1/1999 | Acciai et al. |
| 5,868,747 A | 2/1999 | Ochoa et al. |
| 5,876,419 A | 3/1999 | Carpenter et al. |
| 5,893,840 A | 4/1999 | Hull et al. |
| 5,906,639 A | 5/1999 | Rudnick et al. |
| 5,910,816 A | 6/1999 | Fontenot et al. |
| 5,921,952 A | 7/1999 | Desmond, III et al. |
| 5,944,726 A | 8/1999 | Blaeser et al. |
| 5,951,586 A | 9/1999 | Berg et al. |
| 5,954,729 A | 9/1999 | Bachmann et al. |
| 5,957,971 A | 9/1999 | Schwartz |
| 5,976,181 A | 11/1999 | Whelan et al. |
| 5,984,963 A | 11/1999 | Ryan et al. |
| 5,989,280 A | 11/1999 | Euteneur et al. |
| 6,007,545 A | 12/1999 | Venturelli |
| 6,015,387 A | 1/2000 | Schwartz et al. |
| 6,019,785 A | 2/2000 | Strecker |
| 6,033,436 A | 3/2000 | Steinke et al. |
| 6,036,715 A | 3/2000 | Yock |
| 6,048,521 A | 4/2000 | Kohn et al. |
| 6,080,190 A | 6/2000 | Schwartz |
| 6,093,157 A | 7/2000 | Chandrasekaran |
| 6,120,491 A | 9/2000 | Kohn et al. |
| 6,125,523 A | 10/2000 | Brown et al. |
| 6,132,457 A | 10/2000 | Chobotov |
| 6,160,084 A | 12/2000 | Langer et al. |
| 6,171,334 B1 | 1/2001 | Cox |
| 6,179,878 B1 | 1/2001 | Duerig et al. |
| 6,183,503 B1 | 2/2001 | Hart et al. |
| 6,190,403 B1 | 2/2001 | Fischell et al. |
| 6,197,789 B1 | 3/2001 | Grainger |
| 6,214,037 B1 | 4/2001 | Mitchell et al. |
| 6,224,626 B1 | 5/2001 | Steinke |
| 6,238,430 B1 | 5/2001 | Klumb et al. |
| 6,258,117 B1 | 7/2001 | Camrud et al. |
| 6,262,079 B1 | 7/2001 | Grainger et al. |
| 6,264,624 B1 | 7/2001 | Desmond, III et al. |
| 6,264,672 B1 | 7/2001 | Fisher |
| 6,280,473 B1 | 8/2001 | Lemperle et al. |
| 6,283,983 B1 | 9/2001 | Makower et al. |
| 6,284,862 B1 | 9/2001 | Kohn et al. |
| 6,287,329 B1 | 9/2001 | Duerig et al. |
| 6,287,333 B1 | 9/2001 | Appling et al. |
| 6,302,907 B1 | 10/2001 | Hijlkema |
| 6,309,350 B1 | 10/2001 | Van Tassel et al. |
| 6,319,277 B1 | 11/2001 | Rudnick et al. |
| 6,319,492 B1 | 11/2001 | Kohn et al. |
| 6,322,586 B1 | 11/2001 | Monroe et al. |

| | | |
|---|---|---|
| 6,350,277 B1 | 2/2002 | Kocur |
| 6,359,102 B1 | 3/2002 | Kemnitzer et al. |
| 6,383,211 B1 | 5/2002 | Staehle |
| 6,388,043 B1 | 5/2002 | Langer et al. |
| 6,391,032 B2 | 5/2002 | Blaeser et al. |
| 6,409,750 B1 | 6/2002 | Hyodoh et al. |
| 6,409,751 B1 | 6/2002 | Boatman et al. |
| 6,409,752 B1 | 6/2002 | Boatman et al. |
| 6,447,508 B1 | 9/2002 | Sharkey et al. |
| 6,451,034 B1 | 9/2002 | Gifford, III et al. |
| 6,475,477 B1 | 11/2002 | Kohn et al. |
| 6,485,510 B1 | 11/2002 | Camrud et al. |
| 6,488,700 B2 | 12/2002 | Klumb et al. |
| 6,491,704 B2 | 12/2002 | Gifford, III et al. |
| 6,491,705 B2 | 12/2002 | Gifford, III et al. |
| 6,491,938 B2 | 12/2002 | Kunz et al. |
| 6,527,791 B2 | 3/2003 | Fisher |
| 6,530,940 B2 | 3/2003 | Fisher |
| 6,530,958 B1 | 3/2003 | Cima et al. |
| 6,562,021 B1 | 5/2003 | Derbin et al. |
| 6,565,582 B2 | 5/2003 | Gifford, III et al. |
| 6,565,596 B1 | 5/2003 | White et al. |
| 6,569,191 B1 | 5/2003 | Hogan |
| 6,569,441 B2 | 5/2003 | Kunz et al. |
| 6,582,458 B1 | 6/2003 | White et al. |
| 6,582,472 B2 | 6/2003 | Hart |
| 6,602,497 B1 | 8/2003 | Kohn et al. |
| 6,607,551 B1 | 8/2003 | Sullivan et al. |
| 6,613,073 B1 | 9/2003 | White et al. |
| 6,620,356 B1 | 9/2003 | Wong et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,645,143 B2 | 11/2003 | Van Tassel et al. |
| 6,652,555 B1 | 11/2003 | Van Tassel et al. |
| 6,659,105 B2 | 12/2003 | Burbank et al. |
| 6,676,658 B2 | 1/2004 | Burbank et al. |
| 6,682,541 B1 | 1/2004 | Gifford, III et al. |
| 6,685,736 B1 | 2/2004 | White et al. |
| 6,689,153 B1 | 2/2004 | Skiba |
| 6,689,158 B1 | 2/2004 | White et al. |
| 6,695,857 B2 | 2/2004 | Gifford, III et al. |
| 6,699,257 B2 | 3/2004 | Gifford, III et al. |
| 6,699,280 B2 | 3/2004 | Camrud et al. |
| 6,709,449 B2 | 3/2004 | Camrud et al. |
| 6,720,402 B2 | 4/2004 | Langer et al. |
| 6,736,838 B1 | 5/2004 | Richter |
| 6,746,477 B2 | 6/2004 | Moore |
| 6,749,627 B2 | 6/2004 | Thompson et al. |
| 6,786,922 B2 | 9/2004 | Schaeffer |
| 6,790,221 B2 | 9/2004 | Monroe et al. |
| 6,792,979 B2 | 9/2004 | Konya et al. |
| 6,802,849 B2 | 10/2004 | Blaeser et al. |
| 6,852,308 B2 | 2/2005 | Kohn et al. |
| 6,869,143 B2 | 3/2005 | Secord |
| 6,878,159 B2 | 4/2005 | Iwasaka et al. |
| 6,916,868 B2 | 7/2005 | Kemnitzer et al. |
| 6,951,053 B2 | 10/2005 | Padilla et al. |
| 6,962,604 B2 | 11/2005 | Hijlkema |
| 6,964,680 B2 | 11/2005 | Shanley |
| 6,974,472 B2 | 12/2005 | Hong et al. |
| 6,974,475 B1 | 12/2005 | Wall |
| 6,991,647 B2 | 1/2006 | Jadhav |
| 7,041,126 B2 | 5/2006 | Shin et al. |
| 7,056,493 B2 | 6/2006 | Kohn et al. |
| 7,128,756 B2 | 10/2006 | Lowe et al. |
| 7,141,063 B2 | 11/2006 | White et al. |
| 7,175,653 B2 | 2/2007 | Gaber |
| 7,229,473 B2 | 6/2007 | Falotico et al. |
| 2001/0010015 A1 | 7/2001 | Hijlkema |
| 2001/0020173 A1 | 9/2001 | Klumb et al. |
| 2001/0029378 A1 | 10/2001 | Blaeser et al. |
| 2002/0040238 A1 | 4/2002 | Rudnick et al. |
| 2002/0052641 A1 | 5/2002 | Monroe et al. |
| 2002/0072656 A1 | 6/2002 | Van Tassel et al. |
| 2002/0077693 A1 | 6/2002 | Barclay et al. |
| 2002/0095204 A1 | 7/2002 | Thompson et al. |
| 2002/0120322 A1 | 8/2002 | Thompson et al. |
| 2002/0120323 A1 | 8/2002 | Thompson et al. |
| 2002/0123791 A1 | 9/2002 | Harrison |
| 2002/0138081 A1 | 9/2002 | Blaeser et al. |
| 2002/0138126 A1 | 9/2002 | Camrud et al. |
| 2002/0147489 A1 | 10/2002 | Hong et al. |
| 2002/0156456 A1 | 10/2002 | Fisher |
| 2002/0156457 A1 | 10/2002 | Fisher |
| 2003/0045923 A1 | 3/2003 | Bashiri |
| 2003/0074043 A1 | 4/2003 | Thompson |
| 2003/0078649 A1 | 4/2003 | Camrud et al. |
| 2003/0120334 A1 | 6/2003 | Gerberding |
| 2003/0176914 A1 | 9/2003 | Rabkin et al. |
| 2003/0199969 A1 | 10/2003 | Steinke et al. |
| 2003/0208262 A1 | 11/2003 | Gaber |
| 2003/0211135 A1 | 11/2003 | Greenhalgh et al. |
| 2003/0212451 A1 | 11/2003 | Cox et al. |
| 2003/0220682 A1 | 11/2003 | Kujawski |
| 2004/0054400 A1 | 3/2004 | Granada |
| 2004/0062788 A1 | 4/2004 | Richter |
| 2004/0068316 A1 | 4/2004 | Schaeffer |
| 2004/0086458 A1 | 5/2004 | Kohn et al. |
| 2004/0086462 A1 | 5/2004 | Kohn et al. |
| 2004/0093073 A1 | 5/2004 | Lowe et al. |
| 2004/0097959 A1 | 5/2004 | Thompson |
| 2004/0106971 A1 | 6/2004 | Schwartz et al. |
| 2004/0106977 A1 | 6/2004 | Sullivan et al. |
| 2004/0133260 A1 | 7/2004 | Schwartz et al. |
| 2004/0143319 A1 | 7/2004 | Schwartz et al. |
| 2004/0167616 A1 | 8/2004 | Camrud et al. |
| 2004/0186551 A1 | 9/2004 | Kao et al. |
| 2004/0191175 A1 | 9/2004 | Kohn et al. |
| 2004/0193251 A1 | 9/2004 | Rudnick et al. |
| 2004/0224003 A1 | 11/2004 | Schultz |
| 2004/0236401 A1 | 11/2004 | Shin et al. |
| 2004/0243217 A1 | 12/2004 | Andersen et al. |
| 2004/0243218 A1 | 12/2004 | Schaeffer |
| 2005/0038503 A1 | 2/2005 | Greenhalgh et al. |
| 2005/0106119 A1 | 5/2005 | Brandom et al. |
| 2005/0123481 A1 | 6/2005 | Kohn et al. |
| 2005/0165203 A1 | 7/2005 | Kohn et al. |
| 2006/0020324 A1 | 1/2006 | Schmid et al. |
| 2006/0024266 A1 | 2/2006 | Brandom et al. |
| 2006/0026815 A1 | 2/2006 | Padilla et al. |
| 2006/0034769 A1 | 2/2006 | Kohn et al. |
| 2006/0036316 A1 | 2/2006 | Zeltinger et al. |
| 2006/0115449 A1 | 6/2006 | Pacetti |
| 2006/0136041 A1 | 6/2006 | Schmid et al. |
| 2006/0182779 A1 | 8/2006 | Brandom et al. |
| 2006/0204440 A1 | 9/2006 | Kohn et al. |
| 2007/0010870 A1 | 1/2007 | Alt et al. |
| 2007/0032854 A1 | 2/2007 | Schmid et al. |
| 2007/0032857 A1 | 2/2007 | Schmid et al. |
| 2007/0061004 A1 | 3/2007 | Steinke |
| 2007/0142901 A1 | 6/2007 | Steinke |

FOREIGN PATENT DOCUMENTS

| | | |
|---|---|---|
| JP | 9-313617 | 12/1997 |
| WO | WO 90/14046 A1 | 11/1990 |
| WO | WO 94/21196 A2 | 9/1994 |
| WO | WO 94/21196 A3 | 2/1995 |
| WO | WO 96/14030 A1 | 5/1996 |
| WO | WO 97/07751 A1 | 3/1997 |
| WO | WO 97/42911 A1 | 11/1997 |
| WO | WO 98/22045 | 5/1998 |
| WO | WO 98/22073 A2 | 5/1998 |
| WO | WO 98/22073 A3 | 2/1999 |
| WO | WO 99/08740 A1 | 2/1999 |

| | | |
|---|---|---|
| WO | WO 99/15106 A1 | 4/1999 |
| WO | WO 99/40874 A1 | 8/1999 |
| WO | WO 99/65421 A2 | 12/1999 |
| WO | WO 99/65421 A3 | 1/2000 |
| WO | WO 00/09195 A1 | 2/2000 |
| WO | WO 00/10623 A1 | 3/2000 |
| WO | WO 00/30565 A1 | 6/2000 |
| WO | WO 00/59405 A1 | 10/2000 |
| WO | WO 00/62708 A1 | 10/2000 |
| WO | WO 00/71058 A1 | 11/2000 |
| WO | WO 01/24735 A1 | 4/2001 |
| WO | WO 01/35864 A1 | 5/2001 |
| WO | WO 01/51114 A2 | 7/2001 |
| WO | WO 01/70298 A2 | 9/2001 |
| WO | WO 01/87180 A2 | 11/2001 |
| WO | WO 01/51114 A3 | 1/2002 |
| WO | WO 01/70298 A3 | 2/2002 |
| WO | WO 00/62708 C2 | 6/2002 |
| WO | WO 01/87180 A3 | 6/2002 |
| WO | WO 02/47582 A2 | 6/2002 |
| WO | WO 02/053204 A2 | 7/2002 |
| WO | WO 02/054990 A2 | 7/2002 |
| WO | WO 02/047582 A3 | 10/2002 |
| WO | WO 02/054990 A3 | 11/2002 |
| WO | WO 02/053204 A3 | 3/2003 |
| WO | WO 03/022178 A1 | 3/2003 |
| WO | WO 03/047464 A2 | 6/2003 |
| WO | WO 03/057076 A1 | 7/2003 |
| WO | WO 03/047464 A3 | 9/2003 |
| WO | WO 03/047464 C2 | 11/2003 |
| WO | WO 03/094798 A1 | 11/2003 |
| WO | WO 03/099161 A2 | 12/2003 |
| WO | WO 03/099161 A3 | 2/2004 |
| WO | WO 2004/019820 A1 | 3/2004 |
| WO | WO 2004/026112 A2 | 4/2004 |
| WO | WO 2004/032803 A1 | 4/2004 |
| WO | WO 2004/026112 C2 | 6/2004 |
| WO | WO 2004/026112 A3 | 10/2004 |
| WO | WO 2004/096340 A1 | 11/2004 |
| WO | WO 2004/110312 A1 | 12/2004 |
| WO | WO 2006/010636 A1 | 2/2006 |
| WO | WO 2006/014596 A1 | 2/2006 |
| WO | WO 2006/020616 A1 | 2/2006 |
| WO | WO 2006/107608 A1 | 10/2006 |
| WO | WO 2007/084444 A2 | 7/2007 |

OTHER PUBLICATIONS

Autieri, M.V. et al. "Antisense oligonucleotides to the p65 subunit of NF-Kb inhibit human vascualr smooth muscle cell adherence and proliferation and prevent neointima formation in rat carotid arteries," Biochemical and Biophysical Research Communications 213: 827-836, 1995.

Brauner, R. "Controlled periadverntital administration of verapamil inhibits neointimal smooth muscle cell proliferation and ameliorates vasomotor abnormalities in experimental vein bypass grafts," The Journal of Thoracic and Cardiovascular Surgery 114: 53-63, 1997.

Carmeliet, P, et al. "Inhibitory role of plasminogen inhibitor-1 in arterial wound healing and neointima formation," Circulation 96: 3180-3191, 1997.

Epstein, S.E. et al. "Cytotoxic effects of a recombinant chimeric toxin on rapidly proliferating vascular smooth muscle cells," Circulation 84: 778-787, 1991.

Hu, Y. "Inhibition of neointima hyperplasia of mouse vein grafts by locally applied suramin," Circulation 100: 861-868, 1999.

Kurisu, Y. et al. "Protective effect of beraprost sodium, a stable prostacyclin analogue, on cardiac allograft vasculopathy in rats," Hiroshima Journal of Medical Science 56: 11-19, 1997.

Morishita, R. et al. "Novel in vitro gene transfer method for study of local modulators in vascular smooth muscle cells," Hypertension 21: 894-899, 1993.

Nerem, R.M. et al. "Tissue engineering and the vascular system, synthetic biodegradable polymer scaffolds," pp. 164-185, 1997.

Von Der Leyen, H.E. et al. "Gene therapy neointimal vascular lesion: in vivo transfer of endothelial cell nitric oxide synthase gene," PNAS USA 92:1137-1141, 1995.

Yasukawa, H. "Inhibition of intimal hyperplasia after balloon injury by antibodies to intercellular adhesion molecule-1 and lymphocyte funtion, Associated antigen-1," Circulation 95: 1515-1522, 1997.

Balcon, R. et al., *Recommendations on stent manufacture, implantation and utilization*, European Heart Journal, Oct. 1997, vol. 18, pp. 1536-1547.

Charles, Roger et al., *Ceramide-Coated Balloon Catheters Limit Neointimal Hyperplasia After Stretch Injury in Carotid Arteries*, Circulation Research, 2000; 87; pp. 282-288.

Coroneos, Emmanuel et al., *Differential Regulation of Sphingomyelinase and Ceramidase Activities by Growth Factors and Cytokines*, The Journal of Biological Chemistry, Oct. 6, 1995, vol. 270, No. 40, pp. 23305-22309.

Coroneos, Emmanuel et al., *Sphingolipid metabolites differentially regulate extracellular signal-regulated kinase and stress-activated protein kinase cascades*, Biochemical Journal, 1196; 316, pp. 13-17 (Printed in Great Britain).

Jacobs, Leila S. et al., *Sphingolipids as mediators of effects of platelet-derived growth factor in vascular smooth muscle cells*, American Journal of Physiology (American Physiological Society), 1993, pp. C740-C747.

Tanguay, Jean Francois et al., *Current Status of Biodegradable Stents*, Cardiology Clinics, Contemporary Interventional Techniques, Nov. 1994, vol. 12, No. 4, pp. 699-713, W.B. Saunders Company.

Nikol, S. et al., *Molecular biology and post-angioplasty restenosis*, Atherosclerosis, 1996; 123, pp. 17-31.

Phillips, Paul S. MD, et al., *The Stenter's Notebook*, 1998, (entire book), Physicians' Press, Birmingham, Michigan.

Ratner, Buddy D. et al., *Biomaterials Science, An Introduction to Materials in Medicine*, 2nd Edition, 2004, (entire book), Elsevier Academic Press.

Serruys, Patrick W. et al., *Handbook of Coronary Stents*, Fourth Edition, 2002, (entire book), Martin Dunitz Ltd.

Atala, Anthony et al., *Synthetic Biodegradable Polymer Scaffolds*, 1997, (entire book), Birkhauser Boston.

Co-pending U.S. Appl. No. 60/866,281, filed Nov. 17, 2006. Title: Halogen-Containing Aromatic Polyesters and Polyamides for Medical Applications.

Co-pending U.S. Appl. No. 60/885,600, filed Jan. 18, 2007. Title: Halogen-Containing Aromatic Polyesters and Polyamides for Medical Applications.

Co-pending U.S. Appl. No. 60/852,471, filed Oct. 17, 2006. Title: N-Substituted Monomers and Polymers.

Co-pending U.S. Appl. No. 60/852,513, filed Oct. 17, 2006. Title: N-Substituted Monomers and Polymers.

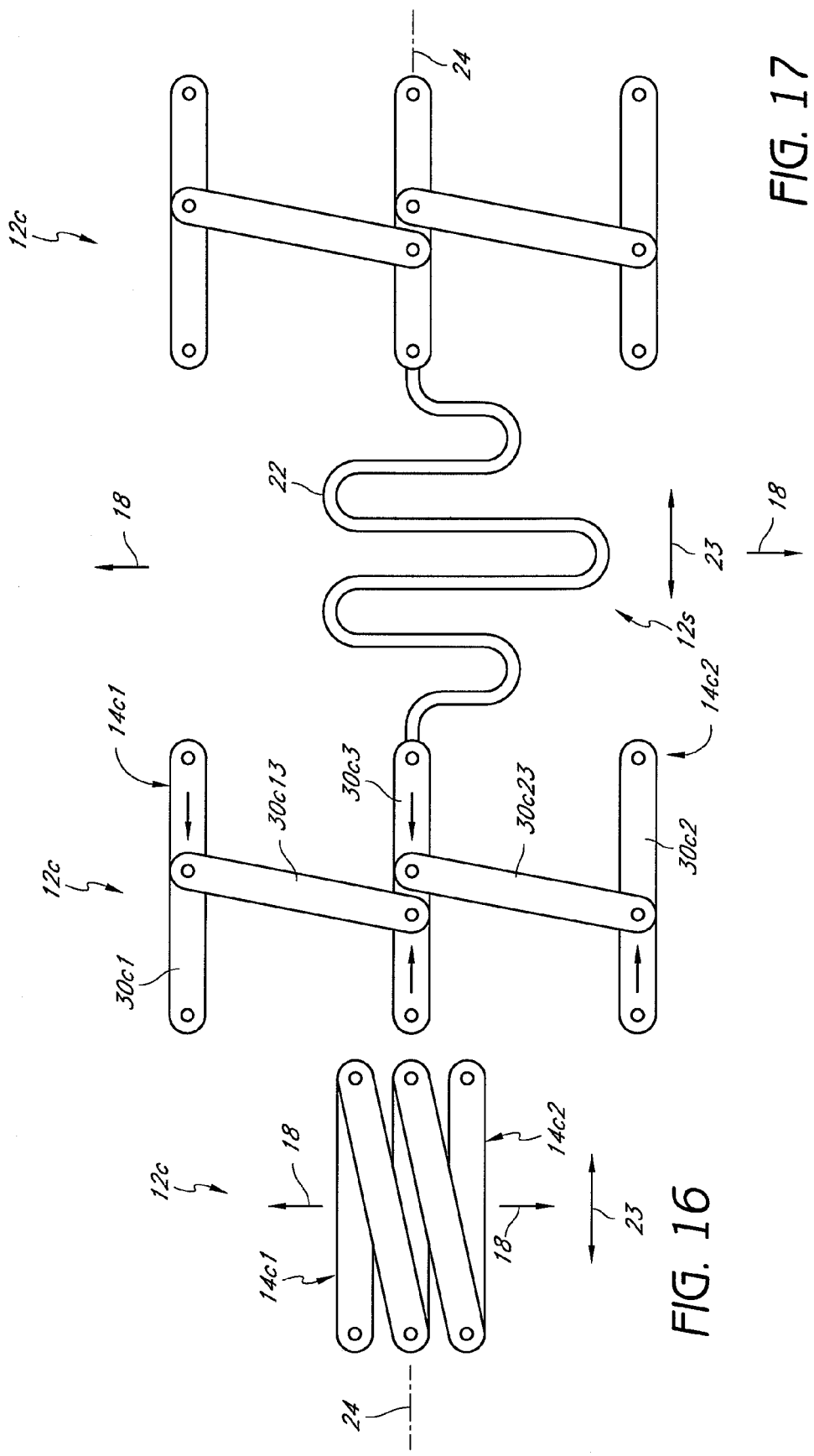

CIRCUMFERENTIALLY NESTED EXPANDABLE DEVICE

BACKGROUND

1. Field of the Inventions

The present inventions relate generally to expandable medical implants for maintaining support of a body lumen, and more particularly, to a predominantly circumferentially nested, diametrically expandable, moveable device for enlarging a portion of a body lumen.

2. Description of the Related Art

Stents or expandable stent grafts are implanted in a variety of body lumens in an effort to maintain their patency. The body lumens no matter how large or small can be vascular and nonvascular. These devices are typically intraluminally implanted by use of a catheter, which is inserted at an easily accessible location and then advanced to the deployment site. The stent is initially in a radially compressed or collapsed state to enable it to be maneuvered through the lumen. Once in position, the stent is deployed which, depending on its configuration, can be achieved either automatically or manually, by for example, the inflation of a balloon about which the stent is carried on the catheter.

An important and frequent use of stents is the treatment of blood vessels in situations where part of the vessel wall or stenotic plaque blocks or occludes fluid flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent can overcome the tendency of diseased vessel walls to collapse, thereby maintaining a more normal flow of blood through that vessel. Stents are also now being used in other clinical conditions such as in patients with unstable vulnerable plaque lesions.

As stents are normally employed to hold open an otherwise blocked, constricted or occluded lumen, a stent must exhibit sufficient radial or hoop strength in its expanded state to effectively counter the anticipated forces. Additionally, it can be beneficial for the stent to be as compact as possible in its collapsed state in order to facilitate its advancement through the lumen. As a result, it is advantageous for a stent to have as large an expansion ratio as possible.

An additional consideration is the longitudinal flexibility of the device. Such characteristic is important not only in maneuvering the stent into position, which can require the traversal of substantial convolutions of the vasculature, but also to better conform to any curvature of the vasculature at the deployment site. At the same time it is, however, necessary for the stent to nonetheless exhibit sufficient radial strength to provide the necessary support for the lumen walls upon deployment.

A number of very different approaches have been previously devised in an effort to address these various requirements. A popular approach calls for the stent to be constructed wholly of wire. The wire is bent, woven and/or coiled to define a generally cylindrical structure in a configuration that has the ability to undergo radial expansion. The use of wire has a number of disadvantages associated therewith including for example, its substantially constant cross-section which can cause greater or lesser than an ideal amount of material to be concentrated at certain locations along the stent. Additionally, wire has limitations with respect to the shapes it can be formed into thus limiting the expansion ratio, coverage area, flexibility and strength that can ultimately be attained therewith.

As an alternative to wire-based structures, stents have been constructed from tube stock. By selectively removing material from such tubular starting material, a desired degree of flexibility and expandability can be imparted to the structure. Etching techniques as well as laser-cutting processes are utilized to remove material from the tube. Laser cutting provides for a high degree of precision and accuracy with which very well defined patterns of material can be removed from the tube to conversely leave very precisely and accurately defined patterns of material in tact. The performance of such stent is very much a function of the pattern of material which remains (i.e., design) and material thickness. The selection of a particular pattern can have a profound effect on the coverage area, expansion ratio and strength of the resulting stent as well as its longitudinal flexibility and longitudinal dimensional stability during expansion.

While the tube-based stents offer many advantages over the wire-based designs, it is nonetheless desirable to improve upon such designs in an effort to further enhance longitudinal flexibility and longitudinal dimensional stability during radial expansion without sacrificing radial hoop strength.

One stent design described by Fordenbacher, see e.g., U.S. Pat. Nos. 5,549,662 and 5,733,328, employs a plurality of elongated parallel stent components, each having a longitudinal backbone that spans the entire axial length of the stent and a plurality of opposing circumferential elements or fingers extending therefrom. The circumferential elements from one stent component weave into paired slots in the longitudinal backbone of an adjacent stent component. This weave-like interlocking configuration, wherein a circumferential element passes through the first slot in a pair and then weaves back through the second slot in the pair, is essential to Fordenbacher's goal of permitting radial expansion without material deformation. In addition, sufficient members of circumferential elements in the Fordenbacher stent can provide adequate scaffolding. Unfortunately, the circumferential elements have free ends, protruding from the paired slots. Moreover, the circumferential elements weaving through the paired slots also necessarily stand off from the lumen wall. Both the free ends and the stand off can pose significant risks of thrombosis and/or restenosis. Moreover, this stent design would tend to be rather inflexible as a result of the plurality of longitudinal backbones.

Some stents employ "jelly roll" designs, wherein a sheet is rolled upon itself with a high degree of overlap in the collapsed state and a decreasing overlap as the stent unrolls to an expanded state. Examples of such designs are described in U.S. Pat. No. 5,421,955 to Lau, U.S. Pat. Nos. 5,441,515 and 5,618,299 to Khosravi, and U.S. Pat. No. 5,443,500 to Sigwart. The disadvantage of these designs is that they tend to exhibit very poor longitudinal flexibility. In a modified design that exhibits improved longitudinal flexibility, multiple short rolls are coupled longitudinally. See e.g., U.S. Pat. No. 5,649,977 to Campbell and U.S. Pat. Nos. 5,643,314 and 5,735,872 to Carpenter. However, these coupled rolls lack vessel support between adjacent rolls. Furthermore, these designs exhibit extensive overlapping of stent elements in multiple layers, which makes the delivery profile rather thick.

Various types of stents, including those referenced above, are often described based on their means for expansion. For additional information, a variety of stents types are described by Balcon et al., "Recommendations on Stent Manufacture, Implantation and Utilization," European Heart Journal (1997), vol. 18, pages 1536-1547, and Phillips, et al., "The Stenter's Notebook," Physician's Press (1998), Birmingham, Mich.

Balloon expandable stents are manufactured in the collapsed condition and are expanded to a desired diameter with a balloon. The expandable stent structure can be held in the expanded condition by mechanical deformation of the stent as taught in, for example, U.S. Pat. No. 4,733,665 to Palmaz. Alternatively, balloon expandable stents can be held in the expanded condition by engagement of the stent walls with respect to one another as disclosed in, for example, U.S. Pat. No. 4,740,207 to Kreamer, U.S. Pat. No. 4,877,030 to Beck et al., and U.S. Pat. No. 5,007,926 to Derbyshire. Further still, the stent can be held in the expanded condition by one-way engagement of the stent walls together with tissue growth into the stent, as disclosed in U.S. Pat. No. 5,059,211 to Stack et al.

Although balloon expandable stents are the first stent type to be widely used in clinical applications, it is well recognized that current balloon expandable stents have a variety of shortcomings which can limit their effectiveness in many important applications. For example, these balloon expandable stents often exhibit substantial recoil (i.e., a reduction in diameter) immediately following deflation of the inflatable balloon. Accordingly, it can be necessary to over-inflate the balloon during deployment of the stent to compensate for the subsequent recoil. This is disadvantageous because it has been found that over-inflation can damage the blood vessel. Furthermore, a deployed balloon expandable stent can exhibit chronic recoil over time, thereby reducing the patency of the lumen. Still further, balloon expandable stents often exhibit foreshortening (i.e., a reduction in length) during expansion, thereby creating undesirable stresses along the vessel wall and making stent placement less precise. Still further, many balloon expandable stents, such as the original Palmaz-Schatz stent and later variations, are configured with an expandable mesh having relatively jagged terminal prongs, which increases the risk of injury to the vessel, thrombosis and/or restenosis.

Self-expanding stents are manufactured with a diameter approximately equal to, or larger than, the vessel diameter and are collapsed and constrained at a smaller diameter for delivery to the treatment site. Self-expanding stents are commonly placed within a sheath or sleeve to constrain the stent in the collapsed condition during delivery. After the treatment site is reached, the constraint mechanism is removed and the stent self-expands to the expanded condition. Most commonly, self-expanding stents are made of Nitinol or other shape memory alloy. One of the first self-expanding stents used clinically is the braided "WallStent," as described in U.S. Pat. No. 4,954,126 to Wallsten. Another example of a self-expanding stent is disclosed in U.S. Pat. No. 5,192,307 to Wall wherein a stent-like prosthesis is formed of plastic or sheet metal that is expandable or contractible for placement. Finally, U.S. Pat. No. 6,964,680 B2 to Shanley discloses an expandable medical device with a tapered hinge.

Heat expandable stents are similar in nature to self-expanding stents. However, this type of stent utilizes the application of heat to produce expansion of the stent structure. Stents of this type can be formed of a shape memory alloy, such as Nitinol or other materials, such as polymers, that must go through a thermal transition to achieve a dimensional change. Heat expandable stents are often delivered to the affected area on a catheter capable of receiving a heated fluid. Heated saline or other fluid can be passed through the portion of the catheter on which the stent is located, thereby transferring heat to the stent and causing the stent to expand. However, heat expandable stents have not gained widespread popularity due to the complexity of the devices, unreliable expansion properties and difficulties in maintaining the stent in its expanded state. Still further, it has been found that the application of heat during stent deployment can damage the blood vessel.

In summary, although a wide variety of stents have been proposed over the years for maintaining the patency of a body lumen, none of the existing schemes has been capable of overcoming most or all of the above described shortcomings. As a result, clinicians are forced to weigh advantages against shortcomings when selecting a stent type to use in a particular application. Accordingly, there remains a need for an improved stent: one that is compact and flexible enough when collapsed to permit uncomplicated delivery to the affected area; one that is sufficiently flexible upon deployment to conform to the shape of the affected body lumen; one that expands uniformly to a desired diameter; one that maintains the expanded size, without significant recoil; and one that has sufficient scaffolding to provide a clear through-lumen.

SUMMARY

Various embodiments of a circumferentially nested, diametrically expandable vascular device or stent for maintaining support of a body lumen are disclosed herein. Such embodiments of the vascular device can be expandable medical implants that can be circumferentially nested, expandable, rotating, translating, and moveable for enlarging an occluded portion of a vessel. For example, the vascular device can be a slide-and-lock vascular device. One advantage of embodiments of the circumferentially nested stent is that it maintains the expanded size, without significant recoil.

According to an embodiment, a circumferentially nested slide-and-lock stent is provided. The stent can be expandable from a collapsed state to an expanded state. The stent can comprise a tubular member having longitudinal and circumferential axes. The tubular member can comprise at least one linkage section, such as a slide-and-lock section. The linkage section can be disposed along the longitudinal axis. The linkage section can comprise at least one structural element and at least one link element.

The structural element can be disposed along the circumferential axis of the tubular member. The structural element can have first and second ends. The first end can be positionable substantially circumferentially adjacent the second end when the stent is in the unexpanded state. The first end can include at least one first protrusion and the second end can include at least one second protrusion.

The link element also can have first and second ends. The first end can have a first cavity disposed therein and the second end can have a second cavity disposed therein. The first and second cavities can be each sized and configured to engage the respective ones of the first and second protrusions to provide at least one of rotation and translation of the protrusion within the cavity in order to facilitate expansion of the stent to the expanded state.

In some embodiments, the linkage section can include a plurality of structural elements disposed with the first end of each structural element being positionable circumferentially adjacent to the second end of an adjacent structural element when the stent is in the unexpanded state. In this regard, a respective plurality of link elements can engage the first and second protrusions of the first and second ends of the structural elements in order to facilitate expansion of the stent. The plurality of structural elements can be disposed substantially coplanar within the linkage section when the stent is in the collapsed state. Additionally, the tubular member can comprise a plurality of linkage sections. Further, the stent can also comprise at least one flexible section which can be disposed intermediate the linkage sections along the longitudinal axis of the tubular member in order to tubularly interconnect the linkage sections.

In addition, the link element can be configured as an elongate link element. The first end of the structural element can also include a pair of first protrusions and the second end can include a pair of second protrusions. Further, at least one of the first and second cavities of the link element can be an aperture that passes through the respective one of the first and second ends of the link element.

In accordance with another embodiment, the stent can further comprise annularly-shaped female ratchet members that can be disposable within the first and second cavities of the link element. Each female ratchet member preferably can have a central lumen and at least one internal tooth oriented radially inwardly to within the lumen. The lumen can be sized and configured to receive the protrusion therein with the internal tooth engaging the protrusion in order to provide one-way rotation of the protrusion within the lumen. Thus, the stent would not be collapsible to the collapsed state upon being expanded to the expanded state. Further, the protrusion of the structural element can be configured as a male ratchet member having at least one male ratchet tooth extending radially outwardly. The male ratchet tooth can be configured to engage the internal tooth of the female ratchet member for providing one-way rotation of the protrusion within the lumen.

Another implementation provides that at least one of the first and second cavities of the link element can be a slot which translatably engages the protrusion. The slot can be axially disposed in the link element. In this regard, the slot can include a plurality of teeth along at least one side thereof. The teeth can be sized and configured to provide one-way translation of the protrusion within the slot such that the stent is not collapsible to the collapsed state upon being expanded to the expanded state. Finally, the structural element can include a ring element having a series of circumferentially-aligned protrusions disposed at least one of first and second ends of the ring element.

In accordance with another embodiment, the stent can comprise a tubular member that can include at least one linkage section. The linkage section can be disposed along the circumferential axis and can comprise at least one three-bar structural element. The three-bar structural element can comprise first and second stent block bodies and a stent body link.

The first and second stent block bodies can each have first and second ends. The stent block bodies can be disposed along the circumferential axis of the tubular member. Further, the first stent block body can have a first male member disposed at the first end thereof, and the second stent block body can have a second male member disposed at the second end thereof. The stent body link can have first and second ends. Further, the stent body link can have first and second cavities disposed at the respective ones of the first and second ends thereof. The first and second cavities can each be sized and configured to engage the respective ones of the first male member of the first stent block body and the second male member of the second stent block body to thereby interconnect the stent body link with the first and second stent block bodies.

Furthermore, the first stent block body can be positionable substantially circumferentially adjacent to the second stent block body when the stent is in the unexpanded state. In this regard, the first stent block body can be separable from the second stent block body upon rotation of the first and second male members within the respective ones of the first and second cavities to rotate the stent body link thereby expanding the stent to the expanded state.

The stent can further comprise annularly-shaped female ratchet members that can be disposable within the first and second cavities of the stent body link. Each female ratchet member can have a central lumen and at least one internal tooth oriented radially inwardly to within the lumen. The lumen can be sized and configured to receive the male member therein with the internal tooth engaging the male member for providing one-way rotation of the male member within the lumen such that the stent is not collapsible to the collapsed state upon being expanded to the expanded state.

The male member can be configured as a male ratchet member having at least one male ratchet tooth extending radially outwardly and being configured to engage the internal tooth of the female ratchet member for providing one-way rotation of the male member within the lumen such that the stent is not collapsible to the collapsed state upon being expanded to the expanded state.

In accordance with another embodiment, a circumferentially nested rotary three-bar linkage stent is provided that can be expandable from a collapsed state to an expanded state. Such an embodiment can comprise a tubular member having longitudinal and circumferential axes, and the tubular member can comprise at least one linkage section that can be disposed along the circumferential axis.

The linkage section can comprise at least one three-bar structural element. Additionally, the three-bar structural element can comprise first and second stent block bodies each having first and second ends, and can further include a stent body link. The stent block bodies can be disposed along the circumferential axis of the tubular member. The first stent block body can have a first cavity that can be disposed at the first end thereof, and the second stent block body can have a second cavity that can be disposed at the second end thereof.

The stent body link can have first and second ends. The stent body link can have first and second male members disposed at the respective ones of the first and second ends thereof. The first and second male members can each be sized and configured to engage the respective ones of the first cavity of the first stent block body and the second cavity of the second stent block body to thereby interconnect the stent body link with the first and second stent block bodies. In this regard, the first stent block body can be positionable substantially circumferentially adjacent to the second stent block body when the stent is in the unexpanded state. Further, the first stent block body can be separable from the second stent block body upon rotation of the first and second male members within the respective ones of the first and second cavities to rotate the stent body link, thereby expanding the stent to the expanded state.

In accordance with yet another embodiment, a circumferentially nested rotary-slide three-bar linkage stent is provided. The stent can comprise a tubular member having longitudinal and circumferential axes, and the tubular member can comprise at least one linkage section that can be disposed along the circumferential axis.

The linkage section can comprise at least one three-bar structural element. The three-bar structural element can comprise first and second end bars and a third shared bar. The first and second end bars can each have first and second ends. The end bars can be disposed along the circumferential axis of the tubular member. The first end bar can include a slot, which can be axially disposed along the first end bar and extend intermediate the first and second ends of the first end bar. The second end bar can include a cavity disposed at the first end of the second end bar.

The third shared bar can have first and second ends and first and second male members disposed at the respective ones of the first and second ends. The first and second male members can each be sized and configured to extend into the respective ones of the slot of the first end bar and the cavity of the second end bar to thereby interconnect the shared bar with the first and second end bars.

Further, the first end bar can be positionable substantially circumferentially adjacent to the second end bar when the stent is in the unexpanded state. The first end bar can be separable from the second end bar upon translation of the first male member within the slot and rotation of the second male member within the cavity to rotate and translate the shared bar, thereby expanding the stent to the expanded state.

In another embodiment, the second end bar can include the second male member disposed at the first end thereof, the third shared bar can have the first male member and a cavity disposed at the respective ones of the first and second ends thereof. The first male member can be sized and configured to extend into the slot of the first end bar. The cavity can be sized and configured to engage the second male member of the second end bar to thereby interconnect the shared bar with the first and second end bars In yet another embodiment, the first and second end bars can each include a slot that can be axially disposed along the end bar and extend intermediate the first and second ends thereof. In this regard, the third shared bar can have first and second male members each being sized and configured to extend into the slots of the respective ones of the first and second end bars to thereby interconnect the shared bar with the first and second end bars.

In another embodiment, the linkage section can comprise at least one four-bar structural element. The four-bar structural element can comprise first and second end bars and third and fourth shared bars. The first and second end bars can each have first and second ends. The end bars can be disposed along the circumferential axis of the tubular member and including a slot that can be axially disposed along the end bar and extending intermediate the first and second ends thereof. The third and fourth shared bars can each have first and second ends and first and second male members disposed at the respective ones of the first and second ends thereof. The first and second male members of the third shared bar can each be sized and configured to extend into the slots of the respective ones of the first and second end bars to thereby interconnect the third shared bar with the first and second end bars. Likewise, the first and second male members of the fourth shared bar can each be sized and configured to extend into the slots of the respective ones of the second and first end bars to thereby interconnect the fourth shared bar with the first and second end bars Thus, the first end bar can be positionable substantially circumferentially adjacent to the second end bar when the stent is in the unexpanded state. The first end bar can be separable from the second end bar upon translation of at least one of the first and second male members of the third shared bar and at least one of the first and second male members of the fourth shared bar through the respective slots of the first and second end bars to rotate and translate the third and fourth shared bars with respect to the first and second end bars thereby expanding the stent to the expanded state.

In yet another embodiment, a circumferentially nested scissor stent is provided. The stent can comprise a tubular member having longitudinal and circumferential axes. The tubular member can comprise at least one linkage section and an articulating member.

The linkage section can be disposed along the circumferential axis and comprise at least one structural element. The structural element can comprise first and second bars each having first and second ends. The bars can be disposed along the circumferential axis of the tubular member. The bars can be rotatably connected at the first ends thereof to form a coupling. The first bar can have an aperture disposed through a portion of the first end thereof.

The articulating member can have first and second ends. The first end of the articulating member can be connected to the first end of the second bar adjacent the coupling with the articulating member extending upwardly from therefrom into the aperture of the first bar. The articulating member can have a plurality of teeth disposed therealong. The teeth can be sized and configured to engage the aperture for providing one-way translational withdrawal of the articulating member from the aperture upon angular separation of the first bar from the second bar.

Therefore, the first bar can be positionable substantially circumferentially adjacent to the second bar when the stent is in the unexpanded state. The first bar can be separable from the second bar upon angular rotation of the first bar with respect to the second bar at the coupling thereby expanding the stent to the expanded state. The one-way translational withdrawal of the articulating member from the aperture can maintain angular displacement between the first and second bars at the coupling in order to prevent collapse of the stent to the collapsed state upon being expanded to the expanded state.

As discussed herein, embodiments disclosed herein provide a diametrically expanding, rotating and translating, moveable vascular device. An embodiment of such a device can be operative to move via rotation, translation, and/or slide and lock movement. Thus, embodiments of the vascular device, prosthesis or stent can comprise one or more expandable sections, segments or frames with each having one or more rotatable structural elements. Each structural element can have a plurality of articulating structural members, arms, bars or ribs.

A plurality of the rotating structural elements can be arranged longitudinally and circumferentially to create a rotating, expanding and locking stent prosthesis. During stent expansion, there can be relative rotational motion between associated structural members so that the stent expands from a first collapsed diameter to a second expanded diameter.

For example, a structural element can comprise two substantially identical or non-identical structural members that can be arranged so that they pivot around a common pivot point or axle. This design embodiment will enable negative displacement to occur in one axis while adding positive displacement in an orthogonal axis as a function of angle between the rotating members. The positive displacement desirably generates controlled stent expansion.

Some embodiments relate to stent designs which expand diametrically by rotary motion and lock into place. Advantageously, this enables stent designs which can expand without permanently deforming the stent material past its elastic limit.

Other embodiments of the diametrically expanding, rotating and translating, moveable vascular device relate to an expandable vascular device, prosthesis or stent utilizing a point lock system or mechanism. The stent structural members, for example, two members, can rotate or pivot around an axle to provide generally diametric stent expansion. Generally, the rotating members do not translate in the point-lock stent embodiments.

Yet other embodiments relate to an expandable vascular device, prosthesis or stent utilizing a rotary slide system or mechanism. The stent structural members, for example, arranged in a three-member linkage mechanism, can pivot and translate to provide generally diametric stent expansion.

Yet other embodiments relate to an expandable vascular device, prosthesis or stent utilizing both point lock and rotary slide systems or mechanisms. The stent structural members, for example, arranged in a four-member linkage mechanism, can pivot and translate to provide generally diametric stent expansion.

Yet other embodiments relate to an expandable vascular device, prosthesis or stent utilizing a ball and socket system or mechanism. The stent structural members, for example, arranged in a three-member linkage mechanism, can pivot and translate to provide generally diametric stent expansion.

Yet other embodiments relate to an expandable vascular device, prosthesis or stent utilizing a ratchet and pawl system or mechanism. The stent structural members, for example, a radial ratchet member and a lever pawl member, can be arranged such that as the ratchet member rotates about a point the pawl member translates to provide generally diametric stent expansion.

In another embodiment, an improved stent is provided that desirably is small enough and flexible enough when collapsed to permit uncomplicated delivery to the affected area; one that expands uniformly to a desired diameter; one that maintains the expanded size, without significant recoil; one that can have sufficient scaffolding to provide a clear through-lumen; one that supports endothelialization or covering of the stent with vessel lining, which in turn minimizes the risk of thrombosis; and one that can have a greater capacity to deliver therapeutic agents to minimize injury, treat restenosis and other vascular diseases. Some embodiments provide a stent that can be sufficiently flexible upon deployment to conform to the shape of the affected body lumen and one that expands uniformly to a desired diameter, without undesired change in length. There can be no change length or the stent length can increase or decrease with efficacy, as required or desired.

In some embodiments, axially offset stent sections can be linked together in a wide variety of techniques for example by utilizing linkage sections, segments or frames. The linkage sections can include spring elements that advantageously provide enhanced stent flexibility.

At full expansion, the stent articulating and/or interlocking structural members can be captured through a wide variety of techniques, to limit and control the stent maximum expansion. These include, for example, but are not limited to, hard stops, capture straps, overhanging elements, covers, tongue-groove configurations and other suitable geometries, that can be employed or created through a wide variety of techniques to provide for stent expansion control.

Some embodiments can utilize a number of features to create slide and lock mechanisms that allow for controlled and predictable device expansion. For example, deflectable and non-deflectable elements and members can be employed to achieve desired deployment and lock out performance. The skilled artisan will appreciate that a variety of mechanisms, features and/or geometries can readily be included to achieve the desired deployment and lock out performance. For example, mechanisms can be employed that incorporate the bulk of the structural element, or smaller localized sub-elements can be employed.

In other embodiments, structural elements can be linked together and interlocking elements captured through a wide variety of techniques. For example, channels can be created or added that allow the elements to slide within, between or therethrough. Other examples include, but are not limited to, capture straps, overhanging elements, covers, tongue-groove configurations and other suitable geometries, that can be employed or created through a wide variety of techniques to provide for linkage and capture of elements.

Stents in accordance with some embodiments can be fabricated or created using a wide variety of manufacturing methods, techniques and procedures. These include, but are not limited to, laser processing, milling, stamping, forming, casting, molding, laminating, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

The stent can be fabricated from at least one or more materials. In preferred variations to the above-described stents, the stent further can comprise a material selected from the group consisting of metals, polymers, and composites. Preferably, the polymer can comprise a bioresorbable polymer. More preferably, the polymer can comprise a radiopaque, bioresorbable polymer. In one aspect, the polymer forms a coating on at least a portion of the stent. The polymer coating can further comprise a biocompatible, bioresorbable polymer adapted to promote a selected biological response.

The vascular devices, prostheses or stents can be formed from a number of suitable materials. These include, without limitation, stainless steel alloys, spring-steel alloys, cobalt-chrome alloys, nickel-titanium alloys, titanium alloys, platinum-iridium alloys, tantalum and derivatives thereof, and combinations thereof, among others.

Advantageously, the substantially non-deforming rotary lock mechanisms of certain embodiments allow the use of other suitable materials as well. These include, but are not limited to, ceramics, polymers, rubbers, bioresorbable and other materials which dissipate in time, combinations thereof, among others.

A method for re-treatment of a body lumen is disclosed in accordance with another embodiment. The method can comprise the steps of: deploying to a region of the body lumen any of the above described stents, wherein the stent can be made from a bioresorbable polymer, and resides at the region for a period of time; and administering to the region, after the period of time, a second treatment, such as for example, treatments selected from the group consisting of a second stent of any kind, angioplasty, arthrectomy, surgical bypass, radiation, ablation, local drug infusion, etc., or any subsequent intervention or treatment.

In preferred variations to the above-described stents, the stent further can comprise a therapeutic agent.

In preferred variations to the above-described stents, the stent further can comprise a layered material. Preferably, the layered material can comprise a bioresorbable polymer.

One key design aspect of embodiments of an expandable vascular device is its deployment ratio, that is, the ratio of final maximum diameter to initial compacted diameter. Depending upon the particular design being pursued or the application being addressed, the deployment ratio can vary. Advantageously, certain stent embodiments can allow the number of elements to be increased or decreased, that is, varied, as needed or desired, to achieve optimization of the deployment ratio as well as device performance, crossing profile, flexibility, among others. This desirably adds to the device versatility and utility. Advantageously, dimensions (e.g., length, width, and the like) can also be modified to change expansion characteristics and features.

In preferred variations to the above-described stents, a cross-sectional geometry of at least a portion of the stent can be tapered so as to produce generally desirable blood flow characteristics when the stent is placed in a blood vessel lumen.

In preferred variations to the above-described stents, the stent further can comprise a retractable sheath sized for enclosing the tubular member during delivery to a treatment site.

In preferred variations to the above-described stents, the stent further can comprise a solid wall region. The solid wall region can further comprise an opening.

In preferred variations to the above-described stents, the stent further can comprise a polymeric sheath.

A system for treating a site within a vessel is also disclosed. The system can comprise a catheter having a deployment means, and any of the above-described stents, wherein the catheter is adapted to deliver the stent to the site and the deployment means is adapted to deploy the stent. In preferred variations, the catheter can be selected from the group consisting of over-the-wire catheters, coaxial rapid-exchange catheters, and multi-exchange delivery catheters.

Certain aspects, advantages and novel features of the various embodiments have been described herein above. Of course, it is to be understood that not necessarily all such advantages can be achieved in accordance with any particular embodiment. Thus, many embodiments can be carried out in a manner that achieves or optimizes one advantage or group of advantages as taught or suggested herein without necessarily achieving other advantages as can be taught or suggested herein.

All of these embodiments are intended to be within the scope of the present disclosure. These and other embodiments will become readily apparent to those skilled in the art from the following detailed description of the preferred embodiments having reference to the attached figures.

BRIEF DESCRIPTION OF THE DRAWINGS

The abovementioned and other features of the embodiments disclosed herein are described below with reference to the drawings of the preferred embodiments. The illustrated embodiments are intended to illustrate, but not to limit the same. The drawings contain the following figures:

FIG. 16 is a simplified schematic planar partial view of an expandable rotary circumferentially nested three-bar linkage stent in a nested state illustrating features and advantages in accordance with an embodiment.

FIG. 17 is a simplified schematic planar partial view of an expandable rotary circumferentially nested three-bar linkage stent in an expanded state illustrating features and advantages in accordance with an embodiment.

DETAILED DESCRIPTION OF THE PREFERRED EMBODIMENTS

Figure 1:
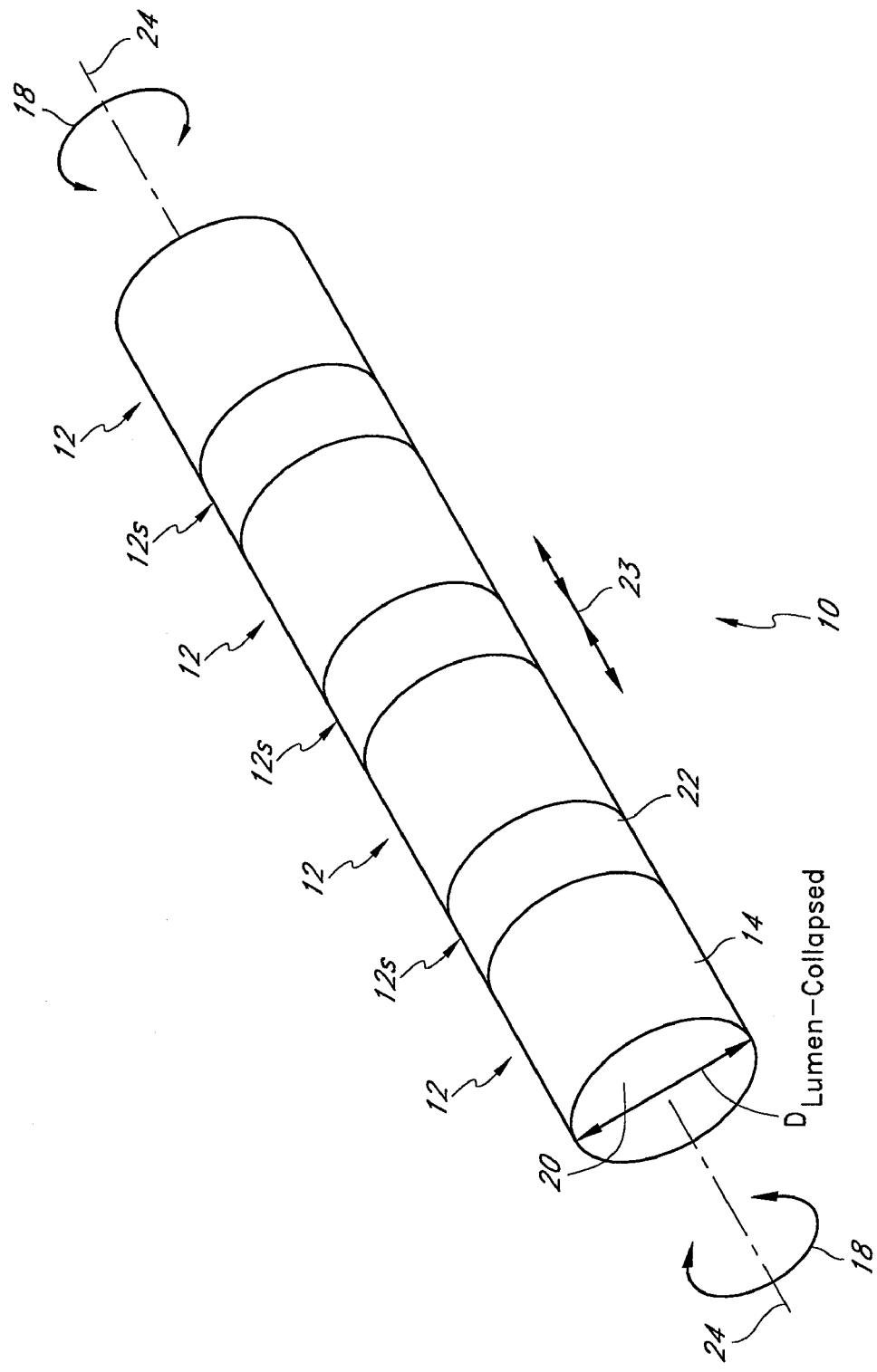
FIG. 1 is a simplified schematic perspective view of an expandable rotary circumferentially nested stent in an undeployed state illustrating features and advantages in accordance with an embodiment.

The preferred embodiments described herein relate generally to expandable medical implants for maintaining support of a body lumen and, in particular, to a diametrically expandable, rotary vascular device for enlarging an occluded portion of a vessel.

While the description sets forth various embodiments in specific detail, it will be appreciated that the description is illustrative only and should not be construed in any way as limiting the same. Furthermore, various applications of the embodiments, and modifications thereto, which can occur to those who are skilled in the art, are also encompassed by the general concepts described herein.

The term "stent" is used herein to designate embodiments for placement in (1) vascular body lumens (i.e., arteries and/or veins) such as coronary vessels, neurovascular vessels and peripheral vessels for instance renal, iliac, femoral, popliteal, subclavian and carotid; and in (2) nonvascular body lumens such as those treated currently i.e., digestive lumens (e.g., gastrointestinal, duodenum and esophagus, biliary ducts), respiratory lumens (e.g., tracheal and bronchial), and urinary lumens (e.g., urethra); (3) additionally such embodiments can be useful in lumens of other body systems such as the reproductive, endocrine, hematopoietic and/or the integumentary, musculoskeletal/orthopedic and nervous systems (including auditory and ophthalmic applications); and, (4) finally, stent embodiments can be useful for expanding an obstructed lumen and for inducing an obstruction (e.g., as in the case of aneurysms).

In the following description of embodiments, the term "stent" can be used interchangeably with the term "prosthesis" and should be interpreted broadly to include a wide variety of devices configured for supporting a segment of a body passageway. Furthermore, it should be understood that the term "body passageway" encompasses any lumen or duct within a body, such as those described herein.

Still further, it should be understood that the term "shape-memory material" is a broad term that can include a variety of known shape memory alloys, such as nickel-titanium alloys, as well as any other materials that return to a previously defined shape after undergoing substantial plastic deformation.

The term "radial strength," as used herein, describes the external pressure that a stent is able to withstand without incurring clinically significant damage. Due to their high radial strength, balloon expandable stents are commonly used in the coronary arteries to ensure patency of the vessel. During deployment in a body lumen, the inflation of the balloon can be regulated for expanding the stent to a particular desired diameter. Accordingly, balloon expandable stents can be used in applications wherein precise placement and sizing are important. Balloon expandable stents can be used for direct stenting applications, where there is no pre-dilation of the vessel before stent deployment, or in prosthetic applications, following a pre-dilation procedure (e.g., balloon angioplasty). During direct stenting, the expansion of the inflatable balloon dilates the vessel while also expanding the stent.

The stent can be fabricated from at least one or more materials. In another preferred embodiment, the stent further can comprise a tubular member formed from a biocompatible and preferably, bioresorbable polymer, such as those disclosed in co-pending U.S. application Ser. No. 10/952,202, the disclosure of which is incorporated herein in its entirety by reference. It is also understood that the various polymer formulae employed can include homopolymers and heteropolymers, which can include stereoisomersm, composites, filled materials, etc. Homopolymer is used herein to designate a polymer comprised of all the same type of monomers. Heteropolymer is used herein to designate a polymer comprised of two or more different types of monomer which is also called a co-polymer. A heteropolymer or co-polymer can be of a kind known as block, random and alternating. Further with respect to the presentation of the various polymer formulae, products according to embodiments can be comprised of a homopolymer, heteropolymer and/or a blend of such polymers.

The term "bioresorbable" is used herein to designate polymers that undergo biodegradation (through the action of water and/or enzymes to be chemically degraded) and at least some of the degradation products can be eliminated and/or absorbed by the body. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The term "inherently radiopaque" is used herein to designate polymer that is intrinsically radiopaque due to the covalent bonding of halogen species to the polymer. Accordingly, the term does not encompass a polymer which is simply blended with a halogenated species or other radiopacifying agents such as metals and their complexes.

In another preferred variation, the stent further can comprise an amount of a therapeutic agent (for example, a pharmaceutical agent and/or a biologic agent) sufficient to exert a selected therapeutic effect. The term "pharmaceutical agent", as used herein, encompasses a substance intended for mitigation, treatment, or prevention of disease that stimulates a specific physiologic (metabolic) response. The term "biological agent", as used herein, encompasses any substance that possesses structural and/or functional activity in a biological system, including without limitation, organ, tissue or cell based derivatives, cells, viruses, vectors, nucleic acids (animal, plant, microbial, and viral) that can be natural and recombinant and synthetic in origin and of any sequence and size, antibodies, polynucleotides, oligonucleotides, cDNA's, oncogenes, proteins, peptides, amino acids, lipoproteins, glycoproteins, lipids, carbohydrates, polysaccharides, lipids, liposomes, or other cellular components or organelles for instance receptors and ligands. Further the term "biological agent", as used herein, can include virus, serum, toxin, antitoxin, vaccine, blood, blood component or derivative, allergenic product, or analogous product, or arsphenamine or its derivatives (or any trivalent organic arsenic compound) applicable to the prevention, treatment, or cure of diseases or injuries of man (per Section 351(a) of the Public Health Service Act (42 U.S.C. 262(a)). Further the term "biological agent" can include 1) "biomolecule", as used herein, encompassing a biologically active peptide, protein, carbohydrate, vitamin, lipid, or nucleic acid produced by and purified from naturally occurring or recombinant organisms, tissues or cell lines or synthetic analogs of such molecules, including antibodies, growth factors, interleukins and interferons; 2) "genetic material" as used herein, encompassing nucleic acid (either deoxyribonucleic acid (DNA) or ribonucleic acid (RNA), genetic element, gene, factor, allele, operon, structural gene, regulator gene, operator gene, gene complement, genome, genetic code, codon, anticodon, messenger RNA (mRNA), transfer RNA (tRNA), ribosomal extrachromosomal genetic element, plasmagene, plasmid, transposon, gene mutation, gene sequence, exon, intron, and, 3) "processed biologics", as used herein, such as cells, tissues or organs that have undergone manipulation. The therapeutic agent can also include vitamin or mineral substances or other natural elements.

In some embodiments, the design features of the circumferentially nested elements can be varied to customize the functional features of strength, compliance, radius of curvature at deployment and expansion ratio. In some embodiments, the stent can comprise a resorbable material and vanishes when its job is done. In some embodiments, the stent serves as a therapeutic delivery platform.

Some aspects are also disclosed in co-pending U.S. patent application Ser. Nos. 11/016,269, 60/601,526, 10/655,338, 10/773,756, and 10/897,235, the disclosures of each of which are incorporated herein in their entirety by reference thereto.

Some features and arrangements of embodiments of stents are disclosed in U.S. Pat. Nos. 6,033,436, 6,224,626, and 6,623,521, each issued to Steinke, the disclosures of each of which are hereby incorporated in their entirety by reference thereto.

Some embodiments relate to an expandable stent having a plurality of longitudinally arranged sections, segments or frames. The sections can have a plurality of circumferentially nesting sliding and locking elements permitting one-way sliding, including rotating and locking and/or deforming and locking, of the elements from a collapsed diameter to an expanded/deployed diameter, but inhibiting recoil from the expanded diameter. In some embodiments, these circumferentially nested sliding and locking elements rotate, pivot and/or slide. In some embodiments, the stent can comprise a polymer and can be fabricated by a combination of laminating and laser cutting a plurality of layers.

Advantageously, the stent design elements and interlocks can be varied to customize the functional features of strength, compliance, radius of curvature at deployment and expansion ratio. In some embodiments, the stent can comprise a resorbable material and vanishes when its job is done. In some embodiments, the stent serves as a delivery platform for therapeutic agents such as pharmaceutical compounds or biological materials.

Some embodiments relate to a radially expandable stent used to open, or to expand a targeted area in a body lumen. Some embodiments relate to a radially expandable stent used as a drug delivery platform to treat vascular conditions. In some embodiments, the assembled stent can comprise a tubular member having a length in the longitudinal axis and a diameter in the radial axis, of appropriate size to be inserted into the body lumen. The length and diameter of the tubular member can vary considerably for deployment in different selected target lumens depending on the number and configuration of the structural components, described below.

The tubular member in accordance with some embodiments can have a "clear through-lumen," which can be defined as having no structural elements protruding into the lumen in either the collapsed or expanded diameters. Further, the tubular member can have smooth marginal edges to minimize the trauma of edge effects. The tubular member can be preferably thin-walled and flexible (e.g., less than about 0.01 Newtons force/millimeter deflection) to facilitate delivery to small vessels and through tortuous vasculature.

In preferred embodiments, the wall thickness can be about 0.0001 inches to about 0.0250 inches, and more preferably about 0.0010 to about 0.0100 inches. However, the wall thickness depends, at least in part, on the selected material. For example, the thickness can be less than about 0.0080 inches for plastic and degradable materials and can be less than about 0.0020 inches for metal materials. More particularly, for a 3.00 mm stent application, when a plastic material is used, the thickness can be preferably in the range of about 0.0020 inches to about 0.0100 inches. The thin walled design can also minimize blood turbulence and thus risk of thrombosis. The thin profile of the deployed tubular member in accordance with some embodiments also facilitates more rapid endothelialization of the stent. The above thickness ranges have been found to provide preferred characteristics through all aspects of the device including assembly and deployment. However, it will be appreciated that the above thickness ranges should not be limiting with respect to the scope of the embodiments and that the present teachings can be applied to devices having dimensions not discussed herein.

In some embodiments, the wall of the tubular member can comprise at least one section, which can comprise at least one sliding and locking structural element. Preferably, a plurality of sections can be connected in the longitudinal axis via linkage elements which couple at least some of the structural elements between adjacent sections. The structural elements can be configured within each section so as to generally define the circumference of the tubular member. In some embodiments, each structural element within a section can be a discrete, unitary structure. In some embodiments, the tubular member can comprise an integral unit including one or more sections with one or more structural elements. In one embodiment, each structural element can comprise one or more circumferential ribs bowed in the radial axis to form a fraction of the total circumference of the tubular member.

At least some of the structural elements can have two or more structural members and at least one articulating mechanism for providing relative motion between associated structural members. In one embodiment, the articulating mechanism can include a rotation and/or translation inducing mechanism that generates controlled stent expansion. The articulating between structural members can be such that a locking or ratcheting mechanism is formed, whereby the associated structural members and elements can slide circumferentially in one direction but can be substantially prevented from sliding circumferentially in an opposite direction. The tubular member can be adjustable from at least a first collapsed diameter to at least a second expanded diameter, but advantageously recoil to a smaller diameter can be minimized by the locking mechanism. The amount of recoil can be customized for the application by adjusting the configuration of the articulating locking mechanism. For example, one or more stops, teeth, slots or grooves and engaging elements, tabs, teeth or tongues can be incorporated into the structural components of the tubular member whereby recoil (i.e., collapse from an expanded diameter to a more collapsed diameter) can be minimized to less than about 5%.

In many of the embodiments illustrated and described herein, the intraluminal stent can be preferably provided with "slide-and-lock elements" generally referred to herein as "circumferential elements" or "circumferentially nested elements." The circumferential elements can be slidably interconnected with circumferentially adjacent elements in a manner wherein the stent exhibits mono-directional circumferential expansion from a collapsed state to an expanded state, e.g., during deployment. The circumferential elements can be preferably configured to provide a ratcheting effect such that the stent can be maintained (i.e., "locked-out") in the expanded diameter after deployment within the body passage. More particularly, the structures (e.g., circumferential elements) can flex or bend; however, in certain embodiments, unlike conventional balloon expandable stents, no substantial plastic deformation of the elements are required during expansion of the stent from a collapsed diameter to an expanded diameter. Elements of this type can be generally referred to herein as "non-deforming elements." Accordingly, the term "non-deforming element" is intended to generally describe a structure that substantially maintains its original dimensions (i.e., length and width) during deployment of the stent. Each circumferential element can be preferably formed as a flat sheet that can be cut or otherwise shaped to provide a moveable, rotatable, and/or slide-and-lock mechanism. In some embodiments, the stent can comprise "deforming elements" which preferably undergo plastic deformation during stent expansion The phrase "weaves through paired slots" can have the meaning described in U.S. Pat. Nos. 5,549,662 and 5,733,328. As used herein, this phrase describes a particular slidable coupling or articulation between stent components, wherein a portion of one stent component passes through one of a pair of slots in another stent component, and then passes back through the second of the pair of slots, creating a weave-like interlocking configuration. Preferred embodiments employ slidable couplings or articulations between stent components that avoid weave-like configurations, such that in these preferred embodiments, no portion of a stent component weaves through paired slots in another stent component.

In some embodiments, the stent preferably can comprise at least one longitudinal module, which can consist of a series of axial elements, including one or more slide-and-lock axial elements and optionally one or more passive axial elements, linked in the longitudinal axis by flexible coupling portions. Preferably, the axial elements from two or more similar longitudinal modules can be slidably connected to circumferentially adjacent axial elements. Additionally, single module (or jellyroll-type) embodiments can also be encompassed within the scope of this disclosure. For example, each module can be a discrete, unitary structure that, in some embodiments, does not stretch or otherwise exhibit any substantial permanent deformation during stent deployment.

Advantageously, some embodiments of the stent substantially can at least partially reduce or minimize overlap between the structural elements and thus can desirably reduce the effective wall thickness of the stent.

In some embodiments, at least some of the structural elements can have at least one articulating mechanism (e.g., deflecting or non-deflecting) for providing slidable engagement between adjacent circumferentially offset structural elements and/or adjacent axially offset structural elements. In one embodiment, the articulating mechanism can include a tongue and groove configuration.

Embodiments and Design Features of the Device

Figure 2:
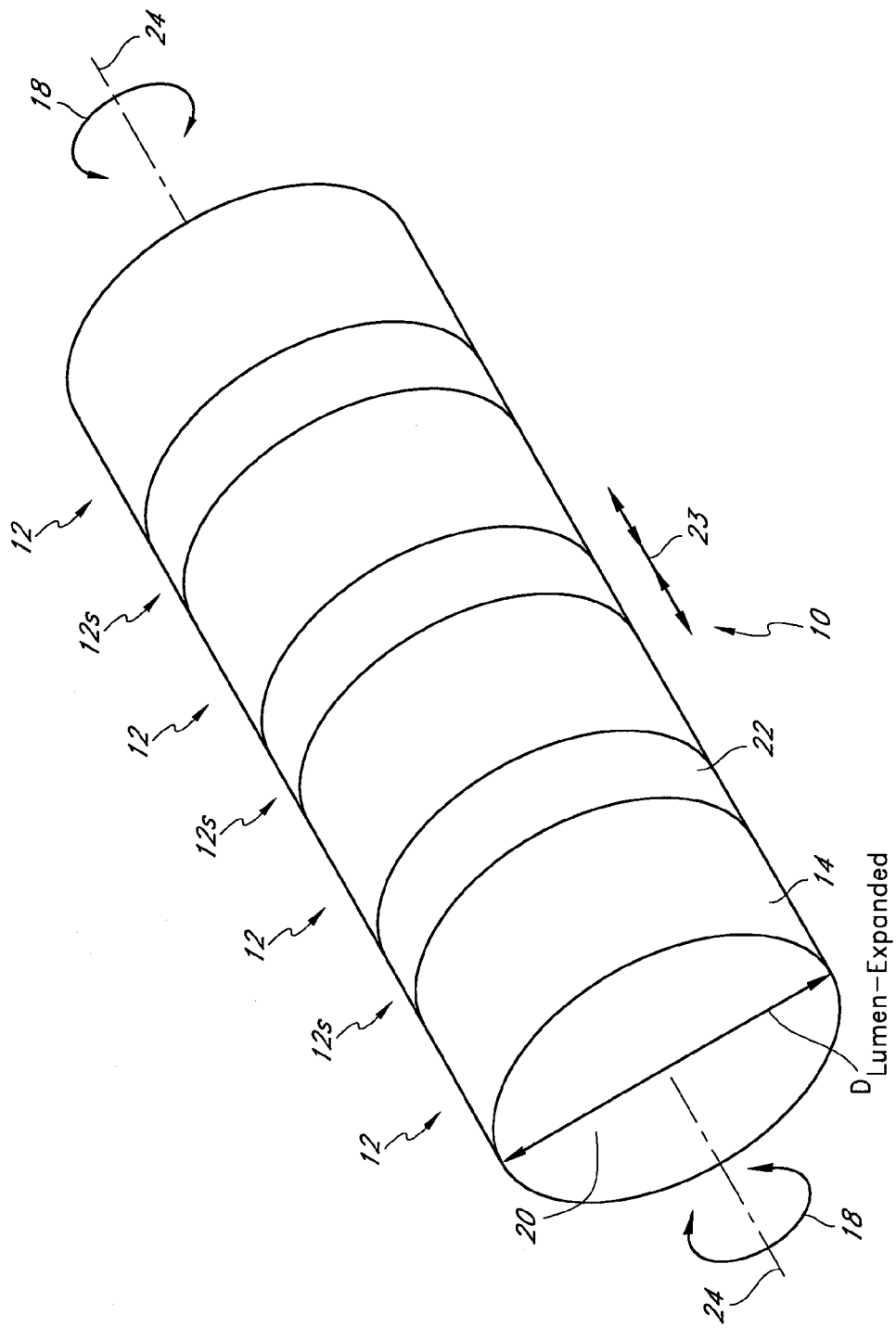
FIG. 2 is a simplified schematic perspective view of an expandable rotary circumferentially nested stent in a deployed state illustrating features and advantages in accordance with an embodiment.
Figure 3:
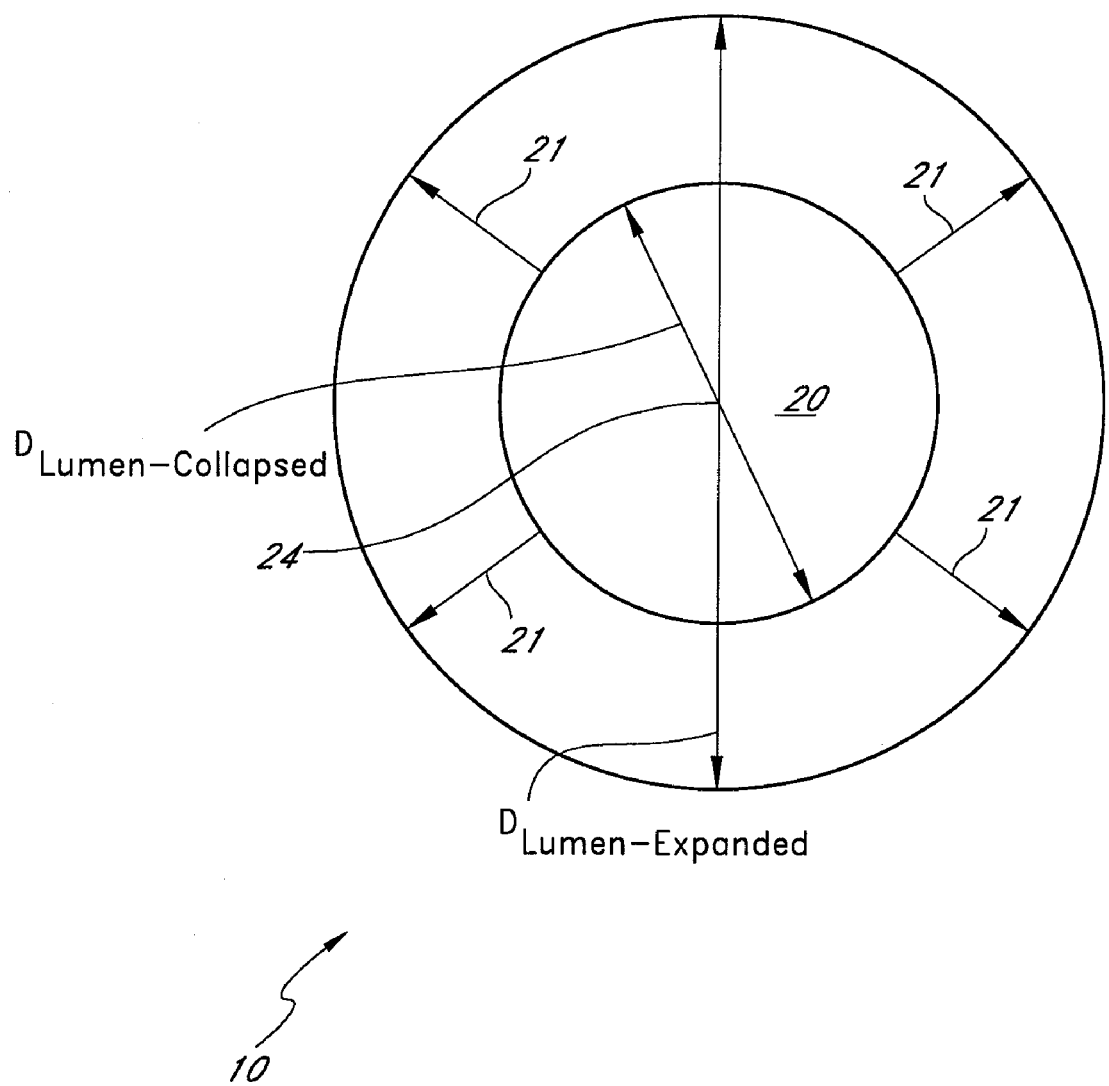
FIG. 3 is a simplified schematic end view of an expandable rotary circumferentially nested stent depicting diametric expansion and illustrating features and advantages in accordance with an embodiment.

FIGS. 1-3 show conceptual views of embodiments of an expandable vascular device, prosthesis or stent 10 in deployed and undeployed states. The stent 10 can be operative to move via rotation, translation, and/or slide and lock movement. These drawings are intended to be conceptual in nature and certain embodiments of the stent and its structural elements, structural members, slide and lock mechanisms and other features are discussed in further detail below with reference to further drawings as described in further detail herein.

Referring in particular to FIGS. 1-3 for now, the stent 10 can have a tubular form with a wall comprising a plurality of generally longitudinally arranged linked circumferential sections, segments or frames 12 and 12s. The stent 10 can have a through lumen 20 which, along with the stent itself, can be expandable from a first diameter ($D_{lumen\text{-}collapsed}$ or $D_{inner\text{-}collapsed}$) to a second diameter ($D_{lumen\text{-}expanded}$ or $D_{inner\text{-}expanded}$). The stent 10 and/or the lumen 20 can have a generally longitudinal axis 24.

The stent 10 can comprise alternatingly arranged sections 12 and flexible sections 12s. The section 12 can be operative to move via rotation, translation, and/or slide and lock movement. Each section 12 can include one or more expandable structural elements 14 that can have articulating and/or ratcheting mechanisms (as discussed in more detail below) to facilitate controlled stent expansion while minimizing recoil. The number of structural elements in a section 12 and/or the number of sections 12 in the stent 10 can be efficaciously varied and selected, as needed or desired.

Each flexible section 12s can include a plurality of linkage elements 22 and connects adjacent stent sections 12. One or more of the linkage elements 22 can comprise spring elements. The spring elements 22 provide flexibility and allow expansion of the flexible sections 12s along with stent expansion. The spring elements 22 also allow for rotary and/or axial deflection of members of the structural elements 14 during stent expansion to a deployed state. The spring elements 22 facilitate this deflection by providing a resilient biasing mechanism to achieve substantially elastic deflection or deformation. The number of linkage elements in a flexible section and/or the number of flexible sections in a stent can be efficaciously varied and selected, as needed or desired.

During stent expansion, there can be circumferential motion (as generally indicated by arrows 18) and diametric expansion (as generally indicated by arrows 21) from a collapsed diameter ($D_{lumen\text{-}collapsed}$ or $D_{inner\text{-}collapsed}$) to an expanded diameter ($D_{lumen\text{-}expanded}$ or $D_{inner\text{-}expanded}$). In certain embodiments there can also be axial or longitudinal motion of some of the stent elements and/or members that can be generally parallel to the stent axis 24 (as generally indicated by arrows 23).

In one embodiment, $D_{lumen\text{-}collapsed}$ or $D_{inner\text{-}collapsed}$ can be in the range from about 0.812 mm (0.032 inches) to about 0.914 mm (0.036 inches), including all values and sub-ranges therebetween. In one embodiment, $D_{lumen\text{-}expanded}$ or $D_{inner\text{-}expanded}$ can be in the range from about 2.0 mm (0.07874 inches) to about 8.0 mm (0.315 inches), including all values and sub-ranges therebetween. In modified embodiments, $D_{lumen\text{-}collapsed}$ and/or $D_{lumen\text{-}expanded}$ can have other suitable values with efficacy, as needed or desired.

At full expansion, a capture mechanism can be provided to limit further stent expansion. Each section 12 can comprise one or more capture mechanisms such as, but not limited to, hard stops, straps, overhanging elements, covers, tongue-groove configurations and other suitable geometries or devices that prevent further stent expansion. This desirably serves to control and limit the stent diameter to a predetermined deployment diameter.

Circle Link Stent Embodiments

Figure 4:
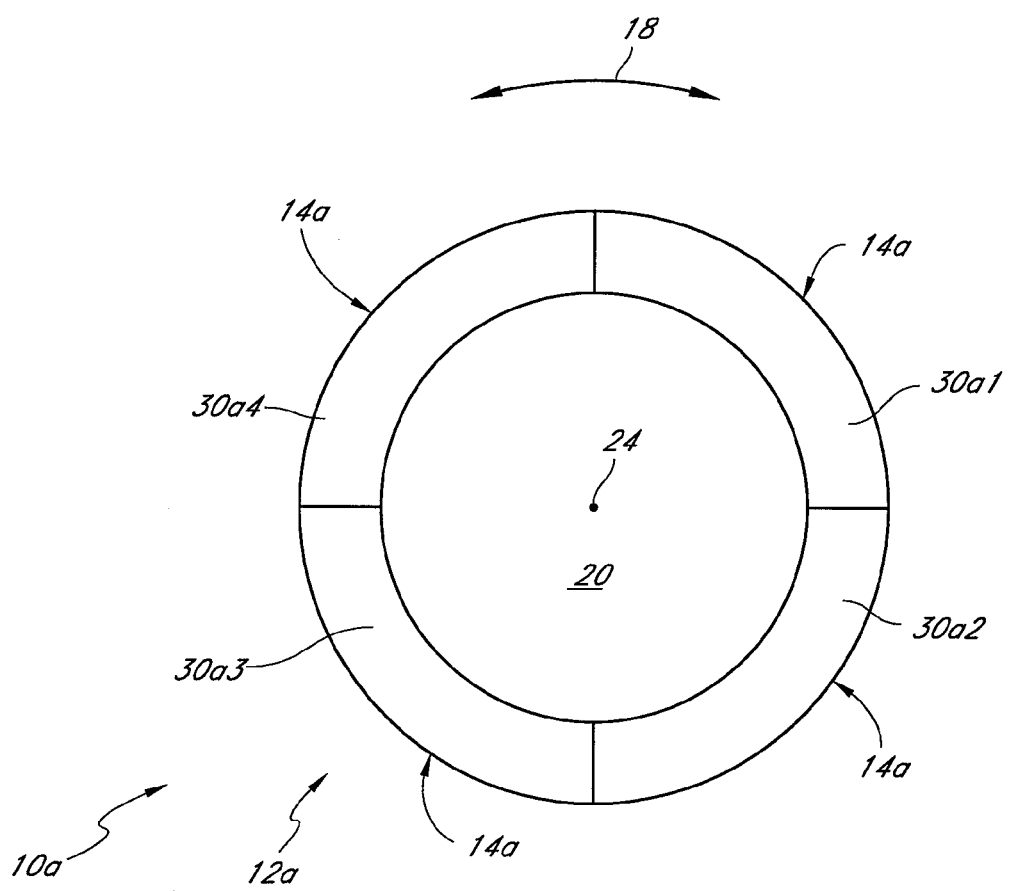
FIG. 4 is a simplified end view of a circle link expandable rotary circumferentially nested stent in a nested state illustrating features and advantages in accordance with an embodiment.
Figure 5:
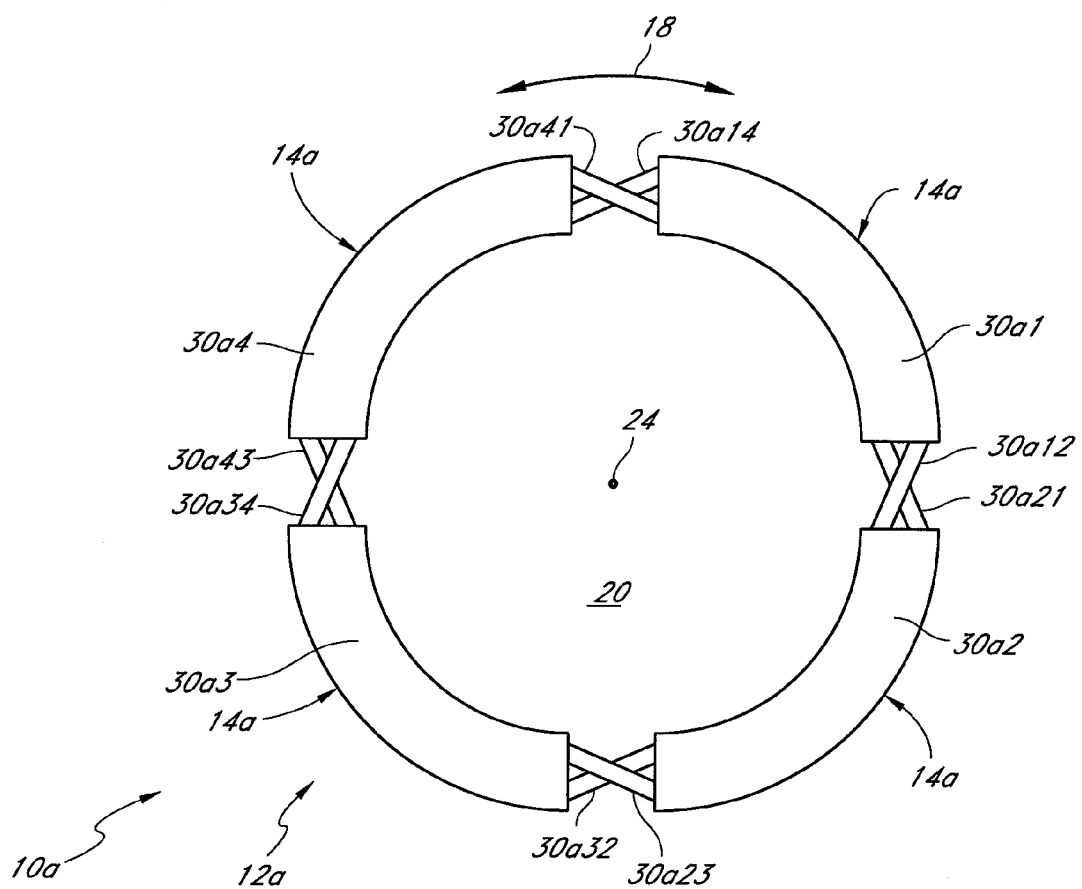
FIG. 5 is a simplified end view of the circle link stent of FIG. 4 in an expanded state illustrating features and advantages in accordance with an embodiment.

FIGS. 4-7 show different views of embodiments of an expandable, rotating and translating, vascular device, prosthesis or stent 10a. FIG. 4 shows an end view of the stent 10a in an undeployed state, and FIG. 5 shows an end view of the stent 10a shown in FIG. 4 in a deployed state. The stent 10a can have an expandable lumen 20 and a longitudinal axis 24, and the circumferential expansion can be generally denoted by arrows 18.

The stent 10a can have one or more sections, segments or frames 12a with each section comprising one or more circumferentially nested expandable structural elements 14a that can have articulating and/or ratcheting mechanisms (as discussed in more detail below) to facilitate controlled stent expansion while minimizing recoil. Typically, a plurality of stent sections 12a can be axially or longitudinally arranged to form the stent 10a. In some embodiments, adjacent stent sections 12a can be linked or connected by flexible sections 12s which, in some embodiments, comprise one or more spring elements 22, as discussed further below.

In the illustrated embodiment of FIGS. 4 and 5, the stent section 12a can comprise four circumferentially nested structural elements 14a. In modified embodiments, each stent section can efficaciously comprise fewer or more structural elements, as needed or desired.

As shown in FIG. 4, each structural element 14a generally can comprise a substantially curved or semi-circular bar, member, rib, rod or ring element "30aN" (such as 30a1, 30a2, 30a3, 30a4, for the embodiment illustrated in FIGS. 4-5, where N equals 1, 2, 3, or 4) connected, coupled or articulated with a plurality of relatively short links, bars, rods, members or ribs "30aNM" (such as 30a12, 30a14, 30a21, 30a23, 30a32, 30a34, 30a41, 30a43, shown in FIG. 5, where M equals 1, 2, 3, or 4) which rotate and/or translate to provide stent expansion. In one embodiment, the total number of links 30aNM can be eight with two connecting adjacent ring elements 30aN, though in modified embodiments, fewer or more ring links can be utilized with efficacy, as needed or desired. For example, only one ring link can connect adjacent ring elements 30aN.

As best seen in FIG. 5, the ring element 30a1 can be connected to links 30a12, 30a21 and 30a14, 30a41; the ring element 30a2 can be connected to links 30a12, 30a21 and 30a23, 30a32; the ring element 30a3 can be connected to links 30a23, 30a32 and 30a34, 30a43; and the ring element 30a4 can be connected to links 30a34, 30a43 and 30a14, 30a41.

Figure 6:
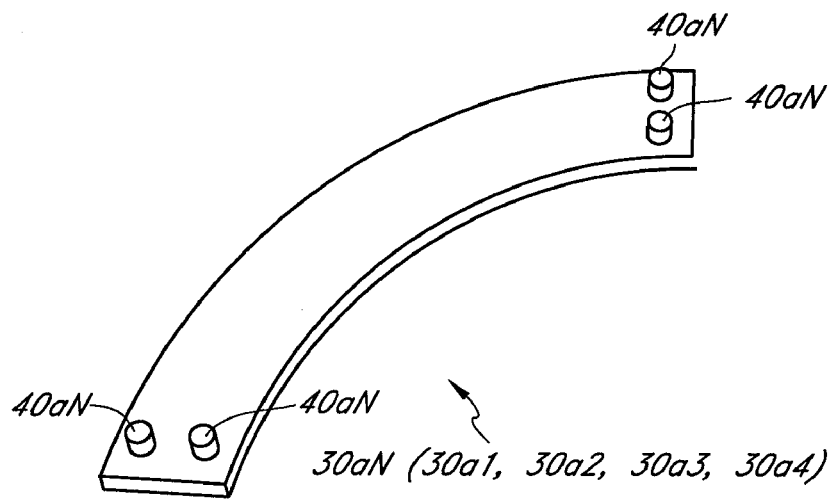
FIG. 6 is a simplified perspective view of a structural element ring of the stent of FIGS. 4 and 5 illustrating features and advantages in accordance with an embodiment.

As shown in FIG. 6, each ring element 30aN can comprise, on one of its surfaces, a pair of spaced protrusions or male members or elements 40aN proximate or adjacent one end and a second pair of spaced protrusions or male members or elements 40aN proximate or adjacent an opposite end. The male members 40aN can efficaciously comprise an axel, pop rivet, pivot pin, pawl or the like, among others, as needed or desired.

Figure 7:
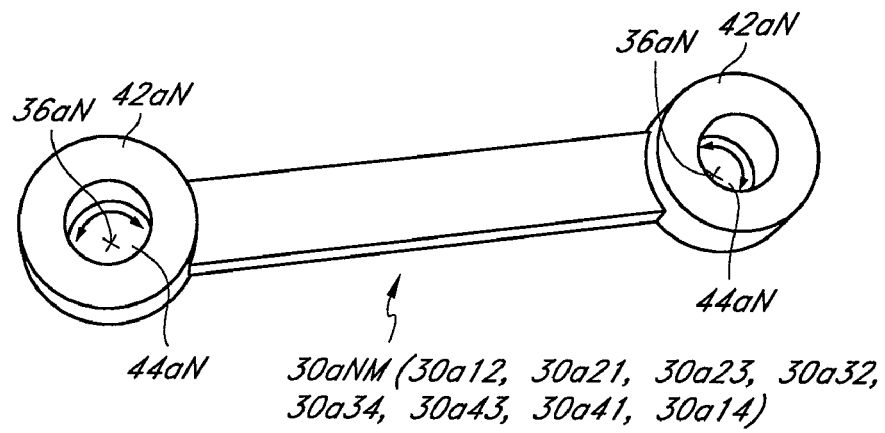
FIG. 7 is a simplified perspective view of a structural element link of the stent of FIGS. 4 and 5 illustrating features and advantages in accordance with an embodiment.

As shown in FIG. 7, each link element 30aNM can comprise a generally cylindrical ring or female member 42aN at one end and another generally cylindrical ring or female member 42aN at an opposite end. Each of the female members 42aN can comprise an internal female hole, opening, cavity or port 44aN which mates with a corresponding one of the male members 40aN and receives it therein. Of course, alternative articulation structures known in the art, besides the male and female structures illustrated in FIGS. 6-7, can be used in other embodiments, as long as the articulation structure allows for rotation.

As discussed further below, the male and female members 40aN and 42aN can be configured to interact such as to permit motion or rotation (e.g., about rotation axis 36aN) in one direction only to allow for stent expansion to the desired maximum diameter. This can include, but is not limited to, a hinge, ratchet, pawl or other articulation system or mechanism which can employ teeth, detents, spring members and the like.

Figure 8:
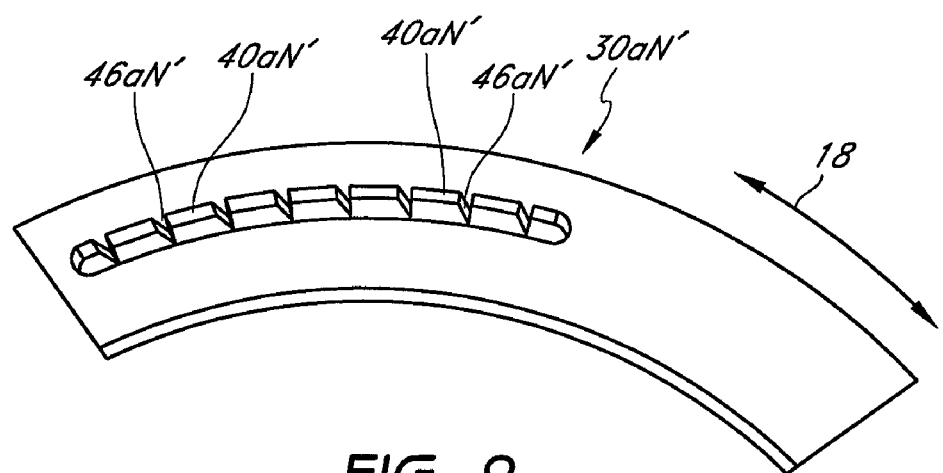
FIG. 8 is a simplified perspective view of a structural element ring of the stent of FIGS. 4 and 5 illustrating features and advantages in accordance with another embodiment.
Figure 9:
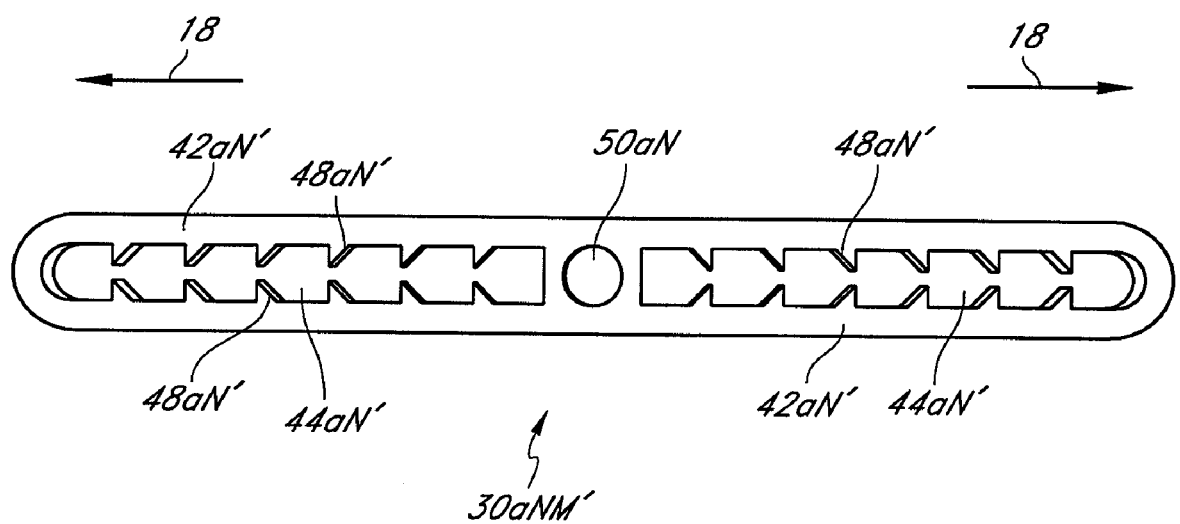
FIG. 9 is a simplified planar view of a structural element link or slotted rod of the stent of FIGS. 4 and 5 illustrating features and advantages in accordance with another embodiment.

FIGS. 8 and 9 show other embodiments of a structural element ring 30aN' and of a structural element link or slotted rod 30aNM' of the circular link stent 10a. One or more ring elements 30aN' can be connected, coupled or articulated with corresponding one or more slotted rods 30aNM' to form one or more circumferentially nested structural elements which can be part of the overall stent 10a.

The structural element ring 30aN' generally can comprise a plurality of teeth, protrusions or male members or elements 40aN'. The teeth 40aN' can be spaced by a corresponding generally V-shaped slots 46aN' or the like.

The structural element link or slotted rod 30aNM' can comprise a pair of spaced female members or elements 42aN' as shown in FIG. 9. Each of the female members 42aN' can comprise an internal slot 44aN' comprising a plurality of teeth or protrusions 48aN'. Each female member 42aN' can be connected to a respective ring element 30aN'. More particularly, the teeth 40aN' of respective ring elements 30aN' can be received within respective internal slots 48aN' to form an articulating and/or ratcheting mechanisms to facilitate controlled stent expansion while minimizing recoil. The circumferential stent expansion can be generally denoted by arrows 18. Further, the structural element link or slotted rod 30aNM' can also comprise an opening, hole or port 50aN' which can be typically connected, attached or coupled to a male element or protrusion of a ring element 30aN or 30aN'.

Figure 10:
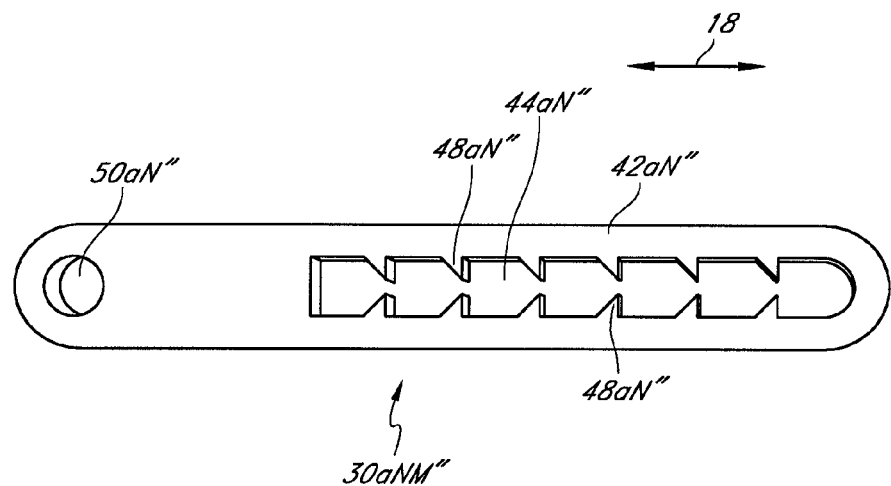
FIG. 10 is a simplified planar view of a structural element link or slotted rod of the stent of FIGS. 4 and 5 illustrating features and advantages in accordance with yet another embodiment.

FIG. 10 shows another embodiment of a structural element link or slotted rod 30aNM" of the circular link stent 10a configured to articulate with the structural element ring 30aN'. One or more ring elements 30aN or 30aN' can be connected, coupled or articulated with corresponding one or more slotted rods 30aNM" to form one or more circumferentially nested structural elements which can be part of the overall stent 10a. In some embodiments, structural element link or slotted rod 30aNM" can be used with the ring element 30aN of FIG. 6.

The structural element link or slotted rod 30aNM" can comprise a female member or element 42aN". The female member 42aN" can comprise an internal slot 44aN" comprising a plurality of teeth or protrusions 48aN". The female member 42aN" can be connected to a respective ring element 30aN'. More particularly, the teeth 40aN' of respective ring elements 30aN' can be received within the internal slot 48aN' to form an articulating and/or ratcheting mechanisms to facilitate controlled stent expansion while minimizing recoil.

An opposing end of the structural element link or slotted rod 30aNM" can comprise an opening, hole or port 50aN" which can be typically connected, attached or coupled to a male element or protrusion of a ring element 30aN or 30aN'. This coupling can comprise a fixed attachment or it can comprise an articulating and/or ratcheting mechanism with efficacy, as needed or desired. The circumferential stent expansion can be generally denoted by arrows 18.

Point Lock Stent Embodiments

Figure 11:
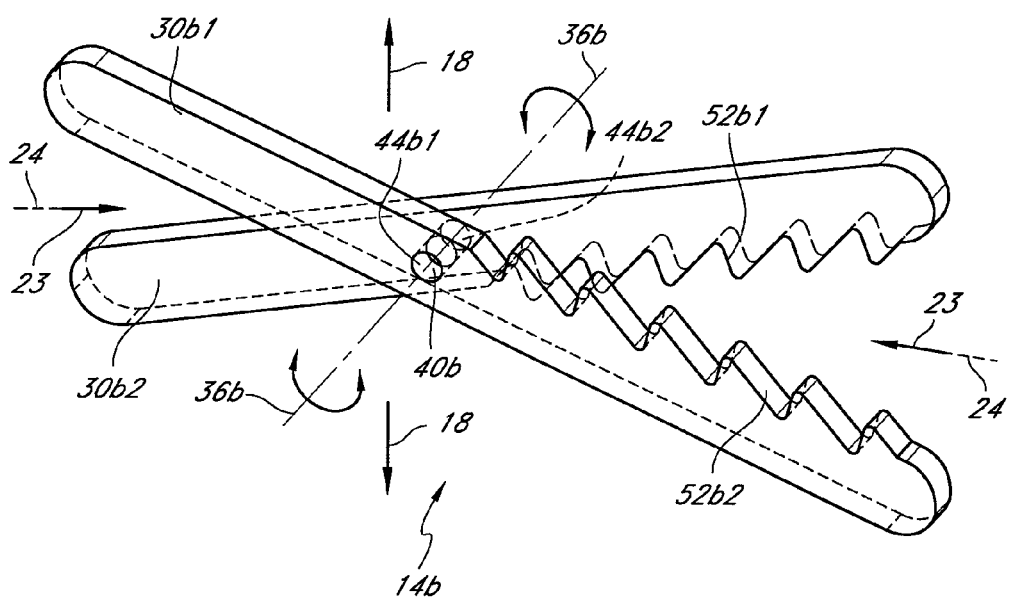
FIG. 11 is a simplified perspective planar view of a point lock structural element of an expandable rotary circumferentially nested stent illustrating features and advantages in accordance with an embodiment.

FIG. 11 shows a circumferentially nested structural element 14b of a stent section, segment or frame in accordance with certain embodiments. Typically, a plurality of these structural elements 14b can be circumferentially and axially arranged to form, in some embodiments, an expandable, circumferentially nested, rotating and translating, vascular device, prosthesis or stent.

The structural element 14b generally can comprise two rotatable and connected bars, members, elements or ribs 30b1 and 30b2. The bars 30b1 and 30b2 comprise respective internal aligned holes, openings, cavities, ports or female members or elements 44b1 and 44b2 which also generally define the location of a rotation axis 36b. A protrusion or male member or element 40b extends through these female openings 44b1 and 44b2. The male member 40b can efficaciously comprise an axel, pop rivet, pivot pin, pawl or the like, among others, as needed or desired. As discussed further below, the male member 40b can receive corresponding female members 44b1 and 44b2 to form an articulating and/or ratcheting mechanism to facilitate controlled stent expansion while minimizing recoil. The articulating and/or ratcheting mechanism can be a hinge, ratchet and pawl mechanism or the like to permit motion or rotation in one direction only.

Each of the bars 30b1 and 30b2 further can comprise a plurality of respective teeth, lock detents or stops 52b1 and 52b2. The teeth 52b1 and 52b2 can be sized, configured and arranged in a predetermined manner so that after a given circumferential expansion (as generally illustrated by arrows 18) of the structural element 14b a pair of opposing teeth 52b1 and 52b2 interlock or contact or reach a stage or "point of lock" to prevent recoil. The number, geometry, arrangement and/or configuration of these teeth can be efficaciously varied, as needed or desired.

The point of lock and/or the ratchet and pawl mechanism can therefore tend to minimize recoil. In some embodiments, capture mechanisms such as, but not limited to, hard stops, straps, overhanging elements, covers, tongue-groove configurations and other suitable geometries or devices can be utilized with efficacy to limit further stent expansion, as needed or desired.

The axial or longitudinal motion of the structural element 14b can be generally denoted by the arrows 23. In this case, the length of the structural element 14b decreases in size as the structural element 14b and stent expand. However, if linkage elements, such as spring or flexible sections 12s are utilized, they can compensate for this reduction in local structural element length and preserve the overall stent length.

Ratchet Configuration Embodiments

Figure 12:
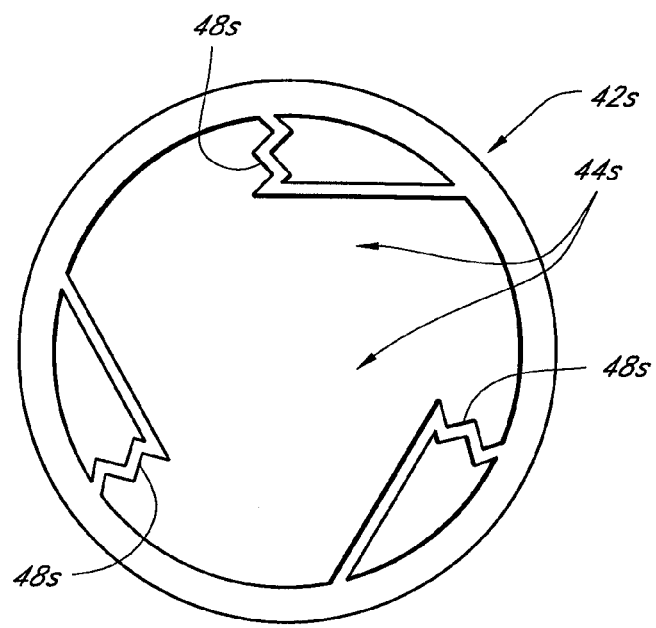
FIG. 12 is a simplified end view of a spring-loaded female ratchet member or element of a ratchet system of an expandable rotary circumferentially nested stent illustrating features and advantages in accordance with an embodiment.

FIG. 12 shows a radial female ratchet member or element 42s of one embodiment of a ratchet system for use in conjunction with certain embodiments of an expandable, circumferentially nested, rotating and translating, vascular device, prosthesis or stent. The female ratchet member 42s can comprise an internal or inner lumen, hole, opening or port 44s which receives a male ratchet element or member to provide a ratcheting and/or articulating mechanism which facilitates stent expansion. The male member can efficaciously comprise an axel, pop rivet, pivot pin, pawl or the like, among others, as needed or desired.

The female ratchet member 42s can be shaped like an annular cylinder or ring with a generally circular outer surface and an generally circular inner surface from which a plurality of internal teeth 48s that extend into the lumen or hole 44s. The teeth or spring members or elements 48s can comprise springs or a flexible or plastically deformable material to provide a ratcheting mechanism.

In some embodiments, the female spring ratchet member 42s can be positioned within the holes 44aN of the stent links 30aNM illustrated in FIG. 7, the hole 50aN' of the stent link 30aNM' illustrated in FIG. 9, or the holes 50aN" of the stent link 30aNM" illustrated in FIG. 10, for example. For instance, respective female spring ratchet members 42s can be fitted within the holes 44aN of the stent links 30aNM or they can be an integral part of the stent links 30aNM or any combination thereof with efficacy, as needed or desired. If not integrally formed with the stent links 30aNM, the female spring ratchet members 42s should be rigidly affixed, attached, or adhered to within the holes 44aN in order to mitigate any rotation of the female spring ratchet member 42s within the holes 44aN. In some embodiments, the female end members 42aN of the stent links or bars 30aNM can be comprised of the female spring ratchet members 42s.

Figure 13:
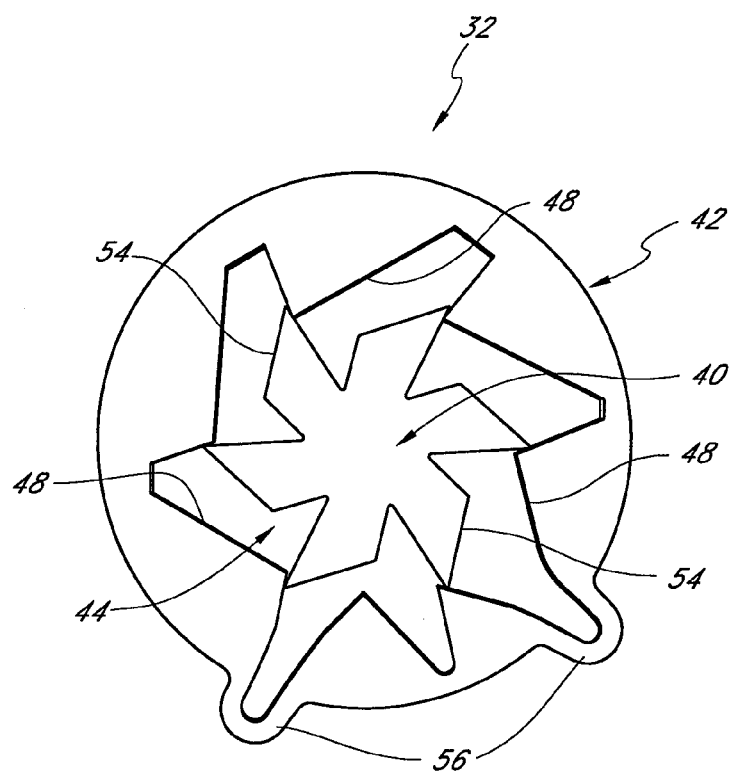
FIG. 13 is a simplified end view of a ratchet system of an expandable rotary circumferentially nested stent illustrating features and advantages in accordance with an embodiment.

FIG. 13 shows an end view of a radial internal ratchet system 32 comprising a radial female ratchet member 42 and a radial male ratchet member 40 for use in conjunction with certain embodiments of an expandable, circumferentially nested, rotating and translating, vascular device, prosthesis or stent.

Figure 14:
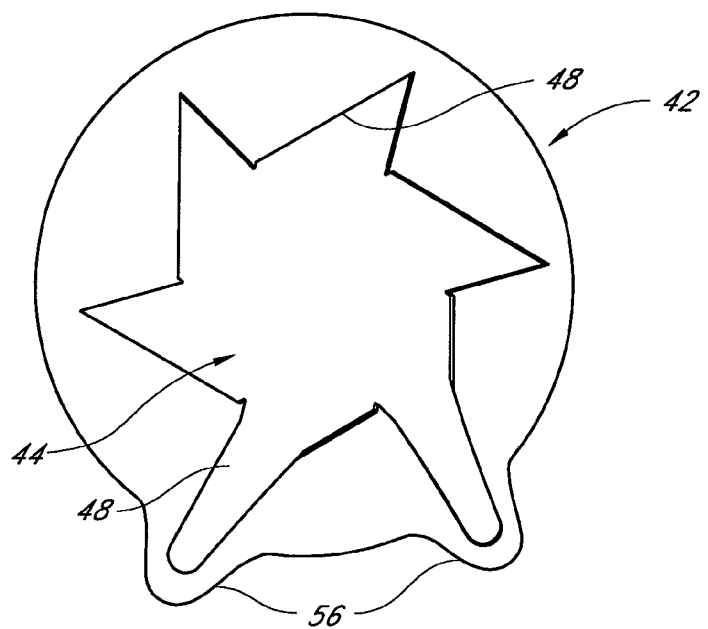
FIG. 14 is a simplified end view of a female ratchet member or element of the ratchet system of FIG. 13 illustrating features and advantages in accordance with an embodiment.
Figure 15:
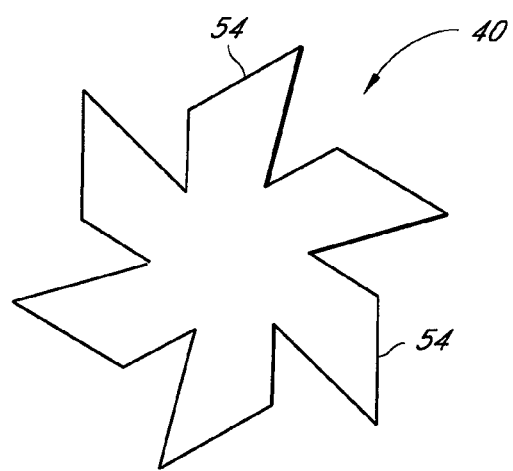
FIG. 15 is a simplified end view of a male ratchet member or element of the ratchet system of FIG. 13 illustrating features and advantages in accordance with an embodiment.

As seen in FIGS. 13-14, the female ratchet member 42 can comprise an internal or inner lumen, hole, opening or port 44 which receives the male ratchet member 40 to provide a ratcheting and/or articulating mechanism which facilitates stent expansion. Referring to FIG. 15, the male ratchet member 40 can efficaciously comprise an axel, pop rivet, pivot pin, pawl or the like, among others, as needed or desired. As also mentioned above, the female ratchet member 42 can be shaped like an annular cylinder or ring with a generally circular outer surface and an generally circular inner surface from which a plurality of internal female teeth 48 that extend into the lumen or hole 44. The internal female teeth 48 can comprise plastically deformable or non-deformable material that ratchet with plastically deformable or non-deformable male teeth 54 to provide a ratcheting mechanism. Additionally, the female ratchet member 42 can be formed to include joints 56 that allow stretching and movement of the internal female teeth 48. The joints 56 can be provided in addition to or alternatively to the use of plastically deformable material, as mentioned above. As shown in FIG. 15, the male ratchet member 40 can comprise a generally cylindrical body portion with male teeth 54 extending therefrom.

As mentioned above, in some embodiments, the female spring ratchet member 42 can be positioned within the holes 44aN of the stent links 30aNM illustrated in FIG. 7, the hole 50aN' of the stent link 30aNM' illustrated in FIG. 9, or the holes 50aN" of the stent link 30aNM" illustrated in FIG. 10, for example. For instance, respective female ratchet members 42 can be fitted within the holes 44aN of the stent links 30aNM or they can be an integral part of the stent links 30aNM or any combination thereof with efficacy, as needed or desired. In some embodiments, female ratchet members 42 can comprise the female end members 42aN of the stent links or bars 30aNM.

In some embodiments, the male ratchet members 40 comprise the male protrusions 40aN of the stent rings or bars 30aN of FIG. 6. For example, the male ratchet members 40 can be attached or connected to the stent ring 30aN, or alternatively, the male ratchet members 40 can be an integral part of the stent rings 30aN, or any combination thereof with efficacy, as needed or desired.

Figure 19:
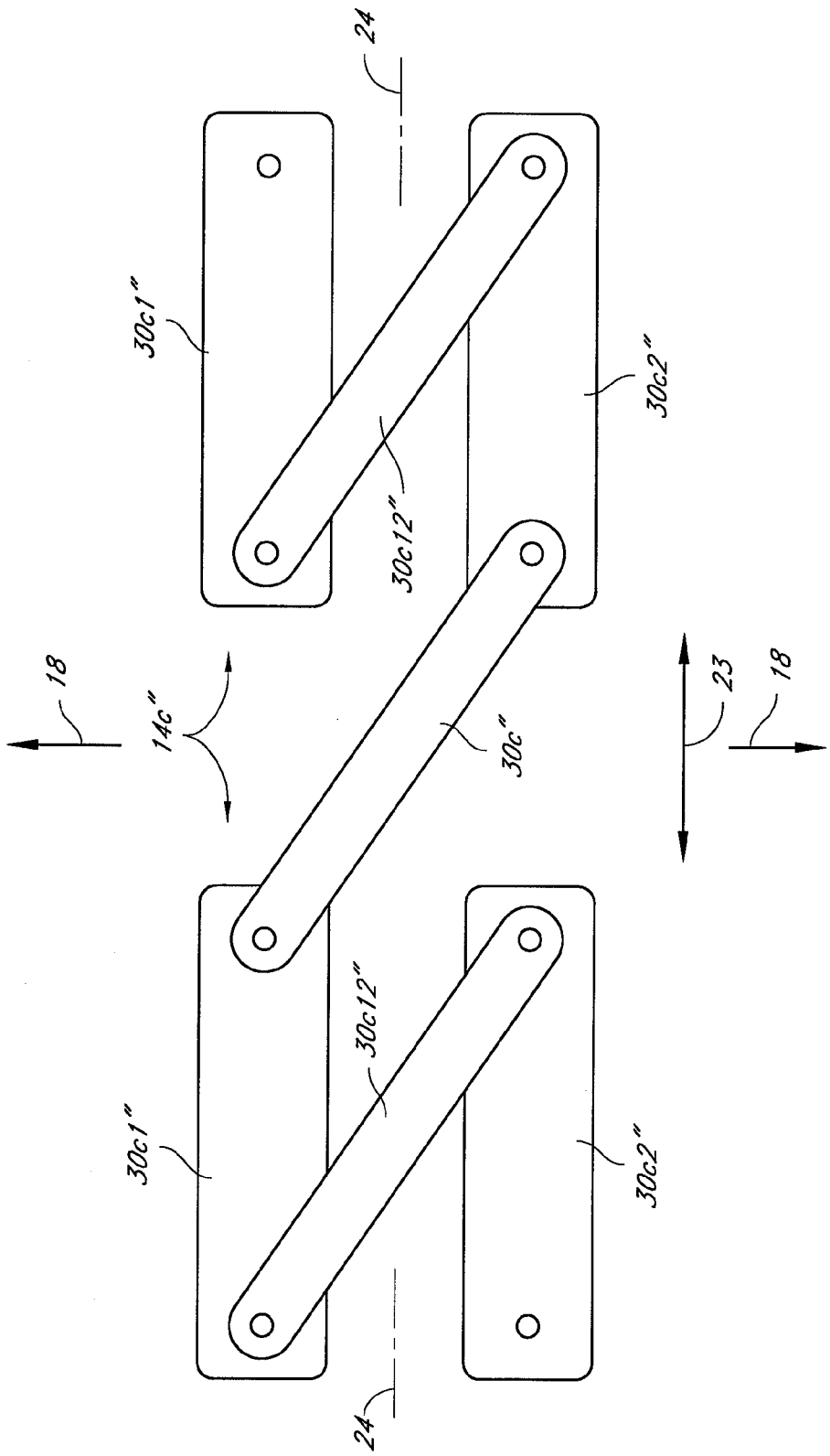
FIG. 19 is a simplified schematic planar partial view of an expandable rotary circumferentially nested three-bar linkage stent illustrating features and advantages in accordance with an embodiment.
Figure 22:
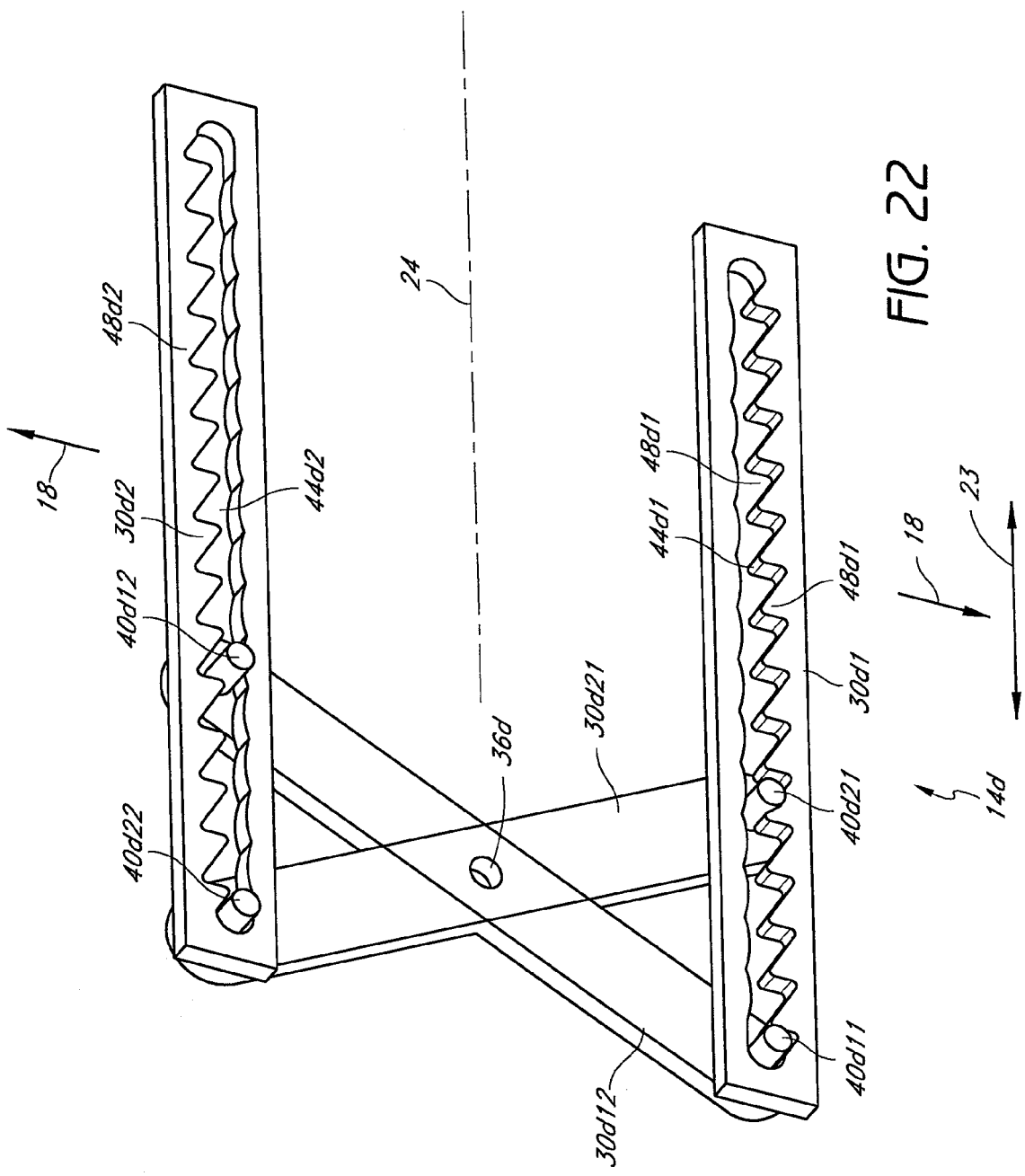
FIG. 22 is a simplified planar view a four-bar linkage structural element of an expandable rotary circumferentially nested stent in a partially expanded or collapsed state illustrating features and advantages in accordance with an embodiment.
Figure 23:
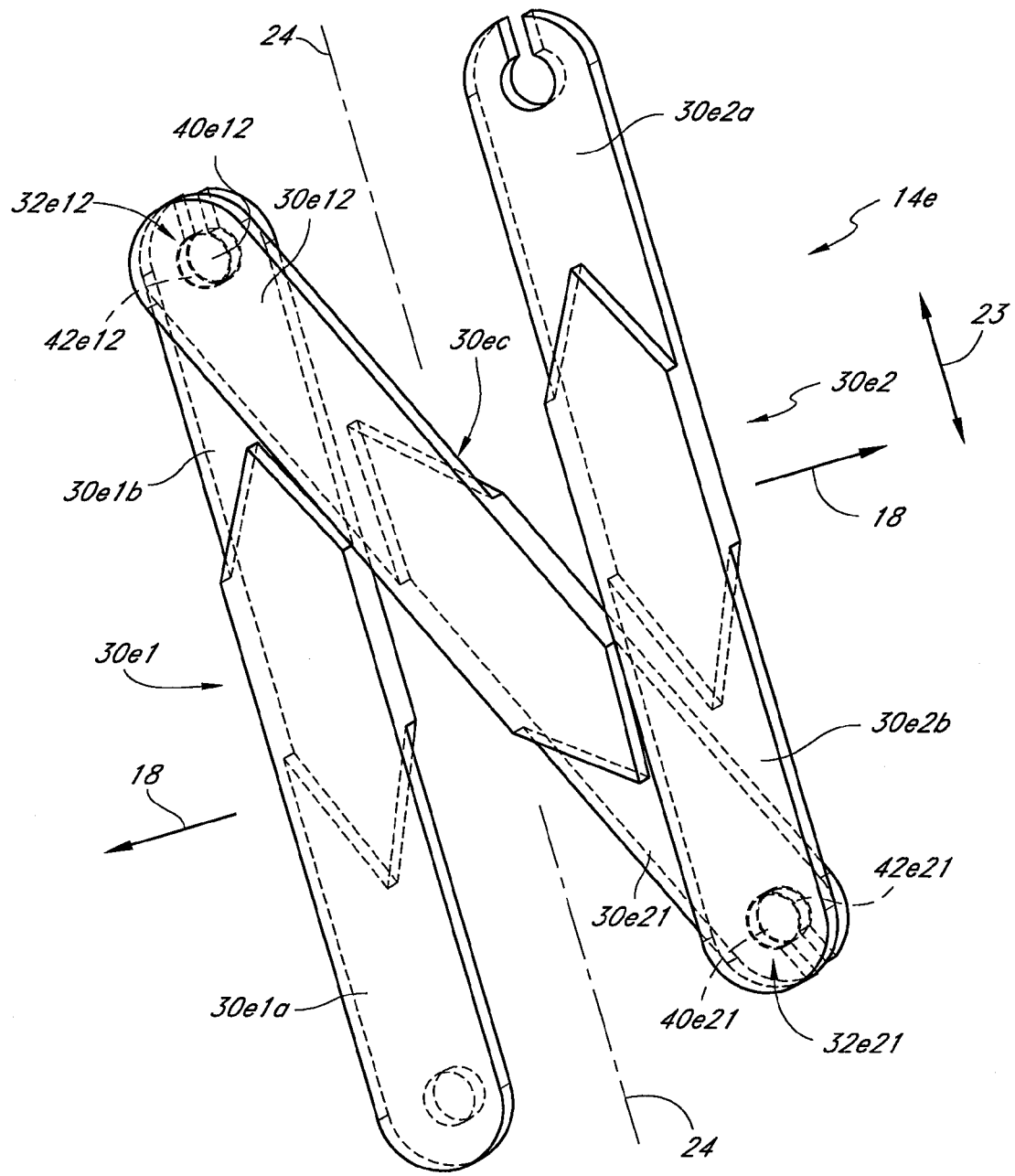
FIG. 23 is a simplified planar perspective view of a ball and socket structural element of an expandable rotary circumferentially nested stent illustrating features and advantages in accordance with an embodiment.

Furthermore, in other embodiments, the ratchet system embodiments of FIGS. 12-15 can be efficaciously used in conjunction with various embodiments disclosed herein, such as embodiments of the circumferentially nested two-link structural elements of FIG. 11, embodiments of the circumferentially nested three-bar structural elements of FIG. 19, embodiments of the circumferentially nested three-bar structural elements of FIG. 22, and embodiments of the ball and sock structural element of FIG. 23, to name a few. For example, these can be used or positioned around the general location of the rotation axis to provide a ratcheting mechanism in such embodiments.

During structural element or stent expansion, the female ratchet teeth 48 (48s) and/or the male ratchet teeth 54 permit one way relative rotation and motion between the ratcheting members 42 and 40, thereby permitting rotation in one direction only between and hence desirably allowing stent expansion and minimizing undesirable contraction and recoil. Advantageously, in some embodiments, the use of internal female teeth 48 (48s) can provide support and protection for the internal male ratchet teeth 54 and mitigate undesirable motion, thereby facilitating optimum performance.

Three-Bar Linkage Stent Embodiments

FIGS. 16 and 17 show linkage sections, segments or frames 12c in respective collapsed and deployed states in accordance with some embodiments of an expandable rotary circumferentially nested three-bar linkage vascular device, prosthesis or stent. Each section 12c can comprise one or more structural elements such as structural elements 14c1 and 14c2. As indicated above and herein, typically, a plurality of structural elements can be circumferentially and axially arranged to form, in some embodiments, an expandable, circumferentially nested, rotating and translating, vascular device, prosthesis or stent.

The linkage sections and/or structural elements 12c can be three-bar linkage sections and can be axially or longitudinally linked by spring or flexible sections, segments or frames 12s. FIG. 16 illustrates a single three-bar linkage sections and/or structural elements 12c in a non-expanded state, while FIG. 17 illustrates a plurality of three-bar linkage sections and/or structural elements 12c in an expanded state. Additionally, as shown in FIG. 17, each spring or flexible section, segment or frame 12s can also comprise one or more spring or flexible elements 22. The longitudinal or axial axis can be generally depicted by 24. The stent expansion can be generally depicted by arrows 18.

As shown in FIGS. 16-17, the three-bar linkage structural element 14c1 generally can comprise three bars, members, ribs or elements 30c1, 30c3 and 30c13 and the three-bar linkage structural element 14c2 generally can comprise three bars, members, ribs or elements 30c2, 30c3 and 30c23. The common or shared bar 30c3 can connect the structural elements 14c1 and 14c2 such that they and their corresponding bars can be circumferentially nested and allow one-way sliding circumferential stent expansion. Although the embodiment of FIGS. 16-17 illustrates the use of only three, more than three bars, members, ribs or elements 30cN can be used; in fact, as many bars, members, ribs or elements 30cN as necessary can be employed to achieve a desired expansion ratio. Further, the bars, members, ribs or elements 30cN are preferably oriented parallel with respect to each other, and can be oriented generally parallel with respect to the longitudinal axis 24 of the stent 10.

During stent expansion, the central bars 30c13 and 30c23 translate in both the circumferential direction 18 (and also circumferentially push the end bars 30c1, 30c2) and longitudinal direction 23 to provide stent expansion. Typically, a plurality of these structural elements 14c1 and 14c2 can be circumferentially and axially arranged to form, in some embodiments, an expandable, circumferentially nested, rotating and translating, vascular device, prosthesis or stent.

Figure 18:
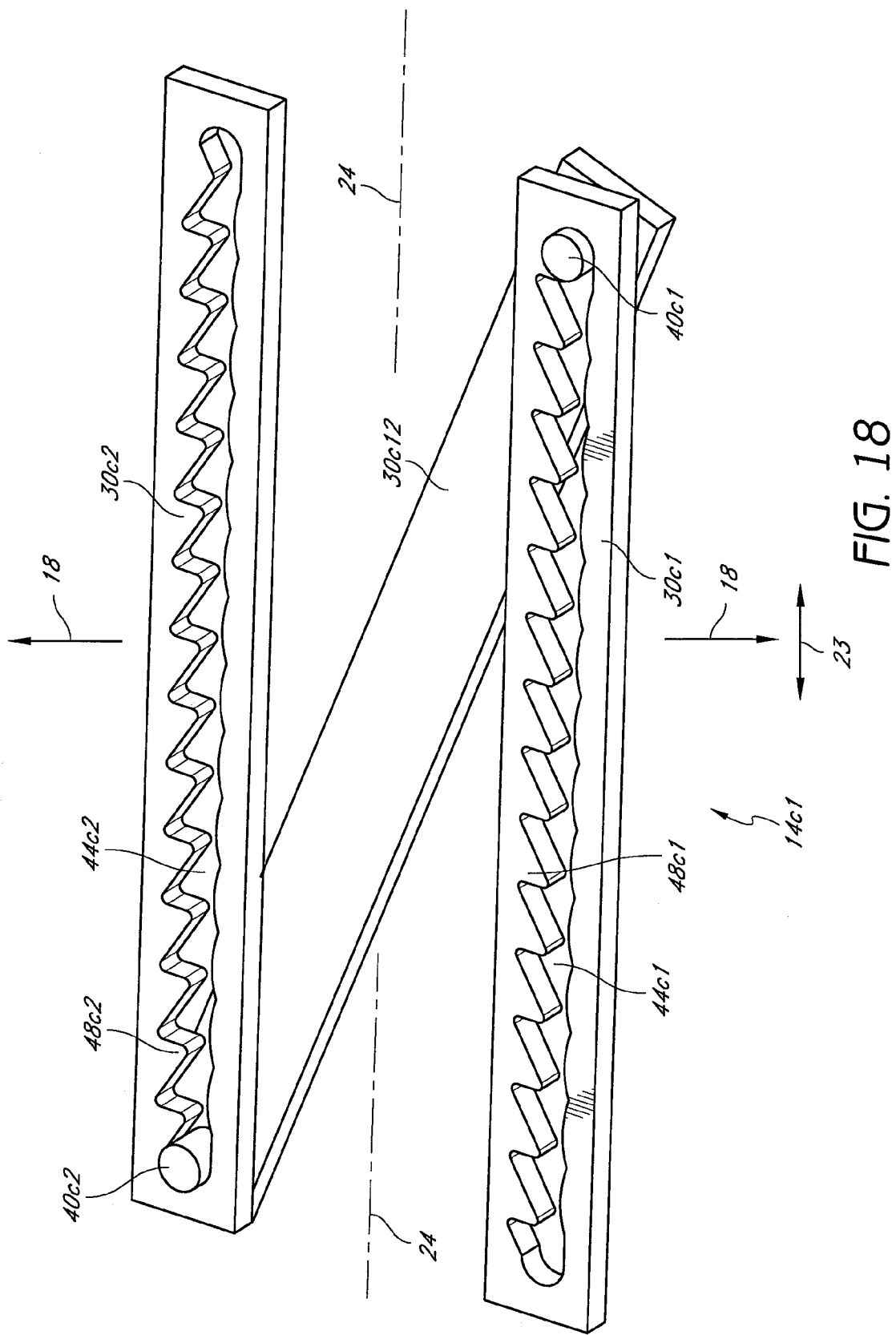
FIG. 18 is a simplified perspective planar view of a three-bar linkage structural element of an expandable rotary circumferentially nested stent illustrating features and advantages in accordance with an embodiment.

FIG. 18 shows a detail view of the embodiment of the three-bar linkage structural element 14c1 shown in FIGS. 16-17. The longitudinal or axial axis can be generally depicted by 24. The stent expansion can be generally depicted by arrows 18.

As shown in FIG. 18, the central bar 30c12 can comprise at least one, and preferably, a pair of generally cylindrical male articulating members, elements or protrusions 40c1 and 40c2 at a respective end thereof connected and/or articulated with respective end bars 30c1 and 30c2. Thus, in some embodiments, one end central bar 30c12 can translate with respect to an end bar 30cN while the other end rotates with respect to the other end bar 30cN. In other embodiments, both ends of the central bar 30c12 can translate with respect to the respective ones of the end bars 30c1 and 30c2.

In some embodiments, the male members 40c1 and 40c2 extend into respective articulating and/or ratcheting slots or female members or elements 44c1 and 44c2 of respective bars 30c1 and 30c2. The bars 30c1 and 30c2 comprise a respective plurality of internal or inwardly extending teeth, lock detents or stops 48c1 and 48c2 which articulate and/or ratchet with respective male members 40c1 and 40c2 of the central bar 30c12 to facilitate controlled stent expansion in one direction only while desirably minimizing or mitigating recoil. The teeth 48c1 and 48c2 can be sized, configured and arranged in a predetermined manner. Various configurations, arrangements, geometries and dimensions of locking mechanisms can be efficaciously used, as needed or desired.

Figure 20:
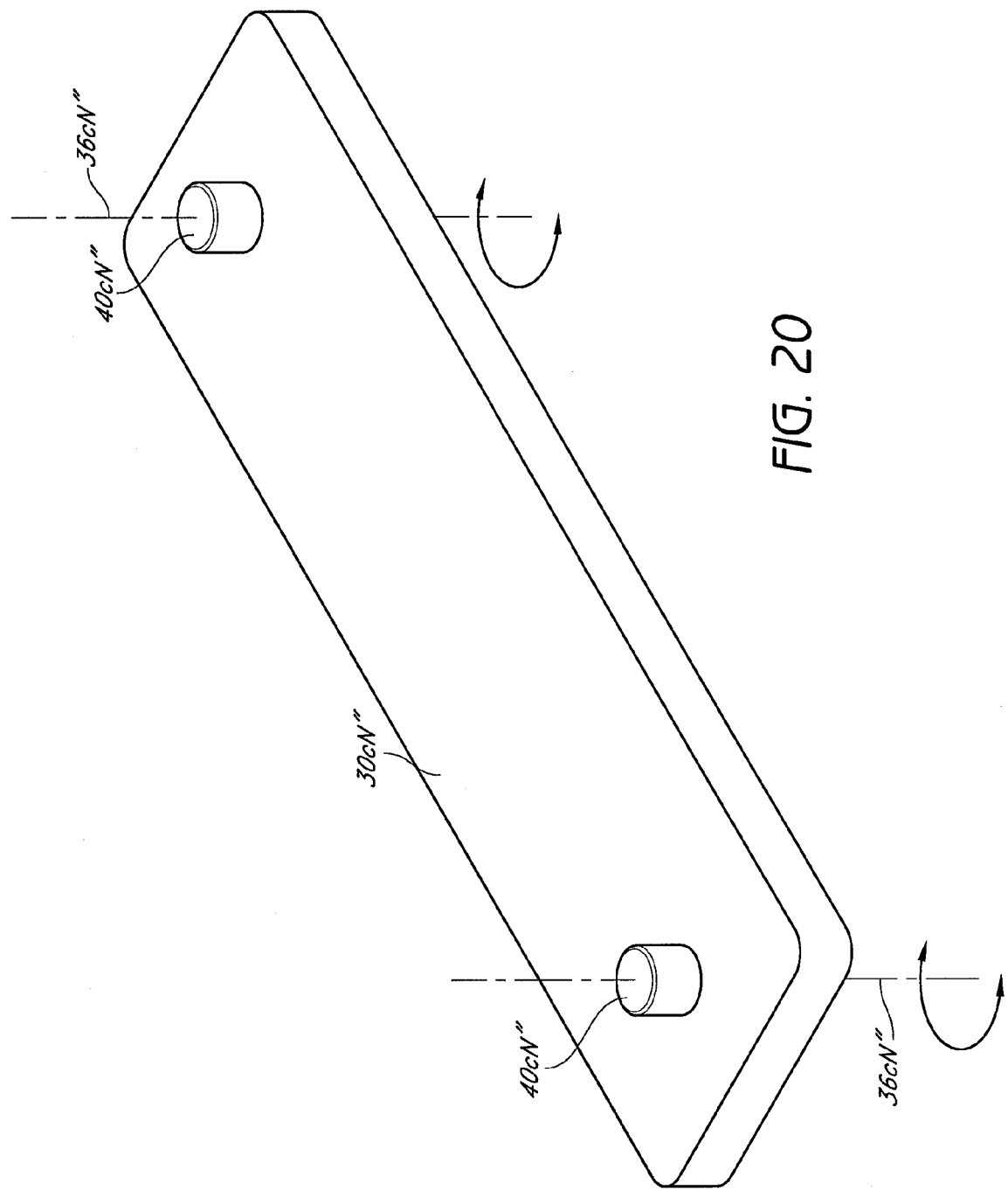
FIG. 20 is a simplified perspective view of a structural element bar or block body of the stent of FIG. 19 illustrating features and advantages in accordance with an embodiment.
Figure 21:
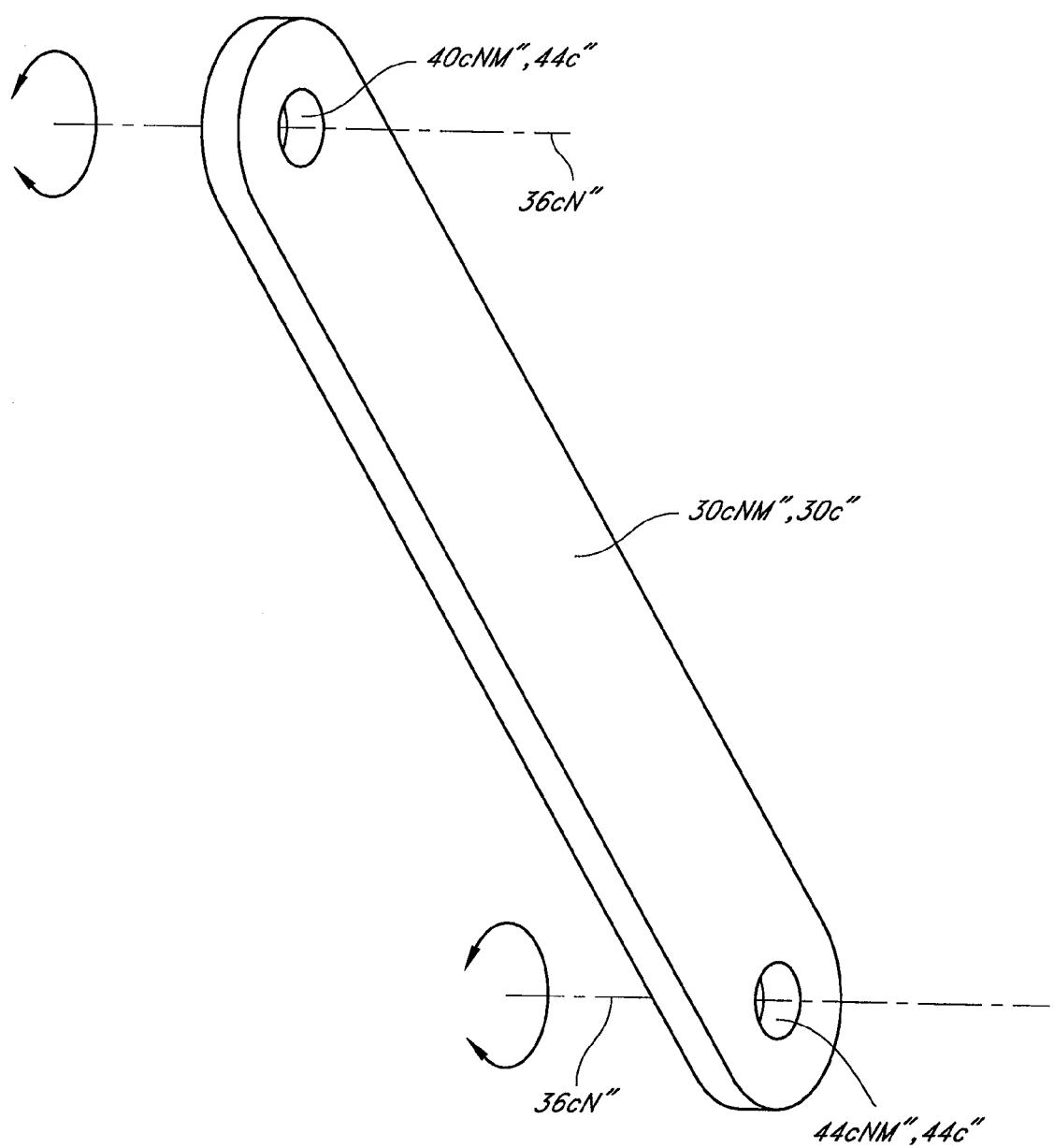
FIG. 21 is a simplified perspective view of a structural element bar or body link of the stent of FIG. 19 illustrating features and advantages in accordance with an embodiment.

FIGS. 19-21 show different views of embodiments of three-bar circumferentially nested structural elements 14c" of an expandable, rotating and translating, vascular device, prosthesis or stent wherein each structural element 14c" generally can comprise stent block bodies, bars, members or elements 30c1" and 30c2" (30cN") connected and/or articulated and/or ratcheted by a central stent body link, bar, member or element 30c12". Axially or longitudinally adjacent stent block bodies, bars, members or elements 30c1" and 30c2" (30cN") can be connected by an intermediate articulating and/or ratcheting stent body link, bar, member or element 30c" generally along the axial or longitudinal axis 24. The stent body bars 30c1", 30c2" and the stent linkage bars 30c12" can be generally also respectively denoted by 30cN", 30cNM".

Typically, two or more structural elements 30c1" can be circumferentially arranged to form a stent section, segment or frame with a plurality of these adjacent stent sections, segments or frames being axially or longitudinally linked or connected to form the stent. Similar to the embodiment shown in FIG. 17, flexible sections 12s which, in some embodiments, comprise one or more spring elements 22, can also be utilized with efficacy, as needed or desired with the embodiment shown in FIG. 19.

The stent expansion can be generally depicted by arrows 18. The axial or longitudinal motion of the structural elements 14c" can be generally denoted by the arrows 23. In this case, the length of the structural element 14c" decreases in size as the structural elements 14c" and stent expand. However, if flexible sections 12s, such as spring or flexible elements 22, are utilized, they can compensate for this reduction in local structural element length and preserve the overall stent length.

Referring to FIG. 20, each stent block body element 30Cn" can comprise on one of its surfaces a pair of spaced protrusions or male members or elements 40CN" at respective ends. The male members 40cN" can efficaciously comprise an axel, pop rivet, pivot pin, pawl or the like, among others, as needed or desired, and further define a rotation axis 36cN" which passes therethrough.

As illustrated in FIG. 21, each stent body link element 30cNM", 30c" can comprise an internal female hole, opening, cavity or port 44cN", 44c" which can axially mate (along rotation axis 36cN") with a corresponding one of the male members 40cN" and receive it therein.

The male and female members 40cN" and 44cN", 44c" can be configured to interact such as to permit motion or rotation (e.g., about rotation axis 36cN") in one direction only to allow for stent expansion to the desired maximum diameter. Thus, compression of an expanded stent can be mitigated by use of the male and female members 40cN" and 44cN", 44c". This can include, but is not limited to, a hinge, ratchet, pawl or other articulation system or mechanism which can employ teeth, detents, spring members and the like.

Furthermore, in other embodiments, the ratchet system embodiments of FIGS. 12-15 can be efficaciously used in conjunction with the circumferentially nested three-link structural elements 14c". For example, these can be used or positioned around the general location of the rotation axis 36cN".

Four-Bar Linkage Stent Embodiments

FIG. 22 shows a four-bar linkage section structural element 14d in accordance with some embodiments of an expandable rotary circumferentially nested vascular device, prosthesis or stent. As indicated above and herein, typically, a plurality of structural elements can be circumferentially and axially arranged to form, in some embodiments, an expandable, circumferentially nested, rotating and translating, vascular device, prosthesis or stent.

The four-bar linkage section structural elements 14d can be axially or longitudinally linked by spring or flexible sections, segments or frames with efficacy, as needed or desired. Each spring or flexible section, segment or frame can comprise one or more spring or flexible elements. The longitudinal or axial axis can be generally depicted by 24. The stent expansion can be generally depicted by arrows 18.

The four-bar linkage structural element 14d generally can comprise four translatable bars, members, ribs or elements 30d1, 30d2 and 30d12, 30d21. The central bars 30d12, 30d21 each comprise a pair of respective generally cylindrical male articulating members, elements or protrusions 40d11, 40d21 and 40d12, 40d22 at respective ends thereof connected and/or articulated with respective side bars 30d1 and 30d2.

The male members 40d11, 40d21 extend into an articulating and/or ratcheting slot or female member or element 44d1 of the side bar 30d1. The male members 40d12, 40d22 extend into an articulating and/or ratcheting slot or female member or element 44d2 of the side bar 30d2.

The bars 30d1 and 30d2 comprise a respective plurality of internal or inwardly extending teeth, lock detents or stops 48d1 and 48d2 which respectively articulate and/or ratchet with male members 40d11, 40d21 and 40d12, 40d22 of respective central bars 30d12, 30d21 to facilitate controlled stent expansion in one direction only while desirably minimizing or mitigating recoil. The teeth 48d1 and 48d2 can be sized, configured and arranged in a predetermined manner. Various configurations, arrangements, geometries and dimensions can be efficaciously used, as needed or desired.

In some embodiments, any of the ratchet system embodiments of FIGS. 12-15 can be efficaciously used in conjunction with the circumferentially nested four-link structural elements 14d. For example, these can be used or positioned around a general location 36d and/or a rotation axis 36d.

These ratcheting members can be configured to interact such as to permit motion or rotation (e.g., about rotation axis 36d) in one direction only to allow for stent expansion to the desired maximum diameter. This can include, but is not limited to, a hinge, ratchet, pawl or other articulation system or mechanism which can employ teeth, detents, spring members and the like.

Ball and Socket Stent Embodiments

FIG. 23 shows a ball and socket structural element 14e in accordance with some embodiments of an expandable rotary circumferentially nested vascular device, prosthesis or stent. As indicated above and herein, typically, a plurality of structural elements can be circumferentially and axially arranged to form, in some embodiments, an expandable, circumferentially nested, rotating and translating, vascular device, prosthesis or stent.

The three-bar linkage ball and socket structural elements 14e can be axially or longitudinally linked by spring or flexible sections, segments or frames with efficacy, as needed or desired. Each spring or flexible section, segment or frame can comprise one or more spring or flexible elements. The longitudinal or axial axis can be generally depicted by 24. The stent expansion can be generally depicted by arrows 18. In some embodiments, four-bar linkage ball and socket structural elements can comprise the vascular device, prosthesis or stent with efficacy, as needed or desired.

The three-bar linkage ball and socket structural element 14e generally can comprise three translatable bars, members, ribs or elements 30e1, 30e2 and 30ec. The central bar 30ec can comprise a pair of generally cylindrical or spherical balls, male articulating members, elements or protrusions 40e12 and 40e21 at a respective end thereof connected and/or articulated with respective side bars 30e1 and 30e2.

The male members 40e12 and 40e21 extend into respective articulating and/or ratcheting sockets, slots or female members or elements 42e12 and 42e21 of respective bars 30e1 and 30e2 to facilitate controlled stent expansion in one direction only while desirably minimizing or mitigating recoil. Ball and socket articulating mechanisms can be generally denoted by 32e12 (generally comprising ball and socket members 40e12 and 42e12) and 32e21 (generally comprising ball and socket members 40e21 and 42e21).

The axial or longitudinal motion of the structural element 14e can be generally denoted by the arrows 23. In this case, the length of the structural element 14e decreases in size as the structural element 14e and stent expand. However, if linkage elements 22, such as flexible sections 12s, are utilized, they can compensate for this reduction in local structural element length and preserve the overall stent length.

In some embodiments, each structural element bar 30e1, 30ec, 30e2 can comprise a respective pair of bars, ribs, elements or members (30e1a, 30e1b), (30e12, 30e21), (30e2a, 30e2b). These can be connected, articulated and/or ratcheted by any of the ratchet system embodiments of FIGS. 12-15. These ratcheting members can be configured to interact such as to permit motion or rotation (e.g., about a rotation axis) in one direction only to allow for stent expansion to the desired maximum diameter. This can include, but is not limited to, a hinge, ratchet, pawl or other articulation system or mechanism which can employ teeth, detents, spring members and the like. In some embodiments, the structural element bars 30e1, 30ec, 30e2 that comprise the respective pair of bars, ribs, elements or members (30e1a, 30e1b), (30e12, 30e21), (30e2a, 30e2b) can be connected by ball and socket mechanisms or joints with efficacy, as needed or desired.

Scissor Stent Embodiments

Figure 24:
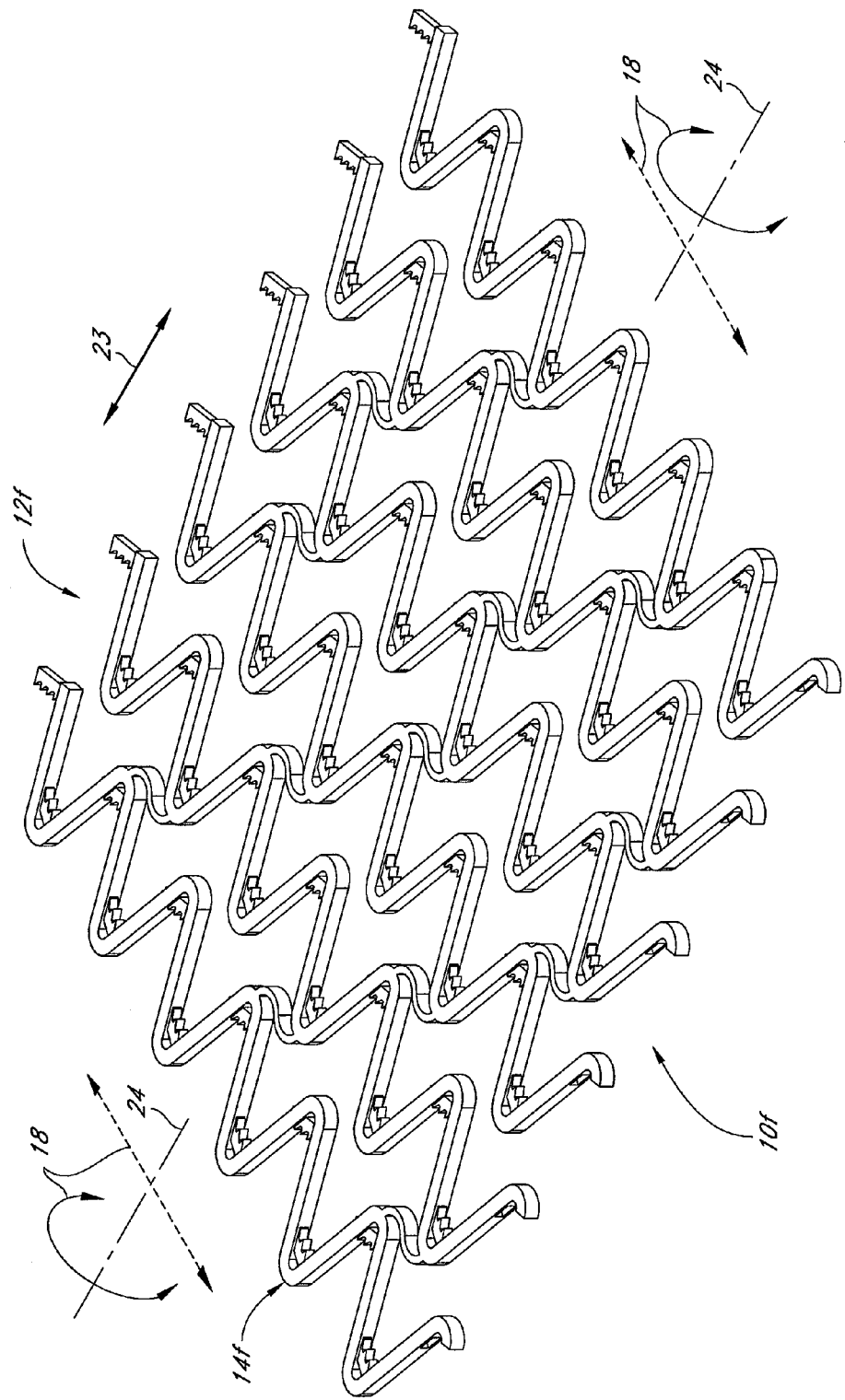
FIG. 24 is a simplified planar perspective view of an expandable rotary circumferentially nested stent with one sliding and one fixed ratchet feature illustrating features and advantages in accordance with an embodiment.
Figure 25:
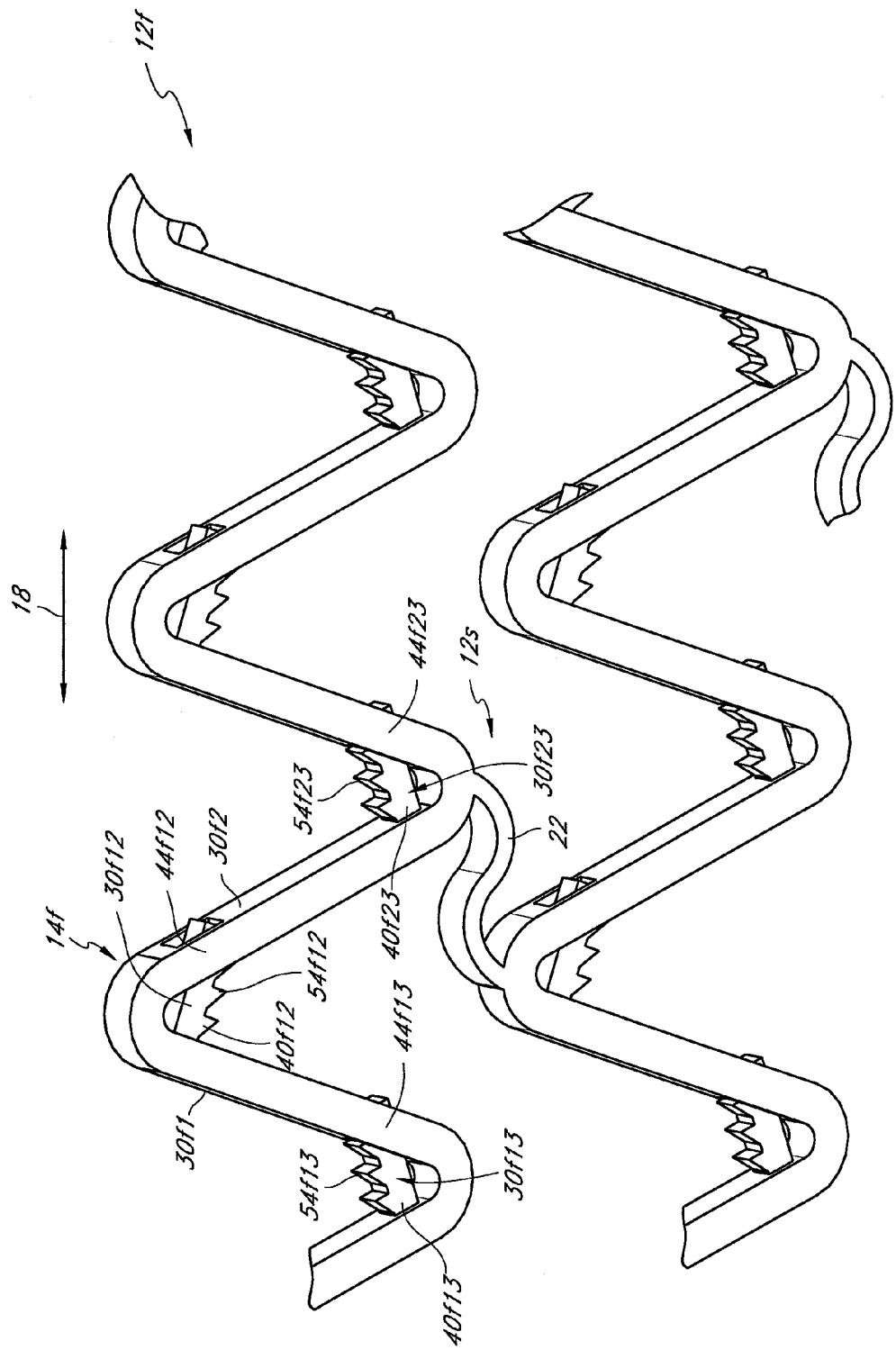
FIG. 25 is a simplified planar perspective view of some of the circumferentially nested structural elements of FIG. 24 illustrating features and advantages in accordance with an embodiment.

FIGS. 24 and 25 show different views of embodiments of an expandable rotary circumferentially nested "scissor" vascular device, prosthesis or stent 10f. The stent 10f can comprise one or more linkage sections, segments or frames 12f. Each section 12f can comprise a one or more circumferentially nested structural elements such as structural element 14f. As indicated above and herein, typically, a plurality of structural elements can be circumferentially and axially arranged to form, in some embodiments, an expandable, circumferentially nested, rotating and translating, vascular device, prosthesis or stent.

The structural elements 14f can be axially or longitudinally linked by flexible sections, segments or frames 12s. In some embodiments the flexible sections 12s comprise spring or flexible sections, segments or frames. Each spring or flexible section, segment or frame 12s can comprise one or more spring or flexible elements 22. The longitudinal or axial axis can be generally depicted by 24. The stent expansion can be generally depicted by arrows 18.

The structural element 14f generally can comprise three bars, members, ribs or elements 30/1, 30/2 and 30/12 with the bar 30/1 being connected to a circumferentially adjacent stent structural element by a bar, member, rib or element 30/13 and the bar 30/2 being connected to a circumferentially adjacent stent structural element by a bar, member, rib or element 30/23. The bars 30f can be configured to provide for circumferential nesting and allow one-way sliding circumferential stent expansion.

During stent expansion, the bars 30/1 and 30/2 translate in the circumferential direction 18 (the bars 30/12, 30/13, 30/23 can also translate) to provide stent expansion. As shown in the embodiment illustrated in FIGS. 24-25, the bars 30/1 and 30/2 can be coupled. For example, the bars 30/1 and 30/2 can be coupled via a hinged coupling 31. The coupling 31 can be formed through connection of individual bars 30/1 and 30/2, or the bars 30/1 and 30/2 can be integrally formed to create the coupling 31. Typically, a plurality of structural elements 14f can be circumferentially and axially arranged to form, in some embodiments, an expandable, circumferentially nested, rotating and translating, vascular device, prosthesis or stent. In some of these embodiments, there can be no change in the stent 10f axial or longitudinal length because it can be compensated for by the spring sections 12s while in other embodiments there can be a change in axial or longitudinal stent length as generally indicated by arrows 23.

In FIG. 25, the central bar 30/12 can comprise a male ratcheting and/or articulating member or element 40/12 which can extend into and ratchet and/or articulate with a female member, element, port, opening, hole or slot 44/12 to provide one way sliding stent expansion. The male member 40/12 can comprise a plurality of teeth, lock detents or stops 54/12 which ratchet and/or articulate with the female slot 44/12 to facilitate controlled stent expansion in one direction only while desirably minimizing or mitigating recoil. The teeth 54/12 can be sized, configured and arranged in a predetermined manner. Various configurations, arrangements, geometries and dimensions can be efficaciously used, as needed or desired. The female slot 44/12 can also comprise one or more teeth, lock detents or stops with efficacy, as needed or desired.

The central bar 30/12 can be fixedly attached at one end to the bar 30/1 and movably extend into the female slot 44/12 of the bar 30/2. Similarly, the bar 30/13 can comprise a male ratcheting and/or articulating member or element 40/13 with teeth, lock detents or stops 54/13 which ratchet and/or articulate with a female member, element, port, opening, hole or slot 44/13 of the bar 30/1. The bar 30/13 can be fixedly attached at one end to a bar of a circumferentially adjacent structural element and movably extend into the female slot 44/13 of the bar 30/1.

The bar 30/23 can comprise a male ratcheting and/or articulating member or element 40/23 with teeth, lock detents or stops 54/23 which ratchet and/or articulate with a female member, element, port, opening, hole or slot 44/23 of to a bar of a circumferentially adjacent structural element. The bar 30/23 can be fixedly attached at one end to the bar 30/2 and movably extend into the female slot 44/23 of the bar of the circumferentially adjacent structural element.

Figure 26:
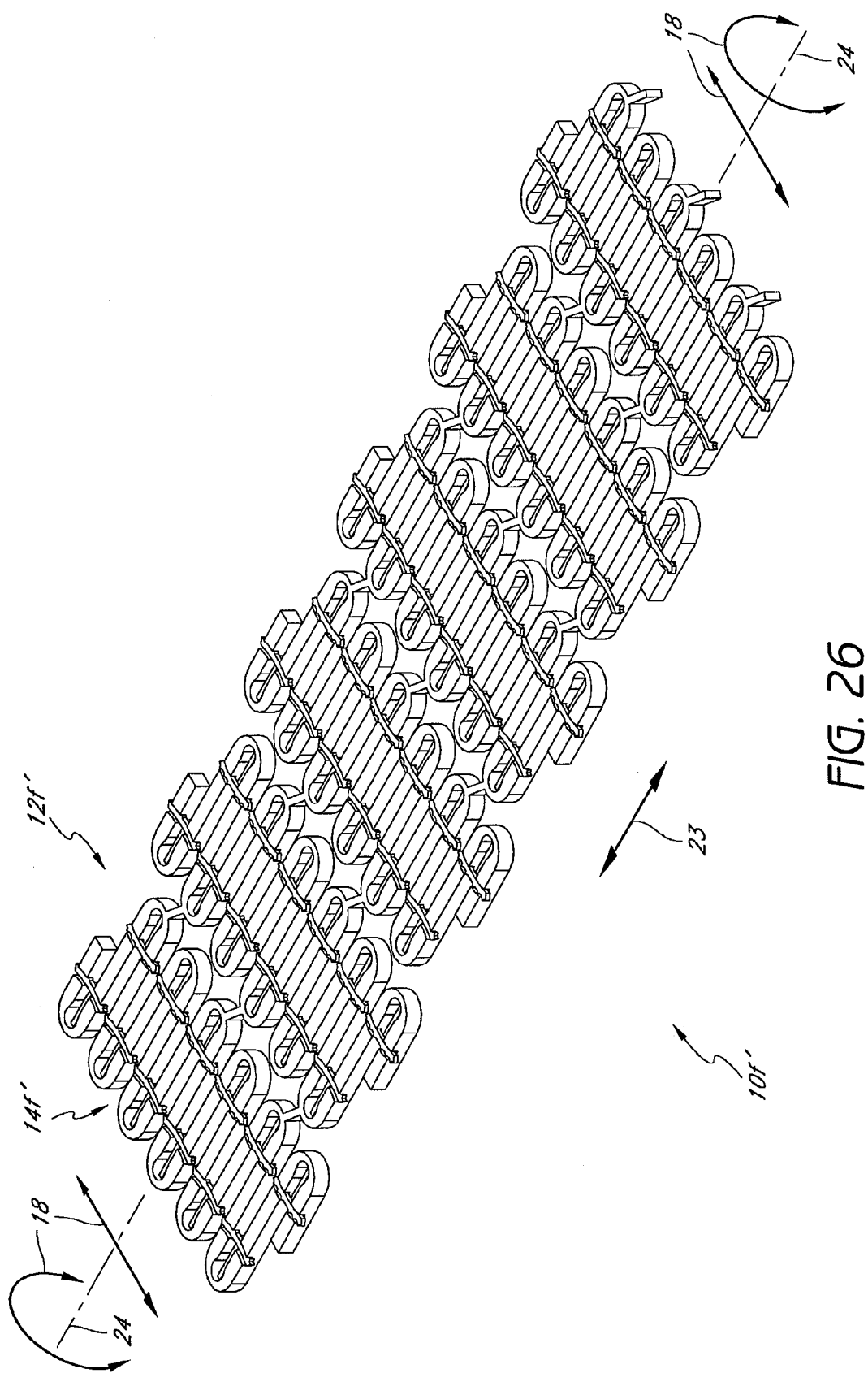
FIG. 26 is a simplified planar perspective view of an expandable rotary circumferentially nested stent with a pair of sliding ratchet features illustrating features and advantages in accordance with an embodiment.
Figure 27:
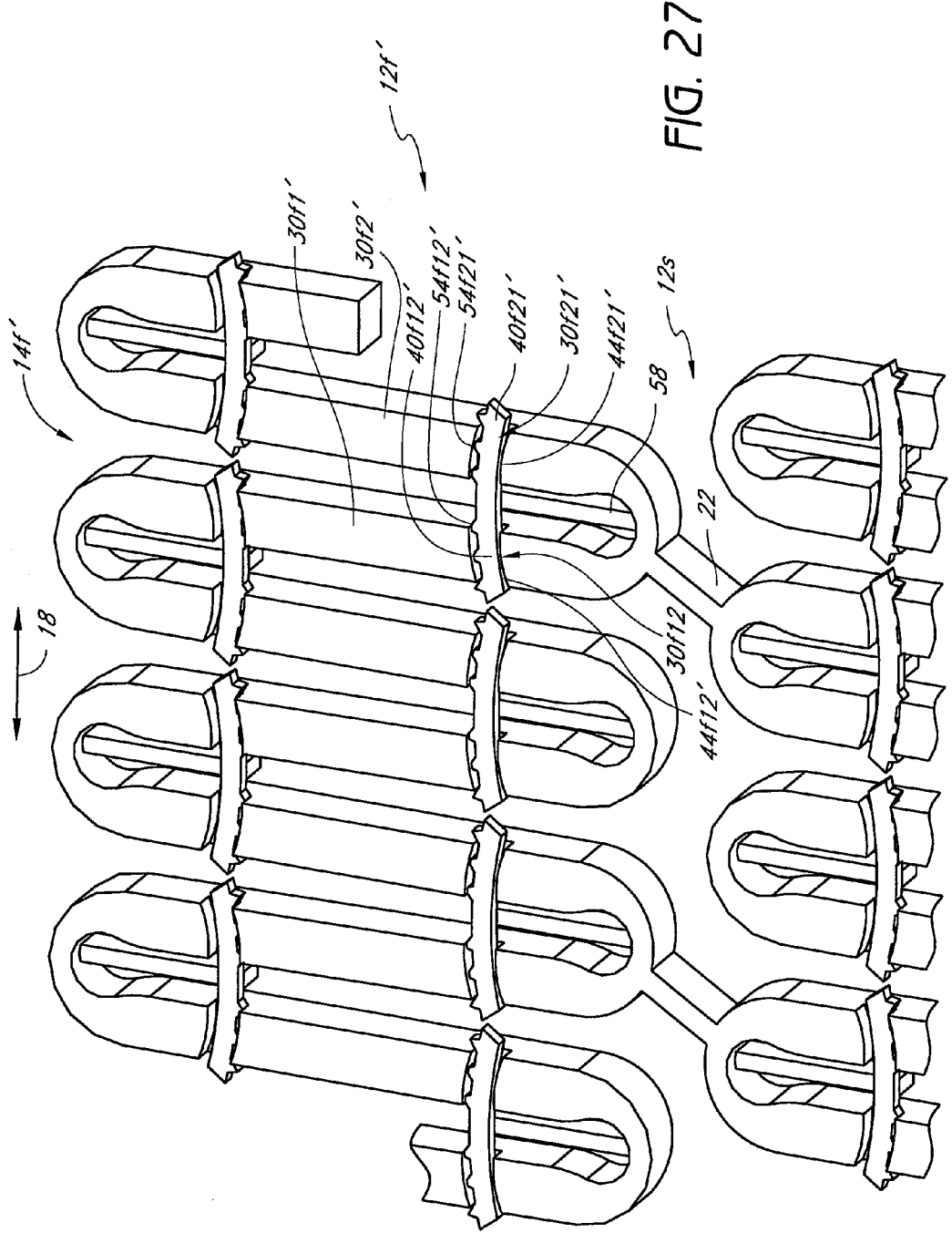
FIG. 27 is a simplified planar perspective view of some of the circumferentially nested structural elements of FIG. 26 illustrating features and advantages in accordance with an embodiment.

FIGS. 26 and 27 show different views of embodiments of an expandable rotary circumferentially nested "scissor" vascular device, prosthesis or stent 10f'. The stent 10f' can comprise one or more linkage sections, segments or frames 12f'. Each section 12f' can comprise a one or more circumferentially nested structural elements such as structural element 14f'. As indicated above and herein, typically, a plurality of structural elements can be circumferentially and axially arranged to form, in some embodiments, an expandable, circumferentially nested, rotating and translating, vascular device, prosthesis or stent.

The structural elements 14f can be axially or longitudinally linked by flexible sections, segments or frames 12s. In some embodiments the flexible sections 12s comprise spring or flexible sections, segments or frames. Each spring or flexible section, segment or frame 12s can comprise one or more spring or flexible elements 22. The longitudinal or axial axis can be generally depicted by 24. The stent expansion can be generally depicted by arrows 18.

The structural element 14f generally can comprise four bars, members, ribs or elements 30/1', 30/2', 30/12' and 30/21'. The bars 30f' can be configured to provide for circumferential nesting and allow one-way sliding circumferential stent expansion.

During stent expansion, the bars 30/1' and 30/2' translate in the circumferential direction 18 (the bars 30/12', 30/21' can also translate) to provide stent expansion. Typically, a plurality of structural elements 14f' can be circumferentially and axially arranged to form, in some embodiments, an expandable, circumferentially nested, rotating and translating, vascular device, prosthesis or stent. In some of these embodiments, there can be no change in the stent 10f' axial or longitudinal length because it can be compensated for by the spring sections 12s while in other embodiments there can be a change in axial or longitudinal stent length as generally indicated by arrows 23.

The central bars 30/12' and 30/21' can be connected and each can comprise a respective male ratcheting and/or articulating member or element 40/12', 40/21' which extend into and ratchet and/or articulate with respective female members, elements, ports, openings, holes or slots 44/12', 44/21' to provide one way sliding stent expansion. The male members 40/12', 40/21' comprise a respective plurality of teeth, lock detents or stops 54/12', 54/21' which ratchet and/or articulate with respective female slots 44/12', 44/21' to facilitate controlled stent expansion in one direction only while desirably minimizing or mitigating recoil. The teeth 54/12', 54/21' can be sized, configured and arranged in a predetermined manner. Various configurations, arrangements, geometries and dimensions can be efficaciously used, as needed or desired. The female slots 44/12', 44/21' can also comprise one or more teeth, lock detents or stops with efficacy, as needed or desired.

The central bar 30/12' movably extends into the female slot 44/12' of the bar 30/1'. The central bar 30/21' can movably extend into the female slot 44/21' of the bar 30/2'. Further, the central bar 30/21' can be interconnected with a support bar 58. The support bar 58 can be formed integrally with the structural element 14f. For example, as shown in FIG. 27, the support bar 58 can be formed integrally with one of the bars 30/1' and 30/2'. The support bar 58 can be configured to extend from the bars 30/1' and/or 30/2' to hold the central bars 30/12' and 30/21' in contact with the respective female slots 44/12' and 44/21', respectively.

Lamination Manufacturing Process Embodiments

Stents in accordance with embodiments can be fabricated or created using a wide variety of manufacturing methods, techniques and procedures. These include, but are not limited to, laser processing, milling, stamping, forming, casting, molding, bonding, welding, adhesively fixing, and the like, among others.

In some embodiments, stent features and mechanisms can be created in a generally two dimensional geometry and further processed, for example by utilizing, but not limited to, bonding, lamination and the like, into three dimensional designs and features. In other embodiments, stent features and mechanisms can be directly created into three dimensional shapes, for example by utilizing, but not limited to, processes such as injection molding and the like.

In certain embodiments, stents can be fabricated by using a an injection molding process, technique or method. For example, an injection molding process or the like, among others, can be used to form stent rows as integral units. The axially extending rows can then be connected and rolled into a tubular form in the collapsed state.

In some embodiments, a lamination stack can used to fabricate the stent rows by a lamination process in accordance with one embodiment. The axially extending rows can then be connected and rolled into a tubular form in the collapsed state.

The lamination stack, in some embodiments, generally can comprise three sheets or pallets which can have the desired features formed thereon, for example, by laser cutting, etching and the like. The pallets can be aligned and joined, for example, by bonding, welding and the like to form a unit. The excess material (e.g., side and end rails) can be removed to form the stent rows. The pallets can include various circumferentially nesting features such as male and female articulating and/or ratcheting designs to control and limit the diameter in collapsed and fully deployed states.

Combination Circumferentially and Axially Nesting Embodiments

Some stent embodiments provide at least one stent structural element that efficaciously can comprise a combination of circumferentially and axially nesting features of a stent, as required or desired. Certain embodiments of axially nested stents are disclosed in co-pending U.S. patent application Ser. No. 11/196,800, filed Aug. 2, 2005, the disclosure of which is hereby incorporated by reference herein.

Metal Stents and Methods of Manufacturing

Preferred materials for making the stents in accordance with some embodiments include cobalt chrome, 316 stainless steel, tantalum, titanium, tungsten, gold, platinum, iridium, rhodium and alloys thereof or pyrolytic carbon. In still other alternative embodiments, the stents can be formed of a corrodible material, for instance, a magnesium alloy. Although preferred stent embodiments have been described as being conventional balloon expandable stents, those skilled in the art will appreciate that stent constructions according to embodiments can also be formed from a variety of other materials to make a stent crush-recoverable. For example, in alternative embodiments, such as self expandable stents, shape memory alloys that allow for such, such as Nitinol and Elastinite®, can be used in accordance with embodiments.

Preferred methods of forming the individual elements from metal sheets can be laser cutting, laser ablation, die-cutting, chemical etching, plasma etching and stamping and water jet cutting of either tube or flat sheet material or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Some methods allow for different front and back etch artwork, which could result in chamfered edges, which can be desirable to help improve engagements of lockouts. Further one can use plasma etching or other methods known in the art which are capable of producing high-resolution and polished components. The embodiments disclosed herein are not limited to the means by which stent or stent elements can be fabricated.

Once the base geometry is achieved, the elements can be assembled numerous ways. Tack-welding, adhesives, mechanical attachment (snap-together and/or weave together), and other art-recognized methods of attachment, can be used to fasten the individual elements. Some methods allow for different front and back etch artwork, which could result in chamfered edges, which can be desirable to help improve engagements of lockouts. In one preferred method of manufacture, the components of the stent can be heat set at various desired curvatures. For example, the stent can be set to have a diameter equal to that of the deflated balloon, as deployed, at a maximum diameter, or greater than the maximum diameter. In yet another example, elements can be electropolished and then assembled, or electropolished, coated, and then assembled, or assembled and then electropolished.

Polymeric Stents

While metal stents possess certain desirable characteristics, the useful lifespan of a stent is estimated to be in the range of about 6 to 9 months, the time at which in-stent restenosis stabilizes and healing plateaus. In contrast to a metal stent, a bioresorbable stent cannot outlive its usefulness within the vessel. Moreover, a bioresorbable stent could potentially be used to deliver a greater dose of a therapeutic agent, deliver multiple therapeutic agents at the same time or at various times of its life cycle, to treat specific aspects or events of vascular disease. Additionally, a bioresorbable stent can also allow for repeat treatment of the same approximate region of the blood vessel. Accordingly, there remains an important unmet need to develop temporary (i.e., bioresorbable and/or radiopaque) stents, wherein the polymeric materials used to fabricate these stents can have the desirable qualities of metal (e.g., sufficient radial strength and radiopacity, etc.), while circumventing or alleviating the many disadvantages or limitations associated with the use of permanent metal stents.

In one preferred embodiment, the stent can be formed from biocompatible polymers that are bio-resorbable (e.g., bio-erodible or bio-degradable). Bio-resorbable materials can be preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. For additional information, see U.S. Pat. Nos. 4,980,449, 5,140,094, and 5,264,537, the disclosures of each of which are incorporated by reference herein.

In one mode, the degradable materials can be selected from the group consisting of poly(glycolide-trimethylene carbonate), poly(alkylene oxalates), polyaspartimic acid, polyglutarunic acid polymer, poly-p-dioxanone, poly-.beta.-dioxanone, asymmetrically 3,6-substituted poly-1,4-dioxane-2,5-diones, polyalkyl-2-cyanoacrylates, polydepsipeptides (glycine-DL-lactide copolymer), polydihydropyranes, polyalkyl-2-cyanoacrylates, poly-.beta.-maleic acid (PMLA), polyalkanotes and poly-.beta.-alkanoic acids. There are many other degradable materials known in the art. (See e.g., Biomaterials Science: An Introduction to Materials in Medicine (29 Jul., 2004) Ratner, Hoffman, Schoen, and Lemons; and Atala, A., Mooney, D. Synthetic Biodegradable Polymer Scaffolds. 1997 Birkhauser, Boston; each of which are incorporated herein by reference).

Further still, in a more preferred embodiment, the stents can be formed of a polycarbonate material, such as, for example, tyrosine-derived polycarbonates, tyrosine-derived polyarylates, tyrosine-derived diphenol monomers, iodinated and/or brominated tyrosine-derived polycarbonates, iodinated and/or brominated tyrosine-derived polyarylates. For additional information, see U.S. Pat. Nos. 5,099,060, 5,198,507, 5,587,507, which was resiussed in RE37,160, U.S. Pat. No. 5,670,602, which was resiussed in RE37,795 , U.S. Pat. Nos. 5,658,995, 6,048,521, 6,120,491, 6,319,492, 6,475,477, 5,317,077, and 5,216,115, and U.S. application Ser. No. 09/350,423, the disclosures of each of which are incorporated by reference herein. In another preferred embodiment, the polymer can be any of the biocompatible, bioabsorbable, radiopaque polymers disclosed in U.S. Patent Application Nos. 60/601,526, 60/586,796, 60/866,281, 60/885,600, Ser. Nos. 10/952,202, 11/176,638, 11/335,771, 11/200,656, 11/024,355, 10/691,749, and 11/418,943, U.S. Pat. Nos. 6,852,308 and 7,056,493, and PCT Application Nos. PCT/US2005/024289, PCT/US2005/028228 and PCT/US07/01011, the disclosures of each of which are incorporated herein by reference thereto.

Natural polymers (biopolymers) include any protein or peptide. Preferred biopolymers can be selected from the group consisting of alginate, cellulose and ester, chitosan, collagen, dextran, elastin, fibrin, gelatin, hyaluronic acid, hydroxyapatite, spider silk, cotton, other polypeptides and proteins, and any combinations thereof.

In yet another alternative embodiment, shape-shifting polymers can be used to fabricate stents constructed according to embodiments. Suitable shape-shifting polymers can be selected from the group consisting of polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof. For addition disclosure on bio-degradable shape-shifting polymers, see U.S. Pat. Nos. 6,160,084 and 6,284,862, the disclosures of each of which are incorporated by reference herein. For additional disclosure on shape memory polymers, see U.S. Pat. Nos. 6,388,043 and 6,720,402, the disclosures of each of which are incorporated by reference herein. Further the transition temperature can be set such that the stent can be in a collapsed condition at a normal body temperature. However, with the application of heat during stent placement and delivery, such as via a hot balloon catheter or a hot liquid (e.g., saline) perfusion system, the stent can expand to assume its final diameter in the body lumen. When a thermal memory material is used, it can provide a crush-recoverable structure.

Further still, stents can be formed from biocompatible polymers that are biostable (e.g., non-degrading and non-erodible). Examples of suitable non-degrading materials include, but are not limited to, polyurethane, Delrin, high density polyethylene, polypropylene, and poly(dimethyl siloxane).

In some embodiments, the layers can comprise or contain any example of thermoplastics, such as the following, among others: fluorinated ethylene-propylene, poly(2-hydroxyethyl methacrylate) (aka pHEMA), poly(ethylene terephthalate) fiber (aka Dacron®) or film (Mylar®), poly(methyl methacrylate) (aka PMMA), Poly(tetraflouroethylene) (aka PTFE and ePTFE and Gore-Tex®), poly(vinyl chloride), polyacrylates and polyacrylonitrile (PAN), polyamides (aka Nylon), polycarbonates and polycarbonate urethanes, polyethylene and poly(ethylene-co-vinyl acetate), polypropylene, polystyrene, polysulphone, polyurethane and polyetherurethane elastomers such as Pellethane® and Estane®, Silicone rubbers, Siloxane, polydimethylsiloxane (aka PDMS), Silastic®, Siliconized Polyurethane.

Finally, the polymer(s) utilized in embodiments of the stent can be fabricated according to any variety of processes, such as those discussed in U.S. Patent Application Nos. 60/852,471 and 60/852,513, and U.S. Pat. Nos. 5,194,570, 5,242,997, 6,359,102, 6,620,356, and 6,916,868, the disclosures of each of which are incorporated by reference herein.

Methods of Manufacturing and Assembling Polymeric Stents

Where plastic and/or degradable materials are used, the elements can be made using laser ablation with a screen, stencil or mask; solvent casting; forming by stamping, embossing, compression molding, centripetal spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized molding, or silicone rubber molding; casting techniques comprising casting with solvents, direct shell production casting, investment casting, pressure die casting, resin injection, resin processing electroforming, or injection molding or reaction injection molding. Certain preferred embodiments with the disclosed polymers can be shaped into stents via combinations of two or more thereof, and the like.

Such processes can further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. For additional information, see U.S. patent application Ser. No. 10/655,338, the disclosure of which is incorporated by reference herein.

Stents of the preferred embodiment can be manufactured with elements prepared in full stent lengths or in partial lengths of which two or more are then connected or attached. If using partial lengths, two or more can be connected or attached to comprise a full length stent. In this arrangement the parts can be assembled to give rise to a central opening. The assembled full or partial length parts and/or modules can be assembled by inter-weaving them in various states, from a collapsed state, to a partially expanded state, to an expanded state.

Further, elements can be connected or attached by solvent or thermal bonding, or by mechanical attachment. If bonding, preferred methods of bonding comprise the use of ultrasonic radiofrequency or other thermal methods, and by solvents or adhesives or ultraviolet curing processes or photoreactive processes. The elements can be rolled by thermal forming, cold forming, solvent weakening forming and evaporation, or by preforming parts before linking.

Another method of manufacture allows for assembly of the stent components that have been cut out and assembled into flat series of radial elements. The linkage elements, flexible sections, etc. between longitudinally adjacent series of radial elements can be connected (e.g., by welding, inter-weaving frame elements, etc.), and the flat sheets of material can be rolled to form a tubular member. Coupling arms from floating coupling elements and end portions can be joined (e.g., by welding) to maintain the tubular shape. In embodiments that do not include coupling elements, the end portions of the top and bottom radial elements in a series can be joined. Alternatively, where sliding is desired throughout the entire circumference, a sliding and locking articulation can be made between the end portion of the top radial element and the rib(s)/rails of the bottom radial element (e.g., by tack-welding, heat-staking or snap-together). Similarly, a corresponding articulation can be made between the end portion of the bottom radial element and the rib(s)/rails of the top radial element.

Rolling of the flat series of module(s) to form a tubular member can be accomplished by any means known in the art, including rolling between two plates, which can be each padded on the side in contact with the stent elements. One plate can be held immobile and the other can move laterally with respect to the other. Thus, the stent elements sandwiched between the plates can be rolled about a mandrel by the movement of the plates relative to one another. Alternatively, 3-way spindle methods known in the art can also be used to roll the tubular member. Other rolling methods that can be used in accordance with certain embodiments include those used for "jelly-roll" designs, as disclosed for example, in U.S. Pat. Nos. 5,421,955, 5,441,515, 5,618,299, 5,443,500, 5,649, 977, 5,643,314 and 5,735,872, the disclosures of each of which are incorporated herein in their entireties by reference thereto.

The construction of the slide-and-lock stents in these fashions can provide a great deal of benefit over the prior art. The construction of the locking mechanism can be largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency of catches, stops or teeth present on selected circumferential elements can prevent unnecessary recoil of the stent subsequent to expansion.

Radiopacity

Traditional methods for adding radiopacity to a medical product include the use of metal bands, inserts and/or markers, electrochemical deposition (i.e., electroplating), or coatings. The addition of radiopacifiers (i.e., radiopaque materials) to facilitate tracking and positioning of the stent could be accommodated by adding such an element in any fabrication method, by absorbing into or spraying onto the surface of part or all of the device. The degree of radiopacity contrast can be altered by element content.

For plastics and coatings, radiopacity can be imparted by use of monomers or polymers comprising iodine or other radiopaque elements, i.e., inherently radiopaque materials. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, a halogen such as iodine and/or bromine can be employed for its radiopacity and antimicrobial properties.

Multi-Material Vascular Prosthesis

In still other alternative embodiments, various materials (e.g., metals, polymers, ceramics, and therapeutic agents) can be used to fabricate stent embodiments. The embodiments can comprise: 1) differentially layered materials (through stacking in the vertical or radial axis) to create a stack of materials (materials can be stacked in any configuration, e.g., parallel, staggered, etc.); 2) spatially localized materials which can vary along the long axis and/or thickness of the stent body; 3) materials that are mixed or fused to create a composite stent body; 4) embodiments whereby a material can be laminated (or coated) on the surface of the stent body (see Stent Surface Coatings with Functional Properties as well as see Therapeutic Agents Delivered by Stents); and, 5) stents comprised of 2 or more parts where at least one part can be materially distinct from a second part, or any combination thereof.

The fashioning of a slide-and-lock multi-material stent can have between two or more materials. Thickness of each material can vary relative to other materials. This approach as needed or desired allows an overall structural member to be built with each material having one or more functions contributing towards enabling prosthesis function which can include, but is not limited to: 1) enabling mechanical properties for stent performance as defined by ultimate tensile strength, yield strength, Young's modulus, elongation at yield, elongation at break, and Poisson's ratio; 2) enabling the thickness of the substrate, geometrical shape (e.g., bifurcated, variable surface coverage); 3) enabling chemical properties of the material that bear relevance to the materials performance and physical state such as rate of degradation and resorption (which can impact therapeutic delivery), glass transition temperature, melting temperature, molecular weight; 4) enabling radiopacity or other forms of visibility and detection; 5) enabling radiation emission; 6) enabling delivery of a therapeutic agent (see Therapeutic Agents Delivered by Stents); and 7) enabling stent retention and/or other functional properties (see Stent Surface Coatings with Functional Properties).

In some embodiments, the materials can comprise load-bearing properties, elastomeric properties, mechanical strength that can be specific to a direction or orientation e.g., parallel to another material and/or to the long axis of the stent, or perpendicular or uniform strength to another material and/ or stent. The materials can comprise stiffeners, such as the following, boron or carbon fibers, pyrolytic carbon. Further, stents can be comprised of at least one re-enforcement such a fibers, nanoparticles or the like.

In another preferred mode of some embodiments, the stent can be made, at least in part, from a polymeric material, which can be degradable. The motivation for using a degradable stent can be that the mechanical support of a stent can only be necessary for several weeks. In some embodiments, bioresorbable materials with varying rates of resorption can be employed. For additional information, see U.S. patent application Ser. Nos. 10/952,202 and 60/601,526, the disclosures of each of which are incorporated by reference herein. Degradable polymeric stent materials can be particularly useful if it also controls restenosis and thrombosis by delivering pharmacologic agents. Degradable materials can be well suited for therapeutic delivery (see Therapeutic Agents Delivered by Stents).

In some embodiments, the materials can comprise or contain any class of degradable polymer as previously defined. Along with variation in the time of degradation and/or resorption the degradable polymer can have other qualities that are desirable. For example, in some embodiments the materials can comprise or contain any example of natural polymers (biopolymers) and/or those that degrade by hydrolytic and/or enzymatic action. In some embodiments, the material can comprise or contain any example of hydrogels that can or cannot be thermally reversible hydrogels, or any example of a light or energy curable material, or magnetically stimulateable (responding) material. Each of these responses can provide for a specific functionality.

In some embodiments, the materials can comprise or be made from or with constituents which can have some radiopaque material alternatively, a clinically visible material which can be visible by x-ray, fluoroscopy, ultrasound, MRI, or Imatron Electron Beam Tomography (EBT).

In some embodiments, one or more of the materials can emit predetermined or prescribed levels of therapeutic radiation. In one embodiment, the material can be charged with beta radiation. In another embodiment, the material can be charged with Gamma radiation. In yet another embodiment, the material can be charged with a combination of both Beta and Gamma radiation. Stent radioisotopes that can be used include, but are not limited to, 103Pd and 32P (phosphorus-32) and two neutron-activated examples, 65Cu and 87Rb2O, (90)Sr, tungsten-188 (188).

In some embodiments, one or more of the materials can comprise or contain a therapeutic agent. The therapeutic agents can have unique, delivery kinetics, mode of action, dose, half-life, purpose, et cetera. In some embodiments, one or more of the materials comprise an agent which provides a mode and site of action for therapy for example by a mode of action in the extracellular space, cell membrane, cytoplasm, nucleus and/or other intracellular organelle. Additionally an agent that serves as a chemoattractant for specific cell types to influence tissue formation and cellular responses for example host-biomaterial interactions, including anti-cancer effects. In some embodiments, one or more of the materials deliver cells in any form or state of development or origin. These could for example be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells can serve as a limited release system. For additional concepts of therapeutic delivery, see the section entitled: Therapeutic Agents Delivered by Stents.

Therapeutic Agents Delivered by Stents

In another preferred variation, the stent further can comprise an amount of a therapeutic agent (as previously defined for a pharmaceutical agent and/or a biologic agent) sufficient to exert a selected therapeutic effect. In some preferred embodiments of the stent (e.g., polymer stents and multimaterial stents) the therapeutic agent can be contained within the stent as the agent is blended with the polymer or admixed by other means known to those skilled in the art. In other preferred embodiments of the stent, the therapeutic agent can be delivered from a polymer coating on the stent surface. In some preferred embodiments of the stent a therapeutic agent can be localized in or around a specific structural aspect of the device.

In another preferred variation the therapeutic agent can be delivered by means of a non-polymer coating. In other preferred embodiments of the stent, the therapeutic agent can be delivered from at least one region or one surface of the stent. The therapeutic can be chemically bonded to the polymer or carrier used for delivery of the therapeutic from at least one portion of the stent and/or the therapeutic can be chemically bonded to the polymer that can comprise at least one portion of the stent body. In one preferred embodiment, more than one therapeutic agent can be delivered.

The amount of the therapeutic agent can be preferably sufficient to inhibit restenosis or thrombosis or to affect some other state of the stented tissue, for instance, heal a vulnerable plaque, and/or prevent rupture or stimulate endothelialization or limit other cell types from proliferating and from producing and depositing extracellular matrix molecules. The agent(s) can be selected from the group consisting of antiproliferative agents, anti-inflammatory, anti-matrix metalloproteinase, and lipid lowering, cholesterol modifying, anti-thrombotic and antiplatelet agents, in accordance with preferred embodiments. Some of these preferred anti-proliferative agents that improve vascular patency include without limitation paclitaxel, Rapamycin, ABT-578, everolimus, dexamethasone, nitric oxide modulating molecules for endothelial function, tacrolimus, estradiol, mycophenolic acid, C6-ceramide, actinomycin-D and epothilones, and derivatives and analogs of each.

Some of these preferred agents act as an antiplatelet agent, antithrombin agent, compounds to address other pathologic events and/or vascular diseases. Various therapeutic agents can be classified in terms of their sites of action in the host: agents that exert their actions extracellularly or at specific membrane receptor sites, those that act on the plasma membrane, within the cytoplasm, and/or the nucleus.

In addition to the aforementioned, therapeutic agents can include other pharmaceutical and/or biologic agents intended for purposes of treating body lumens other than arteries and/or veins). Therapeutic agents can be specific for treating nonvascular body lumens such as digestive lumens (e.g., gastrointestinal, duodenum and esophagus, biliary ducts), respiratory lumens (e.g., tracheal and bronchial), and urinary lumens (e.g., urethra). Additionally such embodiments can be useful in lumens of other body systems such as the reproductive, endocrine, hematopoietic and/or the integumentary, musculoskeletal/orthopedic and nervous systems (including auditory and ophthalmic applications); and finally, stent embodiments with therapeutic agents can be useful for expanding an obstructed lumen and for inducing an obstruction (e.g., as in the case of aneurysms).

Therapeutic release can occur by controlled release mechanisms, diffusion, interaction with another agent(s) delivered by intravenous injection, aerosolization, or orally. Release can also occur by application of a magnetic field, an electrical field, or use of ultrasound.

Stent Surface Coatings with Functional Properties

In addition to stents that can deliver a therapeutic agent, for instance delivery of a biological polymer on the stent such as a repellant phosphorylcholine, the stent can be coated with other bioresorbable polymers predetermined to promote biological responses in the body lumen desired for certain clinical effectiveness. Further the coating can be used to mask (temporarily or permanently) the surface properties of the polymer used to comprise the stent embodiment. The coating can be selected from the broad class of any biocompatible bioresorbable polymer which can include any one or combination of halogenated and/or non-halogenated which can or cannot comprise any poly(alkylene glycol). These polymers can include compositional variations including homopolymers and heteropolymers, stereoisomers and/or a blend of such polymers. These polymers can include for example, but are not limited to, polycarbonates, polyarylates, poly(ester amides), poly(amide carbonates), trimethylene carbonate, polycaprolactone, polydioxane, polyhydroxybutyrate, polyhydroxyvalerate, polyglycolide, polylactides and stereoisomers and copolymers thereof, such as glycolide/lactide copolymers. In a preferred embodiment, the stent can be coated with a polymer that exhibits a negative charge that repels the negatively charged red blood cells' outer membranes thereby reducing the risk of clot formation. In another preferred embodiment, the stent can be coated with a polymer that exhibits an affinity for cells, (e.g., endothelial cells) to promote healing. In yet another preferred embodiment, the stent can be coated with a polymer that repels the attachment and/or proliferation of specific cells, for instance arterial fibroblasts and/or smooth muscle cells in order to lessen restenosis and/or inflammatory cells such as macrophages.

Described above are embodiments that can be modified with a coating to achieve functional properties that support biological responses. Such coatings or compositions of material with a therapeutic agent can be formed on stents or applied in the process of making a stent body via techniques such as dipping, spray coating, cross-linking combinations thereof, and the like. Such coatings or compositions of material can also serve purpose other than delivering a therapeutic, such as to enhance stent retention on a balloon when the coating is placed intraluminally on the stent body and/or placed over the entire device after the stent is mounted on the balloon system to keep the stent in a collapsed formation. Other purposes can be envisioned by those skilled in the art when using any polymer material.

In one aspect of certain embodiments, a stent would have a coating applied that can alter the physical characteristics of the stent, such as to provide specific mechanical properties to the stent. The properties can include inter alia thickness, tensile strength, glass transition temperature, and surface finish. The coating can be preferably applied prior to final crimping or application of the stent to the catheter. The stent can then be applied to the catheter and the system can have either heat or pressure or both applied in a compressive manner. In the process, the coating can form frangible bonds with both the catheter and the other stent surfaces. The bonds would enable a reliable method of creating stent retention and of holding the stent crossing profile over time. The bonds would break upon the balloon deployment pressures. The coating would be a lower Tg than the substrate to ensure no changes in the substrate.

Stent Deployment

First, a catheter is provided wherein an expandable member, preferably an inflatable balloon, such as an angioplasty balloon, is provided along a distal end portion. One example of a balloon catheter for use with a stent is described in U.S. Pat. No. 4,733,665 to Palmaz, the disclosure of which is incorporated by reference herein. A stent on a catheter can be commonly collectively referred to as a stent system. Catheters include but are not limited to over-the-wire catheters, coaxial rapid-exchange designs and the Medtronic Zipper Technology that is a new delivery platform. Such catheters can include for instance those described in Bonzel U.S. Pat. Nos. 4,762,129 and 5,232,445 and by Yock U.S. Pat. Nos. 4,748,982, 5,496,346, 5,626,600, 5,040,548, 5,061,273, 5,350,395, 5,451,233 and 5,749,888. Additionally, catheters can include for instance those as described in U.S. Pat. Nos. 4,762,129, 5,092,877, 5,108,416, 5,197,978, 5,232,445, 5,300,085, 5,445,646, 5,496,275, 5,545,135, 5,545,138, 5,549,556, 5,755,708, 5,769,868, 5,800,393, 5,836,965, 5,989,280, 6,019,785, 6,036,715, 5,242,399, 5,158,548, and 6,007,545. The disclosures of each of the above-cited patents are incorporated herein in their entirety by reference thereto.

Catheters can be specialized with highly compliant polymers and for various purposes such as to produce an ultrasound effect, electric field, magnetic field, light and/or temperature effect. Heating catheters can include for example those described in U.S. Pat. Nos. 5,151,100, 5,230,349, 6,447,508, and 6,562,021 as well as WO9014046A1. Infrared light emitting catheters can include for example those described in U.S. Pat. Nos. 5,910,816 and 5,423,321. The disclosures of each of the above-cited patents and patent publications are incorporated herein in their entirety by reference thereto.

An expandable member, such as an inflatable balloon, can be preferably used to deploy the stent at the treatment site. As the balloon is expanded, the radial force of the balloon overcomes the initial resistance of the constraining mechanism, thereby allowing the stent to expand.

The stent of embodiments described herein can be adapted for deployment using conventional methods known in the art and employing percutaneous transluminal catheter devices. This can include deployment in a body lumen by means of a balloon expandable design whereby expansion can be driven by the balloon expanding. Alternatively, the stent can be mounted onto a catheter that holds the stent as it is delivered through the body lumen and then releases the stent and allows it to self-expand into contact with the body lumen. The restraining means can comprise a removable/retractable sheath, a sheath that remains with the stent, and/or a mechanical aspect of the stent design.

In accordance with some embodiments, the sheath can be used to control delivery and deployment of the stent. The sheath can be made from a variety of materials, such as polymers, natural materials, etc., which can include biodegradable materials. Further, the polymer can be radiopaque, biocompatible, and/or biodegradable, as discussed herein. For example, in some embodiments, the sheath can be made from a resorbable material, and the sheath and stent can degrade together, thus leaving a healed, unencumbered vessel. The sheath material can be selected such that during stent expansion, the sheath can deform and expand plastically with the stent. In some embodiments, the sheath can have sufficient elasticity to stretch during deployment of the stent without breaking. Although high yield strength may not be required, the material preferably provides the sheath with an elongation at break of greater than 150%, and possibly as much as 300%. Further, the sheath can be very thin, such as less than about 0.002 inch thick, but can preferably be about 0.0005 inch thick; other thicknesses can also be used in accordance with the teachings herein. Thus, the sheath can be beneficially used to eliminate or reduce negative aspects of certain stent designs, such as may be encountered during stent deployment, as well as to make other stent designs possible.

For example, the sheath can be used to control and protect "loose geometry" of the stent. Some stent embodiments can include features that protrude or extend radially outwardly from the stent. Other stent embodiments can include overlying features. In such embodiments, these features tend to create an undulating surface which has the potential to snag when passing within a vessel or traversing a constriction of the vessel. If the stent were to snag, the stent geometry could possibly become bent or damaged, which might result in deployment problems or reduced stent performance. Therefore, a sheath can be utilized to provide a thin covering to the stent geometry and thereby smooth over the undulations and prevent stent geometry from being displaced.

The sheath can also be formed to include structural patterns. Such patterns can be formed by altering the characteristics of the sheath, such as by removing material from, providing additional material for, or using different types of materials for a given portion of the sheath. For example, the sheath can include cutout patterns that can be used to provide lower deployment pressures, increase flexibility and allow access to side branches of the artery, as described in copending U.S. patent application Ser. Nos. 10/897,235 and 11/016,269, the disclosure of each of which is incorporated herein by reference. The stent can be formed to include a solid wall region, and in such embodiments, the solid wall region can be formed to have an opening that allows fluid communication with a side branch vessel. Indeed, various structural patterns could be used, including, but not limited to ellipses, triangles, complicated patterns, non uniform patterns, patterns with different module and spring areas, etc.

Some embodiments can be useful in coronary arteries, carotid arteries, vascular aneurysms (when covered with a sheath), and peripheral arteries and veins (e.g., renal, iliac, femoral, popliteal, subclavian, aorta, intercranial, etc.). Other nonvascular applications include gastrointestinal, duodenum, biliary ducts, esophagus, urethra, reproductive tracts, trachea, and respiratory (e.g., bronchial) ducts. These applications can or cannot require a sheath covering the stent.

It can be desirable to have the stent radially expand in a uniform manner. Alternatively, the expanded diameter can be variable and determined by the internal diameter and anatomy of the body passageway to be treated. Accordingly, uniform and variable expansion of the stent that is controlled during deployment is not likely to cause a rupture of the body passageway. Furthermore, the stent will resist recoil because the locking means resist movement of the mating elements. Thus, the expanded intraluminal stent will continue to exert radial pressure outward against the wall of the body passageway and will therefore, not migrate away from the desired location.

It is to be understood that any range of values disclosed, taught or suggested herein can comprise all values and subranges therebetween. For example, a range from 5 to 10 will comprise all numerical values between 5 and 10 and all subranges between 5 and 10.

From the foregoing description, it will be appreciated that a novel approach for expanding a lumen has been disclosed. While several components, techniques and aspects have been described with a certain degree of particularity, it is manifest that many changes can be made in the specific designs, constructions and methodology herein above described without departing from the spirit and scope of this disclosure.

The methods which are described and illustrated herein are not limited to the sequence of acts described, nor are they necessarily limited to the practice of all of the acts set forth. Other sequences of acts, or less than all of the acts, or simultaneous occurrence of the acts, can be utilized in practicing embodiments.

While a number of preferred embodiments and variations thereof have been described in detail, other modifications and methods of using and medical applications for the same will be apparent to those of skill in the art. Accordingly, it should be understood that various applications, modifications, materials, and substitutions can be made of equivalents without departing from the spirit of the inventions or the scope of the claims.

Various modifications and applications of the embodiments can occur to those who are skilled in the art, without departing from the true spirit or scope of the inventions. It should be understood that the present inventions are not limited to the embodiments set forth herein for purposes of exemplification, but is to be defined only by a fair reading of the claims, including the full range of equivalency to which each element thereof is entitled.

REFERENCES

Some of the references cited herein are listed below, the entirety of each one of which is hereby incorporated by reference herein:

Charles R, Sandirasegarane L, Yun J, Bourbon N, Wilson R, Rothstein R P, et al. Ceramide-Coated Balloon Catheters Limit Neointimal Hyperplasia after Stretch Injury in Carotid Arteries. Circ Res 2000; 87(4):282-288.

Coroneos E, Martinez M, McKenna S, Kester M. Differential regulation of sphingomyelinase and ceramidase activities by growth factors and cytokines. Implications for cellular proliferation and differentiation. J Biol Chem 1995;270(40):23305-9.

Coroneos E, Wang Y, Panuska J R, Templeton D J, Kester M. Sphingolipid metabolites differentially regulate extracellular signal-regulated kinase and stress-activated protein kinase cascades. Biochem J 1996;316(Pt 1):13-7.

Jacobs L S, Kester M. Sphingolipids as mediators of effects of platelet-derived growth factor in vascular smooth muscle cells. Am J Physiol 1993;265(3 Pt 1):C740-7.

Tanguay J F, Zidar J P, Phillips H R, 3rd, Stack R S. Current status of biodegradable stents. Cardiol Clin 1994;12(4): 699-713.

Nikol S, Huehns T Y, Hofling B. Molecular biology and post-angioplasty restenosis. Atherosclerosis 1996;123 (1-2):17-31.

Biomaterials Science: An Introduction to Materials in Medicine (29 Jul. 2004) Ratner, Hoffman, Schoen, and Lemons

What is claimed is:

1. A circumferentially nested scissor stent being expandable from a collapsed state to an expanded state, the stent comprising a tubular member having longitudinal and circumferential axes, the tubular member comprising:

at least one linkage section being disposed along the circumferential axis, the linkage section comprising at least one structural element, the structural element comprising:

first and second bars each having first and second ends, the bars being disposed along the circumferential axis of the tubular member, the bars being rotatably connected at the first ends thereof to form a coupling, the first bar having an aperture disposed through a portion of the first end thereof; and an articulating member having first and second ends, the first end of the articulating member being connected to the first end of the second bar adjacent the coupling with the articulating member extending upwardly from therefrom into the aperture of the first bar, the articulating member having a plurality of teeth disposed therealong, the teeth being sized and configured to engage the aperture for providing one-way translational withdrawal of the articulating member from the aperture upon angular separation of the first bar from the second bar;

wherein the first bar is positionable substantially circumferentially adjacent to the second bar when the stent is in the unexpanded state, the first bar being separable from the second bar upon angular rotation of the first bar with respect to the second bar at the coupling thereby expanding the stent to the expanded state, the one-way translational withdrawal of the articulating member from the aperture maintaining angular displacement between the first and second bars at the coupling in order to prevent collapse of the stent to the collapsed state upon being expanded to the expanded state.

2. The stent of claim 1 wherein the linkage section includes a plurality of structural elements being rotatably connected to form a plurality of couplings, wherein each structural element includes an articulating member corresponding to each coupling.

* * * * *

UNITED STATES PATENT AND TRADEMARK OFFICE
CERTIFICATE OF CORRECTION

PATENT NO. : 7,704,275 B2
APPLICATION NO. : 11/627898
DATED : April 27, 2010
INVENTOR(S) : Schmid et al.

It is certified that error appears in the above-identified patent and that said Letters Patent is hereby corrected as shown below:

In Column 1, line 48, please change "vascualr" to --vascular--.

In Column 1, line 52, please change "periadverntital" to --periadventitial--.

In Column 1, line 56, please delete "plasminogen" and insert --activator--.

In Column 2, line 16, please change "in tact." to --intact.--.

In Column 2, line 19, please change "funtion," to --function,--.

In Column 2, line 29, please change "23305-22309." to --23305-23309.--.

In Column 5, line 41, please change "disposed at least" to --disposed at at least--.

In Column 7, line 26, after "bars" please insert --.--.

In Column 7, line 55, after "bars" please insert --.--.

In Column 10, lines 37-38, please change "platinum-irridium" to --platinum-iridium--.

In Column 14, line 20, please change "stereoisomersm," to --stereoisomerism,--.

In Column 17, line 30, after "expansion" please insert --.--.

In Column 24, line 64, please change "30Cn'"" to --30cN''--.

In Column 24, line 66, please change "40CN'"" to --40cN''--.

In Column 29, line 25-26, please change "a an" to --an--.

Signed and Sealed this
Fourth Day of January, 2011

David J. Kappos
*Director of the United States Patent and Trademark Office*

CERTIFICATE OF CORRECTION (continued)
U.S. Pat. No. 7,704,275 B2

In Column 30, line 63, please change "(PHV/PHB)," to --(PHB/PHV),--.

In Column 31, line 1, please change "polyorthesters," to --polyorthoesters,--.

In Column 31, line 5, please change "polydepsidpetides," to --polydepsipeptides,--.

In Column 31, line 17, please change "polyalkanotes" to --polyalkanoates--.

In Column 31, line 31, please change "resiussed" to --reissued--.

In Column 31, line 32, please change "resiussed" to --reissued--.

In Column 31, line 57, please change "polydepsidpetides," to --polydepsipeptides,--.

In Column 32, line 17 (approximately), please change "Poly(tetraflouroethylene)" to --Poly(tetrafluoroethylene)--.

In Column 40, line 43, after "Lemons" insert --.--.